US008802112B2

(12) United States Patent
Ratner

(10) Patent No.: US 8,802,112 B2
(45) Date of Patent: Aug. 12, 2014

(54) TREATMENT AND PREVENTION OF GARDNERELLA VAGINALIS INFECTIONS

(75) Inventor: Adam J. Ratner, New York, NY (US)

(73) Assignee: The Trustees of Columbia University in the City of New York, New York, NY (US)

(*) Notice: Subject to any disclaimer, the term of this patent is extended or adjusted under 35 U.S.C. 154(b) by 492 days.

(21) Appl. No.: 12/922,837

(22) PCT Filed: Mar. 16, 2009

(86) PCT No.: PCT/US2009/037328
§ 371 (c)(1),
(2), (4) Date: Sep. 15, 2010

(87) PCT Pub. No.: WO2009/117373
PCT Pub. Date: Sep. 24, 2009

(65) Prior Publication Data
US 2011/0020355 A1 Jan. 27, 2011

Related U.S. Application Data

(60) Provisional application No. 61/036,943, filed on Mar. 15, 2008, provisional application No. 61/057,190, filed on May 29, 2008.

(51) Int. Cl.
A61K 39/00 (2006.01)
A61K 39/02 (2006.01)
C07K 1/00 (2006.01)
C07K 14/00 (2006.01)

(52) U.S. Cl.
USPC .................. 424/236.1; 424/184.1; 424/185.1; 424/190.1; 530/350

(58) Field of Classification Search
None
See application file for complete search history.

(56) References Cited

FOREIGN PATENT DOCUMENTS

| JP | 2007085783 | * | 4/2007 |
| WO | WO 0131019 A2 | * | 5/2001 |
| WO | WO 2005108419 A1 | * | 11/2005 |

OTHER PUBLICATIONS

Rottini et al. Infection and Immunity, vol. 58, No. 11, 1990, p. 3751-3758.*
Turovskiy et al. J Appl Microbiol. May 2011; 110(5):1105-1128.*
Definition of "vaccine". The Dictionary of Immunology, Herbert et al eds, Academic Press, 1995.*
Cauci et al. Molecular Microbiol (1993) 9(6),1143-1155.*
AB029317, Streptococcus intermedius ily gene for intermedilysin, complete cds, 2000. [online]. [Retrieved on Sep. 8, 2009]. Retrieved from the internet: <URL: http://www.ncbi.nlm.nih.gov/nuccore/6729343>.

Billington, S. et al., The variant undecapeptide sequence of the Arcanobacterium pyogenes haemolysin, pyolysin, is required for full cytolytic activity, journal, Microbiology, 2002, pp. 3947-3954, SGM, Great Britain.
Cauci, S. et al., Pore-forming and haemolytic properties of the Gardnerella vaginalis cytolysin, article, Sep. 9, 1993, p. 143, Italy.
EU522486, Gardnerella vaginalis strain 14018 vaginolysin (VLY) gene, complete cds, May 19, 2008. [online]. [Retrieved on Sep. 8, 2009]. Retrieved from the internet: <URL: http://www.ncbi.nlm.nih.gov/nuccore/187940698>.
EU522488, Gardnerella vaginalis strain 49145 vaginolysin (VLY) gene, complete cds, May 19, 2008. [online]. [Retrieved on Sep. 8, 2009]. Retrieved from the internet: <URL: http://www.ncbi.nlm.nih.gov/nuccore/187940702>.
Gelber, S. et al., Functional and Phylogenetic Characterization of Vaginolysin, the Human-Specific Cytolysin from Gardnerella vaginalis, journal, Journal of Bacteriology, Mar. 27, 2008, pp. 3896-3903, American Society for Microbiology.
International Search Report, PCT/US 09/37328, Oct. 15, 2009, pp. 1-6.
Nagamune, H. et al., Distribution of the Intermedilysin Gene among the Anginosus Group Streptococci and Correlation between Intermedilysin Productin and Deep-Seated Infection with Streptococcus intermedius, journal, Journal of Clinical Microbiology, Oct. 1 1999, pp. 220-226, vol. 28, No. 1, American Society for Microbiology.
Watanabe et al. Streptococus mitis samhpaf gene for human platelet aggregation factor Sm-hPAF, complete cds. GenBank: AB051299. 1, 2006 [online]. [Retrieved on Sep. 9, 2009]. Retrived from the internet: <URL: http://www.ncbi.nlm.nih.gov/nuccore/84579713>.
Cauci, Sabina et al., "Pore-forming and haemolytic prooperties of the Gardnerella vaginalis cytolysin", "Molecular Microbiology", May 17, 1993, pp. 1143-1155, vol. 9, No. 6, Publisher: John Wiley & Sons, Ltd, Published in: http://onlinelibrary.wiley.com/doi/10.1111/j.1365-2958.1993.tb01244.x/pdf.
Gelber, Shari E., et al., "Functional and Phylogenetic Characterization of Vaginolysin, the Human-Specific Cytolysin from Gardnerella vaginalis", "Journal of Bacteriology", Apr. 4, 2008, pp. 3896-3903, vol. 190, No. 11, Publisher: American Society for Microbiology, Published in: http://jb.asm.org.
Giddings, K., et al., "Human CD59 is a receptor for the cholesterol-dependent cytolysin intermedilysin", "Nature Structural & Molecular Biology", Nov. 14, 2004, pp. 1173-1178, vol. 11, No. 12, Publisher: Nature Publishing Group, Published in: http://www.nature.com/nsmb.

(Continued)

Primary Examiner — Oluwatosin Ogunbiyi
(74) Attorney, Agent, or Firm — Evans & Molinelli PLLC; Judith A. Evans

(57) ABSTRACT

The present invention is drawn to the nucleic and amino acid sequences encoding vaginolysin (VLY) toxin from Gardnerella vaginalis, and biologically active fragments and variants thereof. The invention is also directed to anti-VLY antibodies and to their use therapeutically and in a new ELISA assay of VLY toxin. Other embodiments of the invention are directed to VLY toxoids and to vaccines that use the new VLY toxoids as immunogens.

13 Claims, 10 Drawing Sheets

(56) References Cited

OTHER PUBLICATIONS

Hillier, Sharon L., "The Complexity of Microbial Diversity in Bacterial Vaginosis", "The New England Journal of Medicine", Nov. 3, 2005, pp. 1886-1887, vol. 353, No. 18, Publisher: NEJM Group, Published in: http://www.nejm.org.

Korchev, Y., et al., "A conserved tryptophan in pneumolysin is a determinant of the characteristics of channels formed by pneumolysin in cells and planar lipid bilayers", "Biochemical Journal", 1998, pp. 571-577, vol. 329, Publisher: Portland Press Ltd., Published in: http://www.biochemj.org/bj/default.htm.

Nagamune, H., et al., "Intermedilysin, a Novel Cytotoxin Specific for Human Cells, Secreted by *Streptococcus intermedius* UNS46 Isolated from a Human Liver Abscess", "Infection and Immunity", Aug. 1996, pp. 3093-3100, vol. 64, No. 8, Publisher: American Society for Microbiology, Published in: http://iai.asm.org/content/by/year.

Polekhina, G., et al., "Insights into the action of the superfamily of cholesterol-dependent cytolysins from stuides of intermedilysin", "PNAS", Jan. 18, 2005, pp. 600-605, vol. 102, No. 3, Publisher: The National Academy of Sciences of the USA, Published in: http://www.pnas.org/cgi/doi/10.1073/pnas.0403229101.

Ratner, A., et al., "Epithelial Cells Are Sensitive Detectors of Bacterial Pore-Forming Toxins", J. Biol. Chem., May 5, 2006, pp. 12994-12998, vol. 281, No. 18, Publisher: American Society for Biochemistry and Molecular Biology, Published in: http://www.jbc.org/content/by/year.

Rottini, G., et al., "Identification and Partial Characterization of a Cytolytic Toxin Produced by *Gardnerella vaginalis*", "Infection and Immunity", Nov. 1990, pp. 3751-3758, vol. 58, No. 11, Publisher: American Society for Microbiology, Published in: http://www.ncbi.nlm.nih.gov/pmc/articles/PMC313724/.

Tweten, Rodney K., "Cholesterol-Dependent Cytolysins, a Family of Versatile Pore-Forming Toxins", "Infection and Immunity", 2005, pp. 6199-6209, vol. 73, No. 10, Publisher: Ameican Society for Microbiology, Published in: http://iai.asm.org/.

* cited by examiner

FIG. 1A
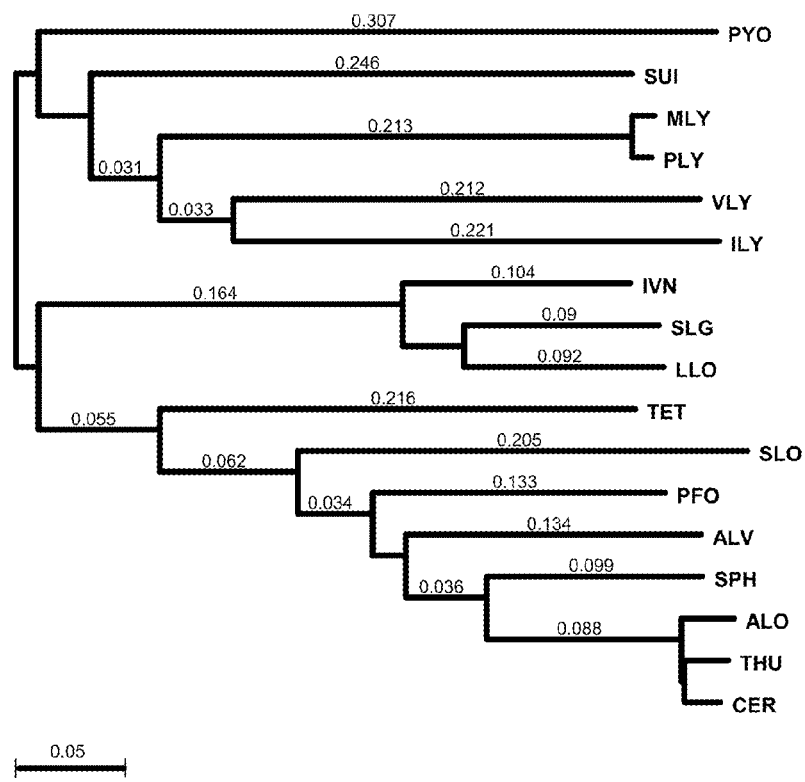
FIG. 1B
| VLY | EKTGLVWEPWR |
| ILY | GATGLAWEPWR |
| PYO | EATGLAWDPWW |
| SLG | ECTGLFWEWWR | ←
| CONSENSUS | ECTGLAWEWWR |
FIG. 1C
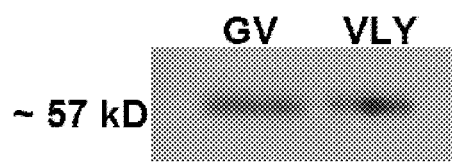
~ 57 kD Pre-immune                    Anti-VLY

SEQUENCE LISTING

<160> NUMBER OF SEQ ID NOS: 35

<210> SEQ ID NO 1
<211> LENGTH: 1551
<212> TYPE: DNA
<213> ORGANISM: Gardnerella vaginalis

<400> SEQUENCE: 1

```
atgaagagta caaagttcta ccgtaatgca gcaatgttgc tcctcgcggg cgcaactatt    60
gttccacaat gcttagcagc accagcaatg ccgctccctt ccgctaagga ttctgaacca   120
gctacatctt gcgcagctaa gaaagactcg ttgaataatt atttgtggga tttgcaatac   180
gataaaacaa acattctcgc ccgtcatggc gaaaccattg agaacaaatt ctccagcgac   240
agcttcaaca gaacggtga attcgttgtt gttgagcatc agaagaagaa catcaccaat   300
acaacttcaa atttgtcggt tacttccgcc aacgatgatc gcgtatacccc aggtgctctt   360 ttccgtgctg ataagaattt gatggacaat atgccaagcc tgatttctgc aaaccgcgct   420
ccaataacgt tgagcgttga tttgccggga ttccacggcg gcgaaagtgc tgtaactgtt   480
cagcgcccaa ccaagagctc tgtaacttcc gcagtgaacg gcttagtttc taagtggaat   540
gcacaatatg gagcaagtca tcatgttgca gctcgcatgc agtacgattc tgcaagcgca   600
caaagcatga accagctcaa ggctaagttt ggtgctgatt ttgccaagat tggtgttccg   660
ctgaagattg atttcgatgc agtacacaag ggtgagaagc agactcaaat tgtgaacttc   720
```

```
aagcaaactt actacaccgt aagcgttgat gcaccagata gcccagcaga tttctttgct    780
ccttgcacta cgccagacag cttgaagaac cgtggcgttg acaacaagcg cccaccagtt    840
tacgtgtcaa acgtagctta tggtcgctca atgtacgtaa agttcgatac caccagcaag    900
agcactgatt tccaggctgc ggtagaagca gcaattaagg gcgtagaaat caagccaaac    960
accgaattcc atcgcattct ccagaatact tctgttactg cagtgattct tggtggcagc   1020
gctaatggtg cagctaaagt tattacaggc aatatcgata cgcttaaggc tttgattcag   1080
gaaggtgcaa atttgagcac ctctagccca gcggttccaa ttgcatacac cacttccttc   1140
gtcaaggata cgaagtagc  aactttgcaa tccaacagcg attatattga acgaaggtt    1200 tcttcttatc gcaatggcta cttgactttg gaccaccgtg gagcttatgt agctcgctac   1260
tacatctact gggatgagta cggcaccgaa attgacggca ctccttacgt gcgttctcgc   1320
gcttgggaag gcaatggtaa gtatcgtaca gctcacttca acaccactat tcagttcaaa   1380
ggaaatgtac gcaatctacg aatcaagttg gttgaaaaga ctggtttggt ttgggaacca   1440
tggcgcacag tatatgaccg ttctgatttg ccactagttc gtcagcgtac tattagcaac   1500
tggggcacaa ccttgtggcc tcgcgttgct gaaactgtaa agaacgactg a            1551
```

<210> SEQ ID NO 2
<211> LENGTH: 516
<212> TYPE: PRT
<213> ORGANISM: Gardnerella vaginalis

<400> SEQUENCE: 2

```
Met Lys Ser Thr Lys Phe Tyr Arg Asn Ala Ala Met Leu Leu Leu Ala
1               5                   10                  15

Gly Ala Thr Ile Val Pro Gln Cys Leu Ala Ala Pro Ala Met Ala Ala
                20                  25                  30

Pro Ser Ala Lys Asp Ser Glu Pro Ala Thr Ser Cys Ala Ala Lys Lys
            35                  40                  45

Asp Ser Leu Asn Asn Tyr Leu Trp Asp Leu Gln Tyr Asp Lys Thr Asn
        50                  55                  60

Ile Leu Ala Arg His Gly Glu Thr Ile Glu Asn Lys Phe Ser Ser Asp
65                  70                  75                  80

Ser Phe Asn Lys Asn Gly Glu Phe Val Val Glu His Gln Lys Lys
                85                  90                  95

Asn Ile Thr Asn Thr Thr Ser Asn Leu Ser Val Thr Ser Ala Asn Asp
            100                 105                 110

Asp Arg Val Tyr Pro Gly Ala Leu Phe Arg Ala Asp Lys Asn Leu Met
        115                 120                 125

Asp Asn Met Pro Ser Leu Ile Ser Ala Asn Arg Ala Pro Ile Thr Leu
    130                 135                 140

Ser Val Asp Leu Pro Gly Phe His Gly Gly Glu Ser Ala Val Thr Val
145                 150                 155                 160

Gln Arg Pro Thr Lys Ser Ser Val Thr Ser Ala Val Asn Gly Leu Val
                165                 170                 175

Ser Lys Trp Asn Ala Gln Tyr Gly Ala Ser His His Val Ala Ala Arg
            180                 185                 190

Met Gln Tyr Asp Ser Ala Ser Ala Gln Ser Met Asn Gln Leu Lys Ala
        195                 200                 205

Lys Phe Gly Ala Asp Phe Ala Lys Ile Gly Val Pro Leu Lys Ile Asp
    210                 215                 220
```

```
Phe Asp Ala Val His Lys Gly Glu Lys Gln Thr Gln Ile Val Asn Phe
225                 230                 235                 240

Lys Gln Thr Tyr Tyr Thr Val Ser Val Asp Ala Pro Asp Ser Pro Ala
            245                 250                 255

Asp Phe Phe Ala Pro Cys Thr Thr Pro Asp Ser Leu Lys Asn Arg Gly
        260                 265                 270

Val Asp Asn Lys Arg Pro Pro Val Tyr Val Ser Asn Val Ala Tyr Gly
    275                 280                 285

Arg Ser Met Tyr Val Lys Phe Asp Thr Thr Ser Lys Ser Thr Asp Phe
290                 295                 300

Gln Ala Ala Val Glu Ala Ala Ile Lys Gly Val Glu Ile Lys Pro Asn
305                 310                 315                 320

Thr Glu Phe His Arg Ile Leu Gln Asn Thr Ser Val Thr Ala Val Ile
            325                 330                 335

Leu Gly Gly Ser Ala Asn Gly Ala Ala Lys Val Ile Thr Gly Asn Ile
        340                 345                 350

Asp Thr Leu Lys Ala Leu Ile Gln Glu Gly Ala Asn Leu Ser Thr Ser
    355                 360                 365

Ser Pro Ala Val Pro Ile Ala Tyr Thr Thr Ser Phe Val Lys Asp Asn
370                 375                 380

Glu Val Ala Thr Leu Gln Ser Asn Ser Asp Tyr Ile Glu Thr Lys Val
385                 390                 395                 400

Ser Ser Tyr Arg Asn Gly Tyr Leu Thr Leu Asp His Arg Gly Ala Tyr
            405                 410                 415

Val Ala Arg Tyr Tyr Ile Tyr Trp Asp Glu Tyr Gly Thr Glu Ile Asp
        420                 425                 430

Gly Thr Pro Tyr Val Arg Ser Arg Ala Trp Glu Gly Asn Gly Lys Tyr
    435                 440                 445

Arg Thr Ala His Phe Asn Thr Thr Ile Gln Phe Lys Gly Asn Val Arg
450                 455                 460

Asn Leu Arg Ile Lys Leu Val Glu Lys Thr Gly Leu Val Trp Glu Pro
465                 470                 475                 480

Trp Arg Thr Val Tyr Asp Arg Ser Asp Leu Pro Leu Val Arg Gln Arg
            485                 490                 495

Thr Ile Ser Asn Trp Gly Thr Thr Leu Trp Pro Arg Val Ala Glu Thr
        500                 505                 510

Val Lys Asn Asp
        515

<210> SEQ ID NO 3
<211> LENGTH: 1551
<212> TYPE: DNA
<213> ORGANISM: Gardnerella vaginalis

<400> SEQUENCE: 3
atgaagagta caaagttcta ccgtaatgca gcaatgttgc tcctcgcggg cgcaactatt      60
gttccacaat gcttagcagc accagcaatg gccgctcctt ccgctaagga ttctgaacca     120
gctacatctt gcgcagctaa gaaagactcg ttgaataatt atttgtggga tttgcaatac     180
gataaaacaa acattctcgc ccgtcatggc gaaaccattg agaacaaatt ctccagcgac     240
agcttcaaca agaacggtga attcgttgtt gttgagcatc agaagaagaa catcaccaat     300
acaacttcaa atttgtcggt tacttccgcc aacgatgatc gcgtataccc aggtgctctt     360
ttccgtgctg ataagaattt gatggacaat atgccaagcc tgatttctgc aaaccgcgct     420
```

```
ccaataacgt tgagcgttga tttgccggga ttccacggcg cgaaagtgc  tgtaactgtt    480 cagcgcccaa ccaagagctc tgtaacttcc gcagtgaacg gcttagtttc taagtggaat    540
gcacaatatg gagcaagtca tcatgttgca gctcgcatgc agtacgattc tgcaagcgca    600
caaagcatga accagctcaa ggctaagttt ggtgctgatt ttgccaagat tggtgttccg    660
ctgaagattg atttcgatgc agtacacaag ggtgagaagc agactcaaat tgtgaacttc    720
aagcaaactt actacaccgt aagcgttgat gcaccagata gcccagcaga tttctttgct    780
ccttgcacta cgccagacag cttgaagaac cgtggcgttg acaacaagcg cccaccagtt    840
tacgtgtcaa acgtagctta tggtcgctca atgtacgtaa agttcgatac caccagcaag    900
agcactgatt tccaggctgc agtagaagca gcaattaagg gcgtagaaat caagccaaac    960
accgaattcc atcgcattct ccaaaatact tctgttactg cagtgattct tggtggcagc   1020
gctaatggtg cagctaaagt tattacaggc aacatcgata cgttgaaggc tttgattcag   1080
gaaggtgcaa atttgagcac ctctagccca gcagttccaa ttgcatacac cacttccttc   1140
gtcaaggata acgaagtagc aactttgcaa tccaacagcg attatattga aacgaaggtt   1200
tcctcttacc gcaatggcta cttgactttg gaccaccgtg gagcttacgt agctcgctac   1260
tacatctact gggatgagta cggcaccgaa attgacggca ctccttacgt gcgttctcgc   1320
gcttgggaag gcaatggtaa gtatcgtaca gctcacttca ataccactat tcagttcaaa   1380
ggaaatgtac gcaatctacg aatcaagttg gttgaaaaga ctggtttagt ttgggaacca   1440
tggcgcacag tatatgaccg ttctgatttg ccactagttc atcagcgtac tattagcaac   1500
tggggcacaa ccttgtggcc tcgcgttgct gaaactgtaa agaacgactg a            1551

<210> SEQ ID NO 4
<211> LENGTH: 426
<212> TYPE: DNA
<213> ORGANISM: Gardnerella vaginalis

<400> SEQUENCE: 4
tacaccactt ccttcgtcaa ggataacgaa gtagcaactt tgcaatccaa cagcgattat     60
attgaaacga aggtttcttc ttatcgcaat ggctacttga cttttggacca ccgtggagct    120 tatgtagctc gctactacat ctactgggat gagtacggca ccgaaattga cggcactcct    180
tacgtgcgtt ctcgcgcttg ggaaggcaat ggtaagtatc gtacagctca cttcaacacc    240
actattcagt tcaaaggaaa tgtacgcaat ctacgaatca gttggttga aaagactggt    300 ttggtttggg aaccatggcg cacagtatat gaccgttctg atttgccact agttcgtcag    360
cgtactatta gcaactgggg cacaaccttg tggcctcgcg ttgctgaaac tgtaaagaac    420
gactga                                                                426

<210> SEQ ID NO 5
<211> LENGTH: 141
<212> TYPE: PRT
<213> ORGANISM: Gardnerella vaginalis

<400> SEQUENCE: 5

Tyr Thr Thr Ser Phe Val Lys Asp Asn Glu Val Ala Thr Leu Gln Ser
1               5                   10                  15

Asn Ser Asp Tyr Ile Glu Thr Lys Val Ser Ser Tyr Arg Asn Gly Tyr
            20                  25                  30

Leu Thr Leu Asp His Arg Gly Ala Tyr Val Ala Arg Tyr Tyr Ile Tyr
        35                  40                  45
```

```
Trp Asp Glu Tyr Gly Thr Glu Ile Asp Gly Thr Pro Tyr Val Arg Ser
 50                  55                  60

Arg Ala Trp Glu Gly Asn Gly Lys Tyr Arg Thr Ala His Phe Asn Thr
 65                  70                  75                  80

Thr Ile Gln Phe Lys Gly Asn Val Arg Asn Leu Arg Ile Lys Leu Val
                 85                  90                  95

Glu Lys Thr Gly Leu Val Trp Glu Pro Trp Arg Thr Val Tyr Asp Arg
            100                 105                 110

Ser Asp Leu Pro Leu Val Arg Gln Arg Thr Ile Ser Asn Trp Gly Thr
        115                 120                 125

Thr Leu Trp Pro Arg Val Ala Glu Thr Val Lys Asn Asp
    130                 135                 140

<210> SEQ ID NO 6
<211> LENGTH: 33
<212> TYPE: DNA
<213> ORGANISM: Gardnerella vaginalis

<400> SEQUENCE: 6
gaaaagactg gtttggtttg gaaccatgg cgc                               33

<210> SEQ ID NO 7
<211> LENGTH: 11
<212> TYPE: PRT
<213> ORGANISM: Gardnerella vaginalis

<400> SEQUENCE: 7

Glu Lys Thr Gly Leu Val Trp Glu Pro Trp Arg
 1               5                  10

<210> SEQ ID NO 8
<211> LENGTH: 11
<212> TYPE: PRT
<213> ORGANISM: Gardnerella vaginalis

<400> SEQUENCE: 8

Glu Lys Thr Gly Leu Val Trp Glu Trp Trp Arg
 1               5                  10

<210> SEQ ID NO 9
<211> LENGTH: 1551
<212> TYPE: DNA
<213> ORGANISM: Gardnerella vaginalis

<400> SEQUENCE: 9
atgaaaagca ccaaatttta tcgtaacgcg gcgatgctgc tgctggcagg tgcaaccatt    60
gtgccgcagt gcctggcagc accggcaatg cagcaccga gcgcaaaaga tagcgaaccg    120
gcgaccagct gcgcggcgaa aaagatagc ctgaacaact atctgtggga tctgcagtat    180
gataaaacca acattctggc gcgtcatggc gaaaccattg aaacaaatt tagcagcgat    240 agctttaaca aaaacggcga atttgtggtg gtggaacatc agaagaaaaa cattaccaac    300
accaccagca acctgagcgt gaccagcgcg aacgatgatc gtgtgtatcc gggcgcgctg    360
tttcgtgcgg ataaaaacct gatggataac atgccgagcc tgattagcgc gaaccgtgcg    420
ccgattaccc tgagcgtgga tctgccgggc tttcatggcg cgaaagcgc ggtgaccgtg    480 cagcgtccga ccaaaagcag cgtgaccagc gcggtgaacg gcctggttag caaatggaac    540
gcgcagtatg gcgcgagcca tcatgtgcg gcgcgtatgc agtatgatag cgcgagcgcg    600
cagagcatga accagctgaa agcgaaattt ggcgcggatt ttgcgaaaat ggcgtgccg    660
```

-continued

```
ctgaaaattg attttgatgc ggtgcataaa ggcgaaaaac agacccagat tgtgaacttt       720
aaacagacct attataccgt gagcgtggat gcgccggata gcccggcgga tttcttttgcg      780
ccgtgcacca ccccggatag cctgaaaaac cgtggcgtgg ataacaaacg tccgccggtg       840
tatgtgagca acgtggcgta tggccgtagc atgtatgtga atttgatac  caccagcaaa       900
agcaccgatt ttcaggcggc ggtggaagcg gcgattaaag gcgtggaaat taaaccgaac       960
accgaatttc atcgtattct gcagaacacc agcgtgaccg cggtgattct gggcggcagc      1020
gcgaacggcg cggcgaaagt gattaccggc aacattgata ccctgaaagc gctgattcag      1080
gaaggcgcga acctgagcac cagcagcccg cgggtgccga ttgcgtatac caccagcttt      1140
gtgaaagata acgaagtggc gaccctgcag agcaacagcg attatattga aaccaaagtg      1200
agcagctatc gtaacggcta tctgaccctg gatcatcgtg gcgcgtatgt ggcgcgttat      1260
tatatttatt gggatgaata tggcaccgaa attgatggca ccccgtatgt gcgtagccgt      1320
gcgtgggaag gcaacggcaa atatcgtacc gcgcattta  acaccaccat tcagtttaaa      1380
ggcaacgtgc gtaacctgcg tattaaactg gtggaaaaaa ccggcctggt gtgggaaccg      1440
tggcgtaccg tgtatgatcg tagcgatctg ccgctggtgc gtcagcgtac cattagcaac      1500
tggggcacca ccctgtggcc gcgtgtggcg gaaaccgtga aaaacgatta a             1551

<210> SEQ ID NO 10
<211> LENGTH: 1551
<212> TYPE: DNA
<213> ORGANISM: Gardnerella vaginalis

<400> SEQUENCE: 10
atgaagagta caaagttcta ccgtaatgca gcaatgttgc tcctcgcggg cgcaactatt        60
gttccacaat gcttagcagc accagcaatg gccgctcctt ccgctaagga ttctgaacca       120
gctacatctt gcgcagctaa gaaagactcg ttgaataatt attttgtggga tttgcaatac      180
gataaaacaa acattctcgc ccgtcatggc gaaaccattg agaacaaatt ctccagcgac      240
agcttcaaca agaacggtga attcgttgtt gttgagcatc agaagaagaa catcaccaat      300
acaacttcaa atttgtcggt tacttccgcc aacgatgatc gcgtatacc  aggtgctctt      360
ttccgtgctg ataagaattt gatggacaat atgccaagcc tgatttctgc aaaccgcgct      420
ccaataacgt tgagcgttga tttgccggga ttccacggcg cgaaagtgc  tgtaactgtt      480
cagcgcccaa ccaagagctc tgtaacttcc gcagtgaacg gcttagtttc taagtggaat      540
gcacaatatg gagcaagtca tcatgttgca gctcgcatgc agtacgattc tgcaagcgca      600
caaagcatga accagctcaa ggctaagttt ggtgctgatt ttgccaagat tggtgttccg      660
ctgaagattg atttcgatgc agtacacaag ggtgagaagc agactcaaat tgtgaacttc      720
aagcaaactt actacaccgt aagcgttgat gcaccagata gcccagcaga tttctttgct      780
ccttgcacta cgccagacag cttgaagaac cgtggcgttg acaacaagcg cccaccagtt      840
tacgtgtcaa acgtagctta tggtcgctca atgtacgtaa agttcgatac caccagcaag      900
agcactgatt tccaggctgc ggtagaagca gcaattaagg gctagaaaat caagccaaac      960
accgaattcc atcgcattct ccagaatact tctgttactg cagtgattct tggtggcagc     1020
gctaatggtg cagctaaagt tattacaggc aatatcgata cgcttaaggc tttgattcag     1080
gaaggtgcaa atttgagcac ctctagccca gcggttccaa ttgcatacac cacttccttc     1140
gtcaaggata acgaagtagc aactttgcaa tccaacagcg attatattga aacgaaggtt     1200
```

-continued

```
tcttcttatc gcaatggcta cttgactttg gaccaccgtg gagcttatgt agctcgctac    1260
tacatctact gggatgagta cggcaccgaa attgacggca ctccttacgt gcgttctcgc    1320
gcttgggaag gcaatggtaa gtatcgtaca gctcacttca acaccactat tcagttcaaa    1380
ggaaatgtac gcaatctacg aatcaagttg gttgaaaaga ctggtttggt ttgggaacca    1440
tggcgcacag tatatgaccg ttctgatttg ccactagttc gtcagcgtac tattagcaat    1500
tggggcacaa ccttgtggcc tcgcgttgct gaaactgtaa agaacgactg a              1551
```

<210> SEQ ID NO 11
<211> LENGTH: 516
<212> TYPE: PRT
<213> ORGANISM: Gardnerella vaginalis

<400> SEQUENCE: 11

```
Met Lys Ser Thr Lys Phe Tyr Arg Asn Ala Ala Met Leu Leu Leu Ala
1               5                   10                  15

Gly Ala Thr Ile Val Pro Gln Cys Leu Ala Ala Pro Ala Met Ala Ala
            20                  25                  30

Pro Ser Ala Lys Asp Ser Glu Pro Ala Thr Ser Cys Ala Ala Lys Lys
        35                  40                  45

Asp Ser Leu Asn Asn Tyr Leu Trp Asp Leu Gln Tyr Asp Lys Thr Asn
    50                  55                  60

Ile Leu Ala Arg His Gly Glu Thr Ile Glu Asn Lys Phe Ser Ser Asp
65                  70                  75                  80

Ser Phe Asn Lys Asn Gly Glu Phe Val Val Glu His Gln Lys Lys
                85                  90                  95

Asn Ile Thr Asn Thr Thr Ser Asn Leu Ser Val Thr Ser Ala Asn Asp
            100                 105                 110

Asp Arg Val Tyr Pro Gly Ala Leu Phe Arg Ala Asp Lys Asn Leu Met
        115                 120                 125

Asp Asn Met Pro Ser Leu Ile Ser Ala Asn Arg Ala Pro Ile Thr Leu
    130                 135                 140

Ser Val Asp Leu Pro Gly Phe His Gly Gly Glu Ser Ala Val Thr Val
145                 150                 155                 160

Gln Arg Pro Thr Lys Ser Ser Val Thr Ser Ala Val Asn Gly Leu Val
                165                 170                 175

Ser Lys Trp Asn Ala Gln Tyr Gly Ala Ser His His Val Ala Ala Arg
            180                 185                 190

Met Gln Tyr Asp Ser Ala Ser Ala Gln Ser Met Asn Gln Leu Lys Ala
        195                 200                 205

Lys Phe Gly Ala Asp Phe Ala Lys Ile Gly Val Pro Leu Lys Ile Asp
    210                 215                 220

Phe Asp Ala Val His Lys Gly Glu Lys Gln Thr Gln Ile Val Asn Phe
225                 230                 235                 240

Lys Gln Thr Tyr Tyr Thr Val Ser Val Asp Ala Pro Asp Ser Pro Ala
                245                 250                 255

Asp Phe Phe Ala Pro Cys Thr Thr Pro Asp Ser Leu Lys Asn Arg Gly
            260                 265                 270

Val Asp Asn Lys Arg Pro Pro Val Tyr Val Ser Asn Val Ala Tyr Gly
        275                 280                 285

Arg Ser Met Tyr Val Lys Phe Asp Thr Thr Ser Lys Ser Thr Asp Phe
    290                 295                 300

Gln Ala Ala Val Glu Ala Ala Ile Lys Gly Val Glu Ile Lys Pro Asn
305                 310                 315                 320
```

Thr Glu Phe His Arg Ile Leu Gln Asn Thr Ser Val Thr Ala Val Ile
            325                 330                 335

Leu Gly Gly Ser Ala Asn Gly Ala Ala Lys Val Ile Thr Gly Asn Ile
        340                 345                 350

Asp Thr Leu Lys Ala Leu Ile Gln Glu Gly Ala Asn Leu Ser Thr Ser
            355                 360                 365

Ser Pro Ala Val Pro Ile Ala Tyr Thr Thr Ser Phe Val Lys Asp Asn
    370                 375                 380

Glu Val Ala Thr Leu Gln Ser Asn Ser Asp Tyr Ile Glu Thr Lys Val
385                 390                 395                 400

Ser Ser Tyr Arg Asn Gly Tyr Leu Thr Leu Asp His Arg Gly Ala Tyr
                405                 410                 415

Val Ala Arg Tyr Tyr Ile Tyr Trp Asp Glu Tyr Gly Thr Glu Ile Asp
            420                 425                 430

Gly Thr Pro Tyr Val Arg Ser Arg Ala Trp Glu Gly Asn Gly Lys Tyr
        435                 440                 445

Arg Thr Ala His Phe Asn Thr Thr Ile Gln Phe Lys Gly Asn Val Arg
    450                 455                 460

Asn Leu Arg Ile Lys Leu Val Glu Lys Thr Gly Leu Val Trp Glu Pro
465                 470                 475                 480

Trp Arg Thr Val Tyr Asp Arg Ser Asp Leu Pro Leu Val Arg Gln Arg
                485                 490                 495

Thr Ile Ser Asn Trp Gly Thr Thr Leu Trp Pro Arg Val Ala Glu Thr
            500                 505                 510

Val Lys Asn Asp
        515

<210> SEQ ID NO 12
<211> LENGTH: 426
<212> TYPE: DNA
<213> ORGANISM: Gardnerella vaginalis

<400> SEQUENCE: 12
tacaccactt ccttcgtcaa ggataacgaa gtagcaactt tgcaatccaa cagcgattat      60
attgaaacga aggtttcctc ttaccgcaat ggctacttga ctttggacca ccgtggagct     120
tacgtagctc gctactacat ctactgggat gagtacggca ccgaaattga cggcactcct     180
tacgtgcgtt ctcgcgcttg ggaaggcaat ggtaagtatc gtacagctca cttcaatacc     240
actattcagt tcaaaggaaa tgtacgcaat ctacgaatca agttggttga aaagactggt     300
ttagtttggg aaccatggcg cacagtatat gaccgttctg atttgccact agttcatcag     360
cgtactatta gcaactgggg cacaaccttg tggcctcgcg ttgctgaaac tgtaaagaac     420
gactga                                                                426

<210> SEQ ID NO 13
<211> LENGTH: 141
<212> TYPE: PRT
<213> ORGANISM: Gardnerella vaginalis

<400> SEQUENCE: 13

Tyr Thr Thr Ser Phe Val Lys Asp Asn Glu Val Ala Thr Leu Gln Ser
1               5                   10                  15

Asn Ser Asp Tyr Ile Glu Thr Lys Val Ser Ser Tyr Arg Asn Gly Tyr
            20                  25                  30

-continued

```
Leu Thr Leu Asp His Arg Gly Ala Tyr Val Ala Arg Tyr Ile Tyr
         35                  40                  45

Trp Asp Glu Tyr Gly Thr Glu Ile Asp Gly Thr Pro Tyr Val Arg Ser
 50                  55                  60

Arg Ala Trp Glu Gly Asn Gly Lys Tyr Arg Thr Ala His Phe Asn Thr
 65                  70                  75                  80

Thr Ile Gln Phe Lys Gly Asn Val Arg Asn Leu Arg Ile Lys Leu Val
                 85                  90                  95

Glu Lys Thr Gly Leu Val Trp Glu Pro Trp Arg Thr Val Tyr Asp Arg
                100                 105                 110

Ser Asp Leu Pro Leu Val His Gln Arg Thr Ile Ser Asn Trp Gly Thr
            115                 120                 125

Thr Leu Trp Pro Arg Val Ala Glu Thr Val Lys Asn Asp
        130                 135                 140

<210> SEQ ID NO 14
<211> LENGTH: 33
<212> TYPE: DNA
<213> ORGANISM: Gardnerella vaginalis

<400> SEQUENCE: 14
gaaaagactg gtttagtttg ggaaccatgg cgc                               33

<210> SEQ ID NO 15
<211> LENGTH: 11
<212> TYPE: PRT
<213> ORGANISM: Artificial Sequence
<220> FEATURE:
<223> OTHER INFORMATION: Synthetic peptide

<400> SEQUENCE: 15

Gly Ala Thr Gly Leu Ala Trp Glu Pro Trp Arg
 1               5                  10

<210> SEQ ID NO 16
<211> LENGTH: 11
<212> TYPE: PRT
<213> ORGANISM: Artificial Sequence
<220> FEATURE:
<223> OTHER INFORMATION: Synthetic peptide

<400> SEQUENCE: 16

Glu Ala Thr Gly Leu Ala Trp Asp Pro Trp Trp
 1               5                  10

<210> SEQ ID NO 17
<211> LENGTH: 11
<212> TYPE: PRT
<213> ORGANISM: Artificial Sequence
<220> FEATURE:
<223> OTHER INFORMATION: Synthetic peptide

<400> SEQUENCE: 17

Glu Cys Thr Gly Leu Phe Trp Glu Trp Trp Arg
 1               5                  10

<210> SEQ ID NO 18
<211> LENGTH: 11
<212> TYPE: PRT
<213> ORGANISM: Artificial Sequence
<220> FEATURE:
<223> OTHER INFORMATION: Synthetic peptide

<400> SEQUENCE: 18
```

Glu Cys Thr Gly Leu Ala Trp Glu Trp Trp Arg
1               5                   10

<210> SEQ ID NO 19
<211> LENGTH: 21
<212> TYPE: DNA
<213> ORGANISM: Artificial Sequence
<220> FEATURE:
<223> OTHER INFORMATION: Synthetic primer

<400> SEQUENCE: 19
atgcagcgaa gcatgccatg c                                    21

<210> SEQ ID NO 20
<211> LENGTH: 21
<212> TYPE: DNA
<213> ORGANISM: Artificial Sequence
<220> FEATURE:
<223> OTHER INFORMATION: Synthetic primer

<400> SEQUENCE: 20
tcagtcgttc tttacagttt c                                    21

<210> SEQ ID NO 21
<211> LENGTH: 27
<212> TYPE: DNA
<213> ORGANISM: Artificial Sequence
<220> FEATURE:
<223> OTHER INFORMATION: Synthetic primer

<400> SEQUENCE: 21
gccgccgccc atatgaagag tacaaag                              27

<210> SEQ ID NO 22
<211> LENGTH: 27
<212> TYPE: DNA
<213> ORGANISM: Artificial Sequence
<220> FEATURE:
<223> OTHER INFORMATION: Synthetic primer

<400> SEQUENCE: 22
gccggatcct cagtcgttct ttacagt                              27

<210> SEQ ID NO 23
<211> LENGTH: 47
<212> TYPE: DNA
<213> ORGANISM: Artificial Sequence
<220> FEATURE:
<223> OTHER INFORMATION: Synthetic primer

<400> SEQUENCE: 23
tggttgaaaa gactggtttg gtttgggaat ggtggcgcac agtatat        47

<210> SEQ ID NO 24
<211> LENGTH: 47
<212> TYPE: DNA
<213> ORGANISM: Artificial Sequence
<220> FEATURE:
<223> OTHER INFORMATION: Synthetic primer

<400> SEQUENCE: 24
atatactgtg cgccaccatt cccaaaccaa accagtcttt tcaacca        47

<210> SEQ ID NO 25
<211> LENGTH: 33

<210> SEQ ID NO 25
<211> LENGTH: 33
<212> TYPE: DNA
<213> ORGANISM: Artificial Sequence
<220> FEATURE:
<223> OTHER INFORMATION: Synthetic primer

<400> SEQUENCE: 25
gccgcccata tgtcgttgaa taattatttg tgg                                33

<210> SEQ ID NO 26
<211> LENGTH: 26
<212> TYPE: DNA
<213> ORGANISM: Artificial Sequence
<220> FEATURE:
<223> OTHER INFORMATION: Synthetic primer

<400> SEQUENCE: 26
ggaattccat atggcaaata aagcag                                        26

<210> SEQ ID NO 27
<211> LENGTH: 27
<212> TYPE: DNA
<213> ORGANISM: Artificial Sequence
<220> FEATURE:
<223> OTHER INFORMATION: Synthetic primer

<400> SEQUENCE: 27
ccgctcgagg tcattttcta ccttatc                                       27

<210> SEQ ID NO 28
<211> LENGTH: 30
<212> TYPE: DNA
<213> ORGANISM: Artificial Sequence
<220> FEATURE:
<223> OTHER INFORMATION: Synthetic primer

<400> SEQUENCE: 28
accgggcttg cctgggaacc gtggcgtacg                                    30

<210> SEQ ID NO 29
<211> LENGTH: 30
<212> TYPE: DNA
<213> ORGANISM: Artificial Sequence
<220> FEATURE:
<223> OTHER INFORMATION: Synthetic primer

<400> SEQUENCE: 29
cgtacgccac ggttcccagg caagcccggt                                    30

<210> SEQ ID NO 30
<211> LENGTH: 34
<212> TYPE: DNA
<213> ORGANISM: Artificial Sequence
<220> FEATURE:
<223> OTHER INFORMATION: Synthetic primer

<400> SEQUENCE: 30
gccgccctcg agccaccaat gggaatccaa ggag                               34

<210> SEQ ID NO 31
<211> LENGTH: 33
<212> TYPE: DNA
<213> ORGANISM: Artificial Sequence
<220> FEATURE:
<223> OTHER INFORMATION: Synthetic primer

<400> SEQUENCE: 31

```
gccgccgaat tcttagggat gaaggctcca ggc                                    33

<210> SEQ ID NO 32
<211> LENGTH: 21
<212> TYPE: DNA
<213> ORGANISM: Artificial Sequence
<220> FEATURE:
<223> OTHER INFORMATION: Synthetic primer

<400> SEQUENCE: 32
tactccaaac ctttccaacc c                                                 21

<210> SEQ ID NO 33
<211> LENGTH: 20
<212> TYPE: DNA
<213> ORGANISM: Artificial Sequence
<220> FEATURE:
<223> OTHER INFORMATION: Synthetic primer

<400> SEQUENCE: 33
aacttctcca caaccctctg                                                   20

<210> SEQ ID NO 34
<211> LENGTH: 22
<212> TYPE: DNA
<213> ORGANISM: Artificial Sequence
<220> FEATURE:
<223> OTHER INFORMATION: Synthetic primer

<400> SEQUENCE: 34
gggcgcctgg tcaccagggc tg                                                22

<210> SEQ ID NO 35
<211> LENGTH: 21
<212> TYPE: DNA
<213> ORGANISM: Artificial Sequence
<220> FEATURE:
<223> OTHER INFORMATION: Synthetic primer

<400> SEQUENCE: 35
ggggccatcc acagtcttct g                                                 21
```

TREATMENT AND PREVENTION OF *GARDNERELLA VAGINALIS* INFECTIONS

CROSS-REFERENCE TO RELATED APPLICATIONS

This present application is a national stage application of PCT Application No. PCT/US2009/037328, filed Mar. 16, 2009 and claims priority of U.S. Provisional Application. No. 61/036,943 filed Mar. 15, 2008 and U.S. Provisional Application. No. 61/057,190 filed May 29, 2008, the entire contents of which are hereby incorporated by reference as if fully set forth herein, under 35 U.S.C. §119(e).

STATEMENT OF GOVERNMENTAL INTEREST

This invention was made with government support under National Institutes of Health Grant AI065450. The government has certain rights in the invention.

BACKGROUND OF THE INVENTION

1. Field of the Invention

The present invention relates to the discovery of the nucleic acid sequence and amino acid sequence encoding a newly identified *G. vaginalis* pore-forming toxin called vaginolysin (VLY), and to methods for diagnosing, preventing and treating *G. vaginalis* and bacterial vaginosis (BV). Other aspects are related to vaccines that include a toxoid form of VLY as an immunogen.

2. Description of the Related Art

Bacterial vaginosis (BV) is the most common vaginal infection worldwide and is associated with significant adverse consequences including and preterm labor and delivery (40, 41), post-partum endometritis, (42) and an increased risk of HIV acquisition. (43-45) Reported prevalence rates range from 10-40% depending upon the population studied. (46) However, suboptimal methods of diagnosis and a high percentage of asymptomatic patients make the true prevalence of BV difficult to ascertain. *Gardnerella vaginalis* is a bacterial species associated with bacterial vaginosis (BV).

The pathogenesis of BV remains poorly understood. It is most commonly defined as a pathological state characterized by the loss of normal vaginal flora, particularly *Lactobacillus* species, and overgrowth of other microbes including *Gardnerella vaginalis, Bactericides* species, *Mobiluncus* species, and *Mycoplasma hominis*. Recent data however, suggest a primary role for *G. vaginalis* as a specific and sexually transmitted etiological agent in BV, as was initially postulated by Gardner and Dukes in 1955. (47-49)

Alterations of both local host immunity and the genital tract microflora appear to contribute to the pathogenesis of BV (39), which can be difficult to eradicate even using targeted antimicrobial therapy (4). In addition, randomized trials of antibiotics for the prevention of BV-associated preterm birth have not shown consistently beneficial effects, suggesting that host inflammatory responses set in motion early in the course of disease may contribute significantly to the consequences of infection (26, 27).

In the 1950s, Leopold (25) and then Gardner and Dukes (14) observed abundant small, pleomorphic gram-variable rods in the genital tract of women with BV. This organism, first called *Haemophilus vaginalis* (13) and repeatedly renamed as more information about its characteristics became available (reviewed in (5)), is now classified as *Gardnerella vaginalis*, the sole member of the genus *Gardnerella* (16, 30). Phylogenetic analysis based on 16S rRNA places *Gardnerella* in the gram-positive family Bifidobacteriales. An abundance of *G. vaginalis* and a paucity of *Lactobacillus* species are characteristic of a BV-associated microflora, but the relative contribution of *G. vaginalis* to the pathogenesis of BV is not clear. *G. vaginalis* is present in essentially all cases of BV but can also be detected in a minority of asymptomatic women (1). Likewise, several groups have demonstrated that the vaginal microflora is exceedingly complex in BV where the vaginal mucosa is host to many non-*Gardnerella* organisms (12, 18, 20). Mechanistic studies of BV and its adverse consequences have been limited by the absence of definitive diagnostic testing and a suitable animal model (22, 23, 26). Existing methods of diagnosis for BV are suboptimal and frequently underutilized by practitioners. A recent study by Hogan et al. reports that the prevalence of BV among pregnant women varies greatly depending on the diagnostic criteria used. (51) Established in 1983, Amsel's criteria are widely accepted as the best available means for diagnosing BV in the clinical setting, however, these criteria are complex, somewhat subjective, and necessitate that microscopy equipment be present on site. (52, 53) The Nugent scoring system for interpretation of Gram-stained vaginal smears was put forth in an attempt to standardize diagnosis of BV and increase inter-rater reliability. (54) While the Nugent scoring system exhibits superior sensitivity and specificity compared to the Amsel criteria, (55) its use remains largely restricted to research protocols. Furthermore, questions regarding the risk of potential morbidities and the need for antimicrobial therapy in those women found to have "intermediate flora" remain unanswered. (56, 57)

Several alternative diagnostic methodologies focusing upon the detection of microbial virulence factors produced by the various BV-associated organisms have been proposed in recent years. These include detection of bacterial sialidases, determination of amine levels, and measurement of proline aminopeptidase activity. (58-60) While these techniques are relatively simple, rapid and inexpensive, they fail to identify the specific microbial pathogens present. A potential role for novel, molecular-based techniques for diagnosing BV has recently emerged. Importantly, preliminary studies evaluating these PCR-based strategies have provided additional evidence for *G. vaginalis* as the primary etiologic agent of BV. (61-63) Menard et al. analyzed 213 vaginal samples from pregnant women using molecular probes targeting 8 BV-related organisms. (64) These authors report that an increased load of *G. vaginalis* (>$10^9$ copies of *G. vaginalis* DNA per ml) had both high negative and positive predictive values for the diagnosis of BV. While these molecular based diagnostic strategies are promising, the required expertise, laboratory resources and expense limits their use in the primary care setting.

*G. vaginalis* produces a cholesterol-dependent cytolysin (CDC) (protein pore-forming toxin) called vaginolysin ("VLY"), that acts as a hemolysin (8, 35, 50). IgA-mediated immune responses to the hemolysin occur during BV and are useful as a marker of disease (8, 35). However, complete characterization of the VLY has been limited by the absence of genetic information and an inability to produce recombinant toxin. Therefore there is a great need to sequence and characterize the human-specific VLY toxin, and for methods for treating or preventing *G. vaginalis* and BV.

The global impact of the HIV epidemic cannot be overstated. Even as antiretroviral drugs prolong and improve life for HIV-infected people in wealthy nations, millions of people suffer and ultimately perish from the ravages of the disease worldwide. Despite this, and despite decades of research, prevention and cure of HIV remain elusive goals.

Thus, there is a need for novel and creative approaches to preventing HIV acquisition. BV is exceedingly common, especially in Africa where more than 50% of women in numerous trials, including the recent trial of acyclovir for HSV suppression in Tanzania 1) were infected with BV. BV has been repeatedly associated with both increased risk of HIV acquisition and increased viral shedding among those already infected with HIV2. In vitro, treatment of HIV-infected cells with *Gardnerella* leads to increased production of viral transcripts. Comparatively little attention has been paid to targeting BV as a means of affecting the progression of the HIV epidemic due to several factors: (1) BV is not a "traditional" sexually transmitted infection (STI) and is often omitted from analyses of STI-HIV interactions; (2) *Gardnerella* is enigmatic: difficult to culture, without an available genome sequence, lacking known virulence factors, and (perhaps most importantly) without an animal model; (3) BV and *Gardnerella* colonization are extremely difficult to eradicate even with targeted antibiotic therapy. A randomized, controlled trial of mass antibiotic treatment targeting STI in Uganda did not affect the prevalence of BV in either the control or the treatment group, emphasizing the challenges of BV prevention and treatment (and failing to address the impact of an efficacious BV therapy) (4).

Therefore there is a great need for a new methods and compositions to *G. vaginalis* and BV to minimize the risk of transmitting HIV from person to person, particularly from an HIV-positive mother who has *G. vaginalis* to a fetus or an infant during delivery.

BRIEF DESCRIPTION OF THE DRAWINGS

The present invention is illustrated by way of example, and not by way of limitation, in the FIGs.

FIG. 1 Phylogenetic relationship between VLY and other members of the cholesterol-dependent cytolysin (CDC) family. (A) Phylogram of full-length CDC protein sequences predicted by the neighbor joining algorithm. Numbers represent calculated relative phylogenetic distances. (B) Multiple alignments (SEQ ID NOS: 7, 15, 16, 17 and 18, respectively) of undecapeptide regions from known CDC. The predicted amino acid sequence of VLY contains a variant undecapeptide region most similar to the undecapeptide from intermedilysin (ILY). The sequence labeled "consensus" corresponds to the undecapeptide from MLY, PLY, SUI, IVN, ALV, SPH, THU, SLO, ALO, LLO, PFO, CER, and TET. (C) Western blot of lysed *G. vaginalis* bacteria (*G. vaginalis*) and purified, recombinant VLY, probed with anti-PLY monoclonal antibody. Abbreviations for CDC proteins: PLY, pneumolysin; LLO, listeriolysin O; IVN, ivanolysin; SLG, seeligeriolysin; SPH, sphaericolysin; ALO, anthrolysin O; CER, cereolysin; PFO, perfringolysin O; ALV, alveolysin; TET, tetanolysin O; PYO, pyolysin; MLY, mitilysin; SLO, streptolysin O; SUI, suilysin; THU, thuringensolysin.

SUMMARY OF THE INVENTION

Figure 2A:
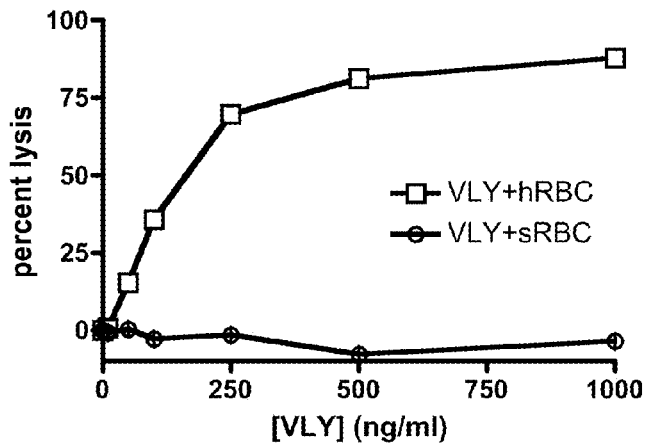
FIG. 2 Human-specific, cholesterol-dependent hemolytic activity of vaginolysin (VLY). (A) Washed human (hRBC) or sheep (sRBC) erythrocytes (1% solution in PBS) were exposed to the indicated concentrations of purified recombinant VLY for 30 min, followed by pelleting of cells. Hemoglobin release was measured by $OD_{415}$ of the supernatant and normalized to 100% lysis for each species tested (P<0.01, ANOVA). (B) Erythrocytes from various species were exposed to VLY or the non-species-specific toxin pneumolysin (PLY) (both toxins at 5 µg/ml) and lysis measured. (C) Addition of cholesterol (Ch) at 1 µg/ml or 10 µg/ml inhibits human erythrocyte lysis by VLY (5 µg/ml) (P<0.001, ANOVA).

Certain embodiments of the present invention are directed to an isolated nucleic acid encoding VLY toxin protein from *G. vaginalis*, identified as the nucleotide sequence SEQ ID No: 1 from strains 14018 or 14019, SEQ ID NO: 3 from strain 49145, or SEQ ID NO: 10 from strain ARG3, and degenerate variants or fragments thereof. Other embodiments are directed to an isolated nucleic acid encoding domain 4 of VLY from *G. vaginalis*, identified as nucleotide sequence of SEQ ID No: 4 from strains 14018 or 14019 or SEQ ID NO: 12 from strain 49145, and degenerate variants or fragments thereof. Other embodiments are directed to an isolated nucleic acid encoding the undecapeptide of VLY from *G. vaginalis*, identified as nucleotide sequence of SEQ ID No: 6, from strains 14018 or 14019 or SEQ ID NO: 14 from strain 49145, and degenerate variants or fragments thereof.

Other embodiments are directed to isolated and purified VLY protein from *G. vaginalis*, identified by the amino acid sequence set forth in SEQ ID NO: 2 from strains 14018 and 14019 and SEQ ID NO: 11 from strain ARG3, and biologically active fragments or variants thereof. Other embodiments are directed to the isolated and purified conserved undecapeptide region of VLY of *G. vaginalis*, the amino acid sequence (EKTGLVWEPWR) of which is set forth as SEQ ID NO: 7, or a biologically active fragment or variant thereof, and the undecapeptide region for toxoid 480P (EKTGLVWEWWR) set forth in SEQ ID NO: 8. Also claimed are isolated and purified domain 4 peptides of VLY of *G. vaginalis*, the amino acid sequences of which are set forth in SEQ ID NO: 5 from strains 14018 and 14019, or SEQ ID NO: 13 from strain 49145, and biologically active fragments or variants thereof. Another embodiment is directed to isolated and purified immunogenic *G. vaginalis* VLY polypeptide fragments, that include at least ten consecutive amino acid residues of SEQ ID NO: 2 from strains 14018 or 14019, and SEQ ID NO: 3 from strain 49145, and variants thereof.

Other embodiments are directed to various isolated and purified pore-forming toxoids of VLY from *G. vaginalis*, as defined herein, and to their use in a VLY vaccine.

Other embodiments are directed to a method for diagnosing and treating a *G. vaginalis* infection or bacterial vaginosis in a patient, the steps of which include a.) obtaining a biological sample from the patient, b.) detecting the presence of VLY protein having the amino acid sequence set forth in SEQ ID NO: 2 or SEQ ID NO: 3, or a biologically active fragment or variant thereof in the biological sample taken from the patient, and c.) if the VLY protein is detected then administering to the patient a therapeutically effective amount of an antibiotic known to treat *G. vaginalis* or a protective agent that is a member selected from the group comprising anti-VLY antibody, anti-PLY antibody, anti-CD59 antibody, anti-pneumolysin antibody, soluble CD59, *G. vaginalis* VLY toxoid, or a biologically active fragment or variant thereof.

Other embodiments are directed to methods for treating or preventing a *G. vaginalis* infection or bacterial vaginosis in a patient, by administering to the patient a therapeutically effective amount of a protective agent that is a member selected from the group comprising anti-VLY antibodies including newly discovered rabbit polyAnti-VLY, anti-PLY antibodies, anti-CD59 antibodies, anti-pneumolysin antibodies, soluble CD59, *G. vaginalis* VLY toxoid, or biologically active fragments or variants thereof.

Other embodiments are directed to compositions for therapeutic use that include anti-VLY antibodies, preferably poly-Anti-VLY, and to compositions that include two compounds selected from the group comprising soluble CD59, anti CD59, anti-VLY, anti-PLY or anti-pneumolysin monoclonal or polyclonal antibodies or immunologically active fragments or variants thereof including polyAnti-VLY, VLY toxoids or immunologically active fragments or variants thereof, and antibiotics known to treat bacterial vaginosis or *G. vaginalis*.

Other embodiments are directed to an ELISA kit for diagnosing *G. vaginalis* infection in a patient, comprising a detection antibody that specifically binds to VLY protein identified by SEQ ID NO: 2 or SEQ ID NO: 11, or a biologically active fragment thereof, including a kit wherein the detection antibody is rabbit polyAnti-VLY. In some embodiments the detection antibody is covalently bound to an enzyme. The kit optionally provides a substrate for the enzyme. Other embodiments are directed to an ELISA kit that also contains a secondary antibody covalently bound to an enzyme, which secondary antibody specifically binds to the detection antibody, and a substrate for the enzyme. Still other embodiments are directed to an Elisa kit including a capture molecule that specifically binds to VLY, including soluble CD59, anti-VLY antibody, anti-PLY antibody, and anti-pneumolysin.

Other embodiments are directed to methods for reducing or preventing the transmission of HIV to another human by a woman infected with HIV and bacterial vaginosis, by administering to the woman before the woman engages in a sexual activity, a therapeutically effective amount of a composition comprising a protective agent selected from the group comprising soluble CD59, anti CD59 or anti-VLY, anti-PLY, poly-AntiPLY, or anti-pneumolysin monoclonal or polyclonal antibodies, VLY toxoids or biologically active fragments or variants thereof. Other embodiments are directed to methods of reducing or preventing maternal to fetal transmission of HIV from a pregnant woman diagnosed as being infected with both HIV and bacterial vaginosis, by administering to the woman prior to a vaginal birth of a fetus, a therapeutically effective amount of a protective agent selected from the group comprising soluble CD59, anti CD59 or anti-VLY, anti-PLY, polyAntiPLY, or anti-pneumolysin monoclonal or polyclonal antibodies, VLY toxoids or fragments or variants thereof.

Another embodiment is directed to the polyclonal rabbit anti-VLY antibody poly-Anti-VLY, or an immunologically active fragment or variant thereof, ant to compositions that include this antibody.

DEFINITIONS

By "protein" or "polypeptide" is meant any chain of amino acids, regardless of length or post-translational modification (e.g., glycosylation or phosphorylation).

A "pure polypeptide" refers to a polypeptide substantially free from naturally associated molecules, i.e., it is at least 75% (e.g., at least 80, 85, 90, or 95; or 100%) pure by dry weight. Purity can be measured by any appropriate standard method, for example, by column chromatography, polyacrylamide gel electrophoresis, or HPLC analysis.

"Peptide variants" and "peptide modifications" are used synonymously here and mean polypeptides that may contain one or more substitutions, additions, deletions and/or insertions such that the therapeutic and antigenic properties of the peptide encoded by the variant are not substantially diminished, relative to the corresponding peptide such as VLY. Such modifications may be readily introduced using standard mutagenesis techniques, such as oligonucleotide directed site-specific mutagenesis. Variants also include what are sometimes referred to as "fragments." Peptide variants may contain one or more amino acid substitutions, additions, deletions and/or insertions. When VLY toxin and toxoids are discussed in the context of expression, activity, immunogenicity or binding to receptors on target cells, the terms include biologically active fragments and variants thereof. The amino acids used to make peptides and variants include synthetic amino acids known in the art.

As used herein, the term VLY means wild type vaginolysin ("VLY") polypeptide that is the human-specific CDC from *G. vaginalis*. VLY is the only known species-specific factor of *G.*

*vaginalis*. VLY is encoded by DNA SEQ ID NO. 1 in *G. vaginalis* 14018 and 14019; and by DNA SEQ ID NO. 3 in strain 49145. The amino acid sequence of VLY is set forth in SEQ ID NO. 2. As used herein VLY includes biologically active fragments and peptide variants thereof, whether naturally-occurring mutants or man-made mutants.

As used herein, the term VLY toxoid means VLY protein that has reduced pore-forming activity compared to wild type VLY due to the presence of one or more amino acid substitutions, but that retains enough immunologic activity to elicit an immune response in an animal.

Unless otherwise indicated, a "therapeutically effective amount" of a compound is an amount that provides a therapeutic benefit in the treatment or management of a disease or condition such as Bacterial vaginosa (BV) or *G. vaginalis*, delays or minimizes one or more symptoms associated with the disease or condition, or enhances the therapeutic efficacy of another therapeutic agent. An agent is said to be administered in a "therapeutically effective amount" if the amount administered results in a desired change in the physiology of a recipient mammal, (e.g. decreases one or more symptoms of the BV or *G. vaginalis*, or decreases the amount of *G. vaginalis* in a biological sample taken from the patient to a level that is at least about 10% less than the level before drug treatment.) A therapeutically effective amount for reducing the risk of transmitting HIV from a *G. vaginalis*-infected woman to a sexual partner or a baby during birth, is an amount that reduces or eliminates viral shedding from HIV-infected cells or that reduces or eliminates the viral load in a biological sample taken from the vagina/birth canal.

Nucleic acids in the context of this invention include "oligonucleotides", which refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

An "isolated nucleic acid" is a nucleic acid the structure of which is not identical to that of any naturally occurring nucleic acid or to that of any fragment of a naturally occurring genomic nucleic acid. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein.

As used herein, protective agents are agents that block or reduce the toxic biological activity of VLY. They include agents that bind to or associate with VLY at a site that interferes with the ability of VLY to bind to CD59 receptor on a target host cell, or otherwise reduce the ability of VLY to cause pores in target cells, or reduce the ability of VLY to increase shedding in HIV-infected cells, or reduce *G. vaginalis* infections or BV. Protective agents include soluble CD59 or fragments or variants thereof that are capable of neutralizing VLY; polyclonal and monoclonal antibodies to CD59, PLY, VLY, pneumolysin, and immunologic fragments or variants thereof, and VLY toxoids that can compete with the more toxic VLY for binding to CD59. Also included is newly discovered polyAnti-VLY and antibiotics that are known to treat bacterial vaginosis and *G. vaginalis* infections.

DETAILED DESCRIPTION

In the following description, for the purposes of explanation, numerous specific details are set forth in order to provide a thorough understanding of the present invention. It will be apparent, however, to one skilled in the art that the present invention may be practiced without these specific details.

Bacterial vaginosis, a chronic infectious/inflammatory disease associated with preterm birth, is strongly linked with the mucosal overgrowth of *G. vaginalis* and its attachment to epithelial cells. To summarize, we have cloned, sequenced, characterized, isolated and purified the human-specific cholesterol-dependent cytolysin (CDC) pore-forming toxin vaginolysin ("VLY") from several human strains of *G. vaginalis* (14018, 14019, 49145, and ARG3). VLY, the only known species-specific factor for *G. vaginalis*, is most closely related to intermedilysin (ILY) from *Streptococcus intermedius*. (15, 29). We have kept the name "vaginolysin" (VLY) for consistency with CDC nomenclature.

VLY lyses target cells in a species-specific manner that is dependent upon the complement regulatory molecule CD59. In addition to causing erythrocyte lysis, VLY activates the conserved epithelial p38 mitogen-activated protein kinase pathway and induces interleukin-8 production by human epithelial cells. Transfection of human CD59 into non-susceptible cells rendered them sensitive to VLY-mediated lysis. In addition, single amino acid substitutions in VLY (including some in the undecapeptide region such as (VLY(P480W)) generated toxoids that did not form pores. Introduction of the analogous proline residue into another CDC, pneumolysin, significantly decreased its cytolytic activity.

Certain embodiments of the present invention are directed to (1) isolated nucleic acid encoding VLY protein or a degenerate variant or fragment thereof from various strains of *G. vaginalis*, and to isolated and purified VLY protein, or a biologically active fragment or variant thereof, (2) an isolated and purified nucleic acid encoding domain 4 or a degenerate variant or fragment thereof from various strains of *G. vaginalis*, and to isolated and purified domain 4 region of VLY, or a biologically active fragment or variant thereof, and (3) an isolated and purified nucleic acid encoding the undecapeptide or a degenerate variant or fragment thereof from various strains of *G. vaginalis*, and the isolated and purified undecapeptide region of VLY, or a biologically active fragment or variant thereof. So far we have found that the undecapeptide region is conserved.

Certain other embodiments are directed methods for diagnosing *G. vaginalis* infection by detecting the presence of VLY protein in a biological sample, preferably using a new ELISA with detection antibodies to VLY.

Certain other embodiments are directed to various newly discovered toxoid forms of human VLY protein or an immunogenic fragment or variant thereof that has reduced pore-forming activity compared to wild-type VLY. Another embodiment is directed to a composition comprising one or more purified VLY toxoid proteins, and to a method of eliciting an immune response in an animal by introducing this toxoid composition into the animal. Other compositions of the present invention include a vaccine comprising one or more VLY toxoids.

Other embodiments include a method for permeabilizing a cell membrane (such as a cancer cell) to kill the cell or (in the case of cancer) render it more accessible to chemotherapeutic agents, comprising contacting the cell with a composition that includes purified VLY protein or a biologically active fragment or variant thereof. Another embodiment is directed to VLY toxin that is bound to a molecule that is targeted specifically to the cancer cell or VLY toxin that is bound to a chemotherapeutic agent.

We have discovered that VLY binds to CD59 receptor on epithelial cells, which enables it to permeabilize the vaginal epithelial cell. Therefore certain embodiments are directed to methods for treating or preventing G. vaginalis and bacterial vaginosis by administering one or more protective agents (including soluble CD59 itself, and/or Anti CD59 monoclonal or polyclonal antibodies, small molecules or anti-VLY and anti-PLY antibodies), that prevent VLY from binding to its CD59 receptor on target cells including vaginal epithelial confirm cells or otherwise block its pore-forming ability.

Using purified VLY toxin as an immunogen, we generated polyclonal rabbit immune serum (IS) having a polyclonal rabbit anti-VLY antibody that we named "polyAnti-VLY." PolyAnti-VLY inhibited VLY-mediated lysis of human cervical carcinoma cells and vaginal epithelial cells therefore polyAnti-VLY has therapeutic use and can be used in an ELISA kit for detecting VLY.

Certain embodiments of the invention are directed to methods that treat BV in order to reduce transmission of HIV from an HIV/BV-infected woman to her sexual partner or to a fetus she may be carrying, or to an infant during childbirth by administering one or more of the described protective agents. The G. vaginalis Genome Contains an Orthologue of Known CDCs The CDC family is made up of more than 15 protein toxins produced by several distinct gram-positive genera (reviewed in (38)). The basic local alignment search tool (BLAST) was used to compare raw genomic DNA sequence data from the Gardnerella vaginalis 14018 genome project (available at http://med.stanford.edu/sgtc/research/gardnerella_vaginalis.html (available at) with a database of known microbial genes (Comprehensive Microbial Resource, J. Craig Venter Institute). We identified a 1551 base pairs (bp) open reading frame with 54% DNA sequence identity to pneumolysin, the S. pneumoniae CDC that we proceeded to analyze. This genomic region was amplified from G. vaginalis 14018 (ATCC) by PCR, cloned, and sequenced. See Example 1. SEQ ID NO: 1 sets forth the DNA sequence encoding VLY protein from G. vaginalis species 14018 and 14019, which are identical. VLY made by G. vaginalis strain 49145 is set forth in SEQ ID NO. 3. Certain embodiments are directed to nucleic acids identified by SEQ ID NO: 1 and 3, or a biologically active fragment or variant thereof. Other embodiments are directed to a vector that includes the DNA SEQ ID NO: 1 or 3 encoding VLY protein from strains 14018 and 14019, or 49145, respectively, or a biologically active fragment or variant thereof.

The predicted amino acid sequence of VLY (from strains 14018 and 14019) set forth in SEQ ID NO. 2, exhibits sequence similarity and identity consistent with reported relationships among members of the CDC family (Appendix). The predicted sequence of VLY from G. vaginalis strain (ATCC 49145) is identical with the exception of a single amino acid substitution (R494H-See SEQ ID NO. 3). Certain embodiments are directed to the isolated and purified (naturally occurring and recombinant) VLY proteins described herein and to biologically active variants and fragments thereof, including those having the amino acid sequences set forth in SEQ ID NO: 2 for VLY from strains 14018-19), and the amino acid sequence set forth in SEQ ID NO: 11 for VLY from ARG3. An embodiment of the invention is directed also to Codon optimized VLY gene sequence (that has the same protein sequence as VLY from strain 14018) DNA SEQ ID NO: 9 which greatly improves yield and purity of recombinant toxin made in E. coli.

The phylogram of CDC protein sequences (FIG. 1A) demonstrates three distinct groupings—a Streptococcus group (into which VLY falls), a Listeria group, and a Bacillus/ Clostridium group (also containing SLO). The members of the Streptococcus clade have the most divergence in the domain 4 undecapeptide, including the presence of a proline residue as an insertion (pyolysin) or substitution (intermedilysin, VLY). In the case of pyolysin, the unusual undecapeptide has been shown to be required for pore formation (3). Seeligeriolysin, the CDC from L. seeligeri, has an alanine to phenylalanine substitution in the undecapeptide that causes a decrease in toxin efficacy compared to listeriolysin 0 (21).

A phylogram of representative full-length CDC sequences (FIG. 1B) obtained from publicly available databases (Appendix) was constructed using the neighbor-joining algorithm. By this analysis, VLY appears to be most closely related to ILY and it falls within a group consisting of most of the CDC from genus Streptococcus, including pneumolysin, mitilysin, and suilysin. Pyolysin, from Arcanobacterium pyogenes (2), is the least similar member of this group. VLY is more distantly related to CDC from the Bacillus, Listeria, and Clostridium genera, as well as streptolysin O from Streptococcus pyogenes, which is divergent from the other streptococcal CDC. Bootstrap analysis indicates a high degree of confidence for the placement of VLY in the streptococcal group (data not shown).

The undecapeptide is an 11 amino acid sequence in domain 4 of the CDCs that is well conserved and of particular importance for host cell interaction and pore formation (38). The nucleic acid sequences encoding the undecapeptide of G. vaginalis are set forth in DNA SEQ ID NO: 6 for strains 14018 and 14019 (nucleic acid residues 1414-1446), and DNA SEQ ID NO: 14 for strain 49145. The VLY undecapeptide is divergent from the CDC consensus sequence at 3 of 11 sites (FIG. 1B), one of which is an alanine to valine substitution. More strikingly, there is a proline substitution at VLY position 480, the site of one of the conserved tryptophan residues that is important for pore formation in other CDC family members (24). The loss of the conserved cysteine residue at the second position of the undecapeptide is seen in two other CDC, ILY and pyolysin, and is consistent with the prior report of insensitivity of the G. vaginalis toxin to reducing agents (35). Western blot analysis of lysed G. vaginalis bacteria demonstrates a ~57 kD band that cross reacts with a monoclonal antibody directed against the S. pneumoniae CDC, pneumolysin.

Purified, recombinant human-specific VLY (from strains 14018 and 14019) identified by amino acid or a fragment or variant thereof, that also comes within the scope of this invention, migrates at a similar molecular weight to natural VLY and is also detected by anti-pneumolysin antibody (FIG. 1C). One embodiment of the invention is directed to treating a G. vaginalis infection by administering anti-pneumolysin antibody and/or anti-VLY antibody, preferably locally in the form of a gel vaginal suppository.

Our results show that domain 4 stretches from the conserved tyrosine at position 376 (amino acid position) to the end of the protein which is 516 amino acids long. Certain embodiments are directed to the corresponding DNA SEQ ID NO: 4 encoding domain 4 that begins at nucleotide 1126 and continues to the end of the DNA molecule for strains 14018-9 and SEQ ID NO: 12 (for strain 49145), and to amino acid sequences of domain 4 as set forth in SEQ ID NO: 5 (for strains 14018-9) and SEQ ID NO: 13 (for strain 49145).

Species-Specific, Cholesterol-Dependent Hemolytic Activity of VLY

Figure 2B:
Figure 2C:
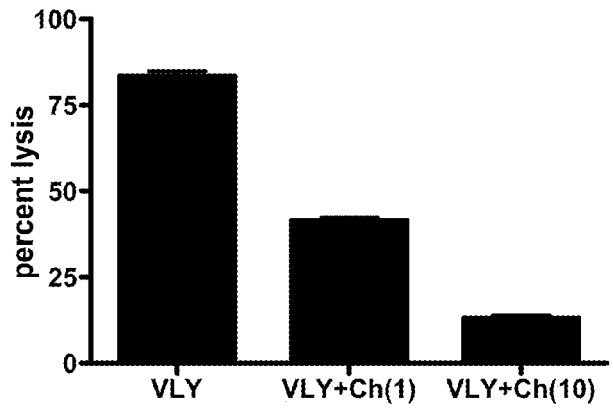

Recombinant VLY produced in E. coli was used for studies of toxin interaction with target cells. Purified recombinant VLY lysed primary human erythrocytes in a dose-dependent fashion (FIG. 2A). In contrast, sheep (FIG. 2A-B), mouse (FIG. 2B) and horse (data not shown) erythrocytes were resistant to lysis even at substantially higher VLY concentrations. Erythrocytes from all of these species were lysed by pneumolysin, a non-species-restricted member of the CDC family (FIG. 2B). Preincubation of VLY with cholesterol inhibited lysis of human erythrocytes in a dose-dependent manner, consistent with its classification within the CDC family (FIG. 2C). Thus VLY is species specific for lysing human cells.

We have also noted profound ultrastructural changes in epithelial cells exposed to sublytic quantities of VLY (about 250 ng/ml) using live-cell imaging of HeLa cells. This response occurred rapidly (<1 min) following exposure of cells to VLY, and blebs remained intact and present over the course of hours prior to resolution. These blebs were contiguous with the epithelial cell cytoplasm, as demonstrated with hCD59-IRES-GFP transfected CHO cells, in which cytoplasmic GFP was observed entering the blebs. Most strikingly, these ultrastructural changes were recapitulated by antibody-mediated cross-linking of the hCD59 receptor and by binding of a non-pore-forming GFP-VLY-D4 fusion protein. These findings are consistent with signaling through hCD59 as a potential mechanism for initiating ultrastructural changes. We hypothesize that this bleb formation represents a novel pathway of toxin recognition by epithelial cells' unique response to hCD59-dependent toxins and involves signaling pathways initiated by hCD59 binding.

VLY Lytic Activity Requires Binding to Complement Regulatory Molecule CD59 on the Surface of Epithelial Cells The human specificity of the G. vaginalis hemolysin was noted in earlier studies (8), but no specific mechanism for this was described. The recent characterization of human CD59 as a receptor for intermedilysin (ILY) represented a major step forward in the understanding of the mechanism of action of CDC, which were previously thought to bind cholesterol directly as the sole requirement for pore-formation. The results presented below show that that this model is oversimplified and that at least a subset of the CDCs including VLY require protein receptors on the surface of target cells (15).

Figure 3A:
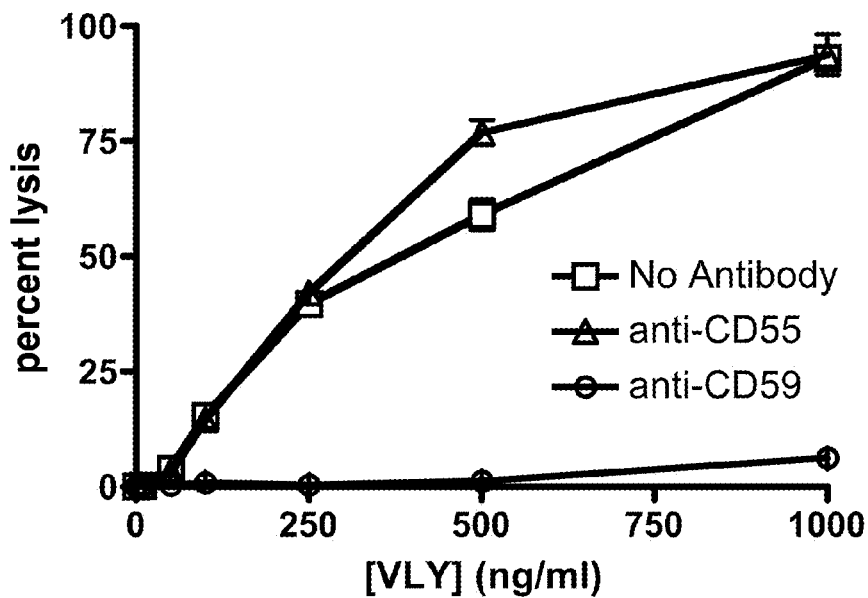
FIG. 3 Host specificity of VLY depends on the complement regulatory molecule CD59. (A) VLY-induced lysis of human erythrocytes was inhibited by monoclonal antibody to human CD59 (P<0.0001) but not antibody to another GPI-anchored cell surface antigen (CD55) or mock treatment (PBS). (B) Antibody to CD59 does not inhibit PLY-mediated lysis of human erythrocytes. (C) LDH release from Chinese hamster ovary (CHO) cells transfected with empty vector (IRES) or human CD59 (IRES-hCD59) and exposed to VLY (10 µg/ml) for 30 min. Transfection of human CD59 increases VLY-mediated lysis (P<0.0001). (D) Transfection of human CD59 into CHO cells does not affect PLY (1 µg/ml)-mediated lysis (P>0.05).

The results in FIG. 3A show that blockade of CD59 on the surface of primary human erythrocytes using monoclonal antibody MEM-43 clone abrogated VLY-induced lysis. By contrast, antibody against another erythrocyte surface marker CD55 was ineffective, anti-CD59 antibodies for use in treating G. vaginalis and bacterial vaginosis infections are commercially available for example from—Santa Cruz Biotechnology and Genetex. Thus surface CD59 on epithelial cells is the receptor for VLY and binding of CD59 by VLY is necessary for lytic activity.

Figure 3B:
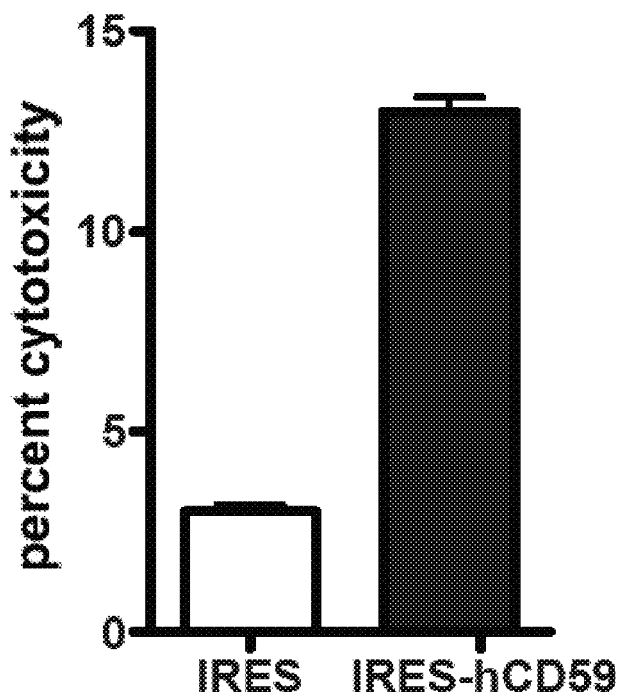
Figure 3C:
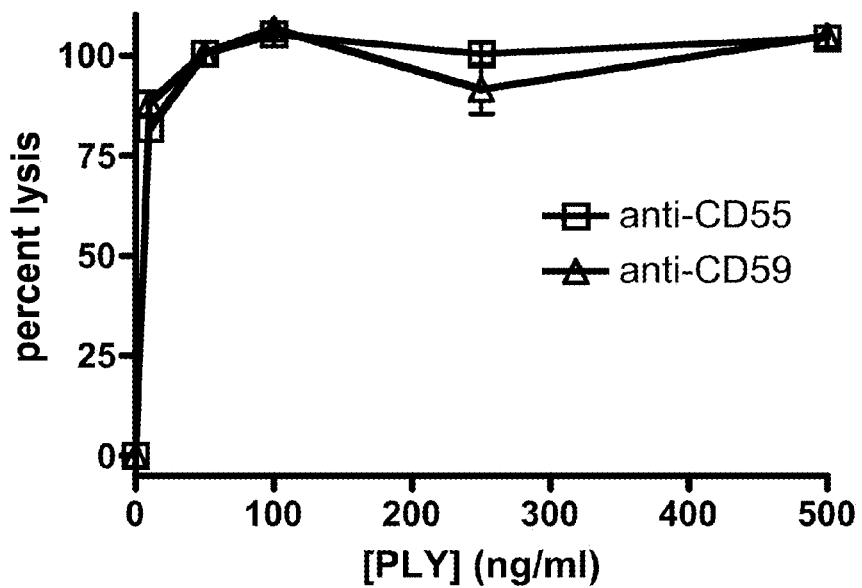
Figure 3D:
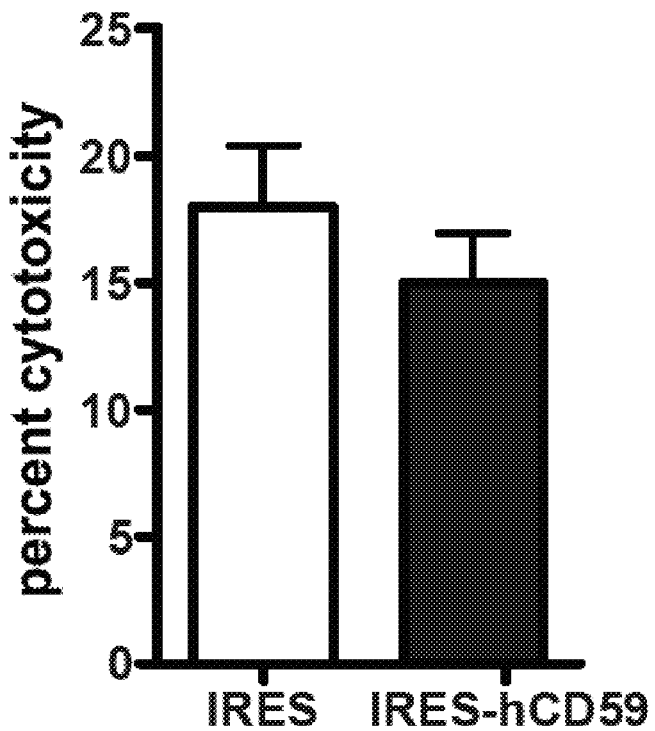

Our results showed that the activity of pneumolysin, a CDC that does not exhibit host specificity, was not inhibited by either anti-CD59 or anti-CD55 (FIG. 3B). However, transfection of human CD59 into Chinese hamster ovary (CHO) cells significantly increased lactate dehydrogenase release in the setting of treatment with VLY (FIG. 3C) but not pneumolysin (FIG. 3D), indicating that CD59 is sufficient to confer susceptibility on at least a subset of VLY resistant cells.

CD59 is expressed on the surface of human genital tract epithelial cells, the target cell type during G. vaginalis colonization and BV, as demonstrated by immunofluorescence staining with monoclonal antibody against hCD59 (MEM-43 clone). Secondary anti-mouse IgG-Alexa Fluor 488 (green) was used. hCD59 has also been shown to be highly expressed in the female genital tract in vivo, along with other complement regulatory molecules (70).

Certain embodiments of the invention are directed to methods for treating G. vaginalis infection by (1) administering soluble CD59 itself (CD59 with the GPI anchor deleted) to saturate or neutralize VLY thereby preventing it from binding to CD59 receptor on vaginal epithelial cells, or (2) administering anti-CD59 or anti-VLY polyclonal or monoclonal antibodies that prevent binding of VLY to the CD59 receptor on vaginal epithelial cells. Monoclonal Anti-CD59 antibodies are commercially available from several sources.

Anti-VLY antibodies can be directed to the VLY protein or to a biologically active fragment or variant thereof, including domain 4 and the undecapeptide regions of VLY. In a preferred embodiment, the therapeutic anti-CD59 and anti-VLY antibodies and CD59 are locally administered, for example as a vaginal suppository. Such local administration is not only efficient requiring fewer antibodies, but it also enables a high concentration of the therapeutic agent to be delivered to the target cells. Since CD59 is ubiquitous and plays an important role protecting cells from damage by complement, it is also important to specifically target CD59 expressed on the surface of the target epithelial cells, and not administer it systemically.

G. vaginalis is a Gram Positive Bacterium

The discovery of the pore-forming toxin VLY in G. vaginalis expands the CDC family to another gram-positive genus and to a novel anatomic site. CDCs are produced by organisms that colonize and cause disease at mucosal surfaces including the upper and lower respiratory tracts and the gastrointestinal tract. In many such cases, toxin production has been shown to be essential for maintenance of colonization, pathogenesis of invasive disease, or both (38). CDCs have been described only in gram-positive organisms. Thus, the characterization of VLY and its evolutionary relationship to the other CDC provides further evidence that G. vaginalis is most properly grouped with the gram-positives, despite its variable staining characteristics (36). Antibiotics that have been used to treat BV and G. vaginalis infections include metronidazole, clindamycin and tinidazole.

Metronidazole is the most successful therapy. Most comparative studies using multiple divided-dose oral regimens for one week achieved early rates of clinical cure in excess of 90 percent, and cure rates (by Amsel criteria) of approximately 80 percent at four weeks. A randomized trial showed that short-term cure rates were significantly higher when the initial course of metronidazole therapy was 14 days rather than 7 days (Schwebke, J R, Desmond, R A. A randomized trial of the duration of therapy with metronidazole plus or minus azithromycin for treatment of symptomatic bacterial vaginosis. Clin Infect Dis 2007; 44:213.). However, long-term cure rates (21 days after completion of therapy) were similar for both treatment regimens. In one embodiment, the oral regimen of tronidazole is 500 mg twice daily for seven days. Sexually Transmitted Diseases Treatment Guidelines, 2006. MMWR Recomm Rep 006. (RR-11); 55:1-95. Topical vaginal therapy with 0.75 percent metronidazole gel (5 g once daily for five days) is as effective as oral metronidazole. The choice of oral versus topical therapy depends upon patient preference.

Clindamycin can be used as a topical vaginal therapy with 2 percent clindamycin cream (5 g of cream containing 100 mg of clindamycin phosphate) as a seven-day regimen. Alternative regimens include oral clindamycin (300 mg twice daily for seven days) or clindamycin ovules (100 mg intravaginally once daily for three days) (Sexually Transmitted Diseases Treatment Guidelines, 2006. MMWR Recomm Rep 2006 (RR-11); 55:1-95; Paavonen, J, Mangioni, C, Martin, M A, Wajszczuk, C P. Vaginal clindamycin and oral metronidazole for bacterial vaginosis: a randomized trial. Obstet Gynecol 2000; 96:256). A one-day or single application of clindamycin as a bioadhesive has also been approved by the FDA (Clindesse). These regimens have not been studied extensively and may have lower efficacy for eradicating BV.

Tinidazole is a second generation nitroimidazole. It has a longer half-life than metronidazole (12 to 14 hours versus 6 to 7 hours) and fewer side effects (Tinidazole (Tindamax)—a new option for treatment of bacterial vaginosis. Med Lett Drugs Ther 2007; 49:73). In one embodiment, 1 g tinidazole is administered orally once daily for five days, as efficacy is slightly higher and side effects are slightly less frequent than with shorter course therapy (tinidazole 2 g orally daily for two days).

Figure 4A:
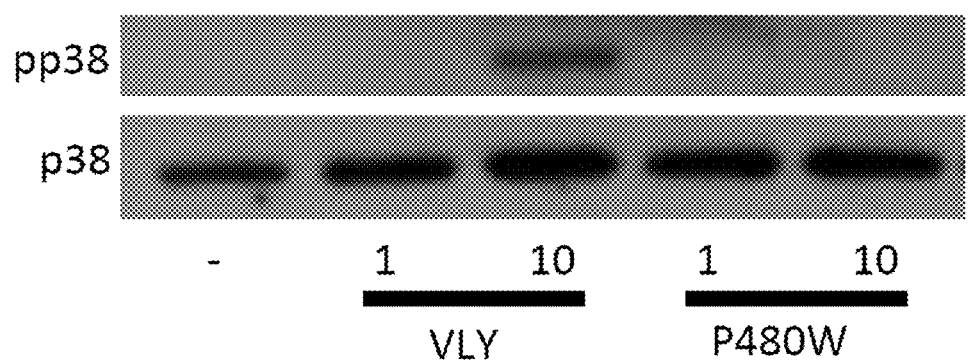
FIG. 4 VLY-mediated epithelial cell activation and erythrocyte lysis require P480. (A) Human cervical epithelial cell line HeLa was treated for 30 min with media alone (−), VLY or VLY (P480W) (1-10 µg/ml) prior to lysis and Western blotting with antibodies specific for total (p38) and phospho-p38 (pp38) MAPK. (B) HeLa cells were treated with VLY or VLY (P480W) (10 µg/ml) for 2 hr prior to RNA extraction and assay of relative quantity of interleukin-8 (IL-8) message by real-time PCR. (C) Human (hRBC) and sheep (sRBC) erythrocytes were treated with the indicated concentrations of VLY or VLY (P480W) and hemolysis assessed as above. (D) Human (hRBC) erythrocytes were treated with the indicated concentrations of pneumolysin (PLY) or PLY (W435P) and hemolysis assessed as above.
Figure 4B:
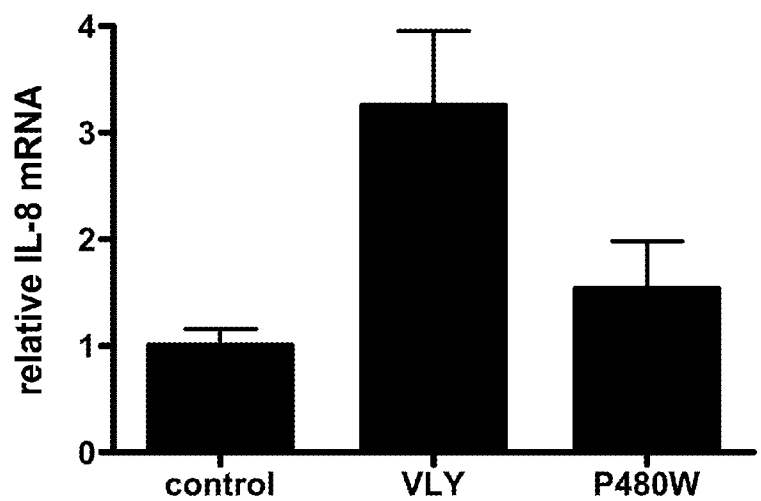

VLY Toxoids: The Proline Residue in the Variant Undecapeptide of VLY (Residue 480) is Required for Cytolytic and Cell Stimulatory Activity Although hemolysis is a useful model for toxin-induced pore formation, erythrocytes are unlikely to be a target cell for G. vaginalis under normal physiologic conditions, as Gardnerella bacteremia is exceedingly rare (11, 33). Activation of p38 mitogen-activated protein kinase (MAPK) is a conserved element in epithelial detection of bacterial pore-forming toxins (32) and appears to be essential in defense of host cells from toxin attack (19). Exposure of the human cervical epithelial cell line HeLa to VLY led to phosphorylation of p38 MAPK within 30 minutes (FIG. 4A), consistent with epithelial responses to other pore-forming toxins (32). FIG. 4B shows that IL-8 mRNA is upregulated in HeLa cells by VLY and is dependent on there being a proline at position 480 in the undecapeptide. The data showing that VLY activates the p38 MAPK and IL-8 pathways in human epithelial cells, shows that VLY produced by G. vaginalis as a major factor in the immunopathology of BV.

Nucleic acid and amino acid sequence alignments are set forth in the Appendix. At the protein level, the undecapeptide is identical G. vaginalis strains 14018 and 14019. DNA sequences encoding VLY are identical for strains 14018 and 14019, and strains 49145 and ARG3 are very close with several single base substitutions (seen in the alignment). For example, there is a single (silent) base pair substitution (G>A at nucleotide position 1428) in 49145 compared to the other two (14018 and 14019). One nucleotide substitution leads to a change in VLY protein sequence (R→H at amino acid position 494) in the 49145 strain. This change is in domain 4 but after the undecapeptide region.

Genetic and structural studies have implicated domain 4 (D4) of the CDC as being crucial for membrane association. Specifically, the undecapeptide appears to have a significant role in CDC function. Because of the importance of the undecapeptide to toxin function, we created a mutant named VLY (P480W) using site-directed mutagenesis to make a single amino acid substitution of tryptophan was for proline at position 480. This change converted the proline residue in the VLY undecapeptide to the consensus tryptophan residue, which has been shown to be crucial to the function of several other CDC that contain the consensus undecapeptide.

Figure 4C:
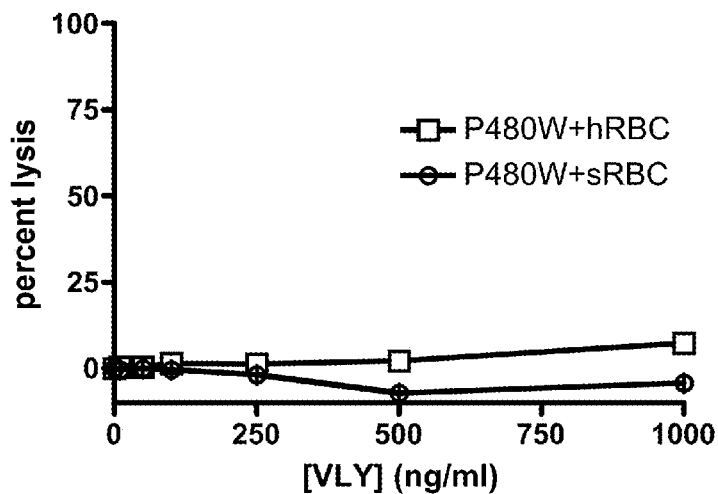

Notably, the P480W mutation produced a VLY toxoid that was substantially less effective at lysing human erythrocytes (FIG. 4C). In addition, this proline to tryptophan mutation abolished p38 activation and IL-8 transcription in HeLa cells (FIG. 4A-B) compared to wild-type VLY (FIG. 4A-B). This proline residue does not dictate species-specificity but appears to be crucial for toxin function. These findings underscore the importance of D4, and specifically the undecapeptide, to CDC function, even among the hCD59-dependent CDCs. These results confirm that proline at amino acid residue 480 of VLY is necessary for efficient pore-formation and cell activation by VLY. Because the P480W toxoid is significantly less toxic (lytic activity is reduced) than native VLY toxin, it can be used in vaccines that elicit a specific immune response to VLY toxin.

Figure 4D:
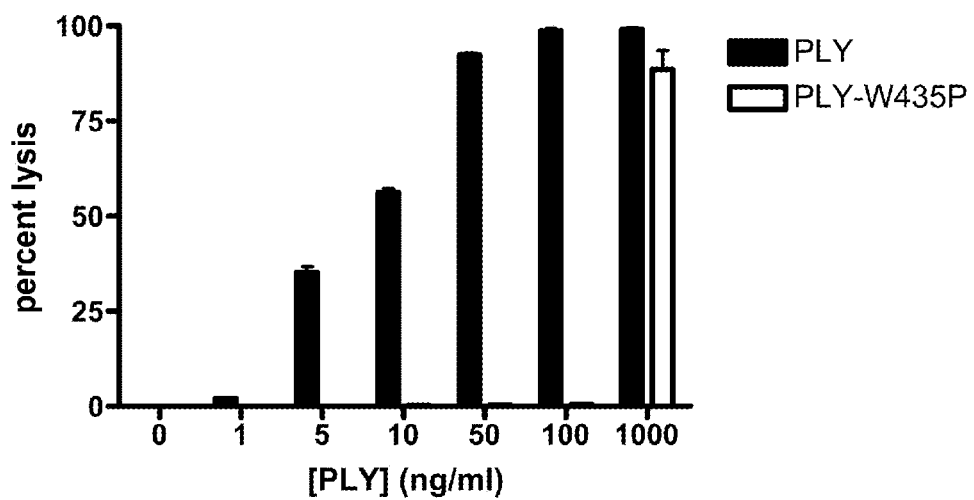

In order to investigate further the potential role of proline in pore forming activity, we made the converse mutation at the corresponding location (W435P) in pneumolysin, the species-non-specific CDC from S. pneumoniae. This pneumolysin mutant lysed erythrocytes, but only at concentrations much higher than wild-type toxin (FIG. 4D). This indicates that a substitution of tryptophan (W) for proline caused a loss of pore-forming activity. Construction of the corresponding mutation in PLY (i.e. substitution of proline for tryptophan at position 435) similarly led to a substantial decrease in its lytic activity.

Certain embodiments of the invention are also directed to toxoids of PLY and penumolysin, wherein there is an amino acid substitution of tryptophan for proline in the undecapeptide, and to the use of the PLY toxoids to elicit an immune response in a host.

These findings emphasize the importance of the structure of the undecapeptide region to the function of CDCs. Likewise, the substitution of a lysine residue for the conserved cysteine in the undecapeptide is a modification unique to VLY. Prior reports have demonstrated that the G. vaginalis hemolysin is not thiol-activated (35). The lack of enhancing effect of a reducing agent is consistent with this modification in the undecapeptide. Of note, in other CDC family members, the conserved cysteine residue confers thiol-activating properties but is not essential for pore-forming activity (37).

The following newly identified toxoids all have decreased pore-forming activity compared to the wild-type toxin, and are therefore useful in making a vaccine or antibodies against VLY or eliciting an immune response in a patient against G. vaginalis. Certain embodiments are directed to the toxoids listed below:

P480W, described above
N500I at position 500 change asparagines to isoleucine.
P480W, N500I double mutant
V471R, K473C double mutant
V471R, K473C, P480W triple mutant Other embodiments are directed to toxoids in which:
1. Some or all of domain 4 is deleted. (a portion of the sequence can be removed, or substituted or a premature stop codon can be inserted); and
2. Some or all of the amino acids in the undecapeptide (aa472-483) are replaced with alanine or phenylalanine; substitutions for the proline at position 480 in native VLY as stated before are particularly useful.

Certain embodiments of the present invention are directed to isolated and purified VLY recombinant toxoid proteins or an immunologic fragment or variant thereof, including P480W, N500I, V471R, K473C, P480W-N500I double mutant, V471R-K473C double mutant, and V471R-K473C-P480W triple mutant, or immunologic fragments or variants thereof, and to other purified toxoids described herein (including purified recombinant forms). Other embodiments include recombinant purified VLY protein or toxoids that have a 6×His tag on both the N-terminus (beginning) and C-terminus (end) of the protein to maximize purification. The tags can be removed after the VLY protein or toxoids are isolated and purified.

Other embodiments are directed to a composition comprising any of these toxoids or an immunologic fragment or variant thereof, for example to be used as immunogens in vaccines. Other embodiments are directed to a method for generating an immunologic response to VLY in an animal by administering to a patient a composition that includes one or more VLY toxoids such as the VLY (P480W) toxoid (or an immunologic fragment or variant thereof.

New Rabbit Polyclonal Anti-VLY Antibodies Detect G. vaginalis by Western Blot and Immunofluorescence Recombinant purified VLY toxin generated and purified as described in the Examples was submitted to Cocalico Biologicals, Inc. (Reamstown, Pa.). According to their protocol, adult rabbits were injected with a minimum of 100 µg antigen mixed with Complete Freund's Adjuvant subcutaneous and/or intramuscularly at multiple sites. Booster doses containing a minimum of 50 µg antigen mixed with Incomplete Freund's Adjuvant were administered on days 14, 21 and 49. A test bleed was performed on day 56. Prior to the first immunization, serum was collected from each rabbit to serve as negative control. We named the new anti-VLY polyclonal antibody thus derived "polyAnti-VLY;" certain embodiments of the invention are directed to this antibody and its therapeutic use to treat G. vaginalis infections and BV, and to prevent transmission of HIV to another from a woman infected with G. vaginalis or having BV.

Figure 5A:
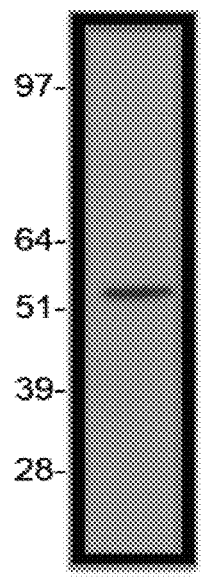
FIG. 5 Novel antibody techniques for the detection of VLY. (A) Western blot of *G. vaginalis* 14018 lysate probed with rabbit polyclonal antiserum (1:500,000 dilution). Numbers represent approximate MW in kD (B) Immunofluorescent detection of VLY production by *G. vaginalis* using pre-immune rabbit serum (left panel) or anti-VLY antiserum (right panel). Anti-rabbit IgG-AF488 was the secondary antibody (green). DNA staining with DAPI demonstrates bacteria in both panels (blue). Scale bar: 10 µm.
Figure 5B:
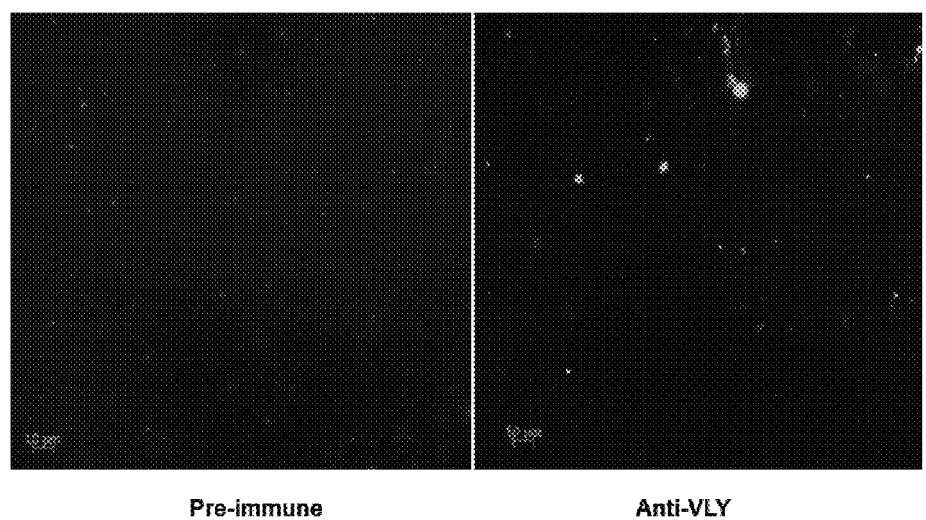

Western blot analysis of lysed G. vaginalis 14018 revealed a single band using polyclonal immune serum (polyAnti-VLY) as the primary antibody (FIG. 5A). This corresponds to the predicted 57 kDa molecular mass of VLY and to our prior findings using cross-reacting anti-pneumolysin antibody (50). There were no visible bands detected on membranes probed with pre-immune serum and processed identically (data not shown). Immunofluorescent detection of VLY associated with whole G. vaginalis was detected microscopically using immune serum and fluorescently labeled anti-rabbit secondary antibodies (FIG. 5B). Preimmune serum did not lead to detectable fluorescence of G. vaginalis (FIG. 5B).

Certain embodiments of the present invention are directed to the new rabbit polyAnti-VLY antibody, and fragments and variants thereof and to compositions that include the antibody that are intended for use in a mammal, particularly a human. Other embodiments are directed generally to polyclonal antibodies to VLY made by immunizing an animal with the isolated recombinant VLY toxins or a VLY toxoid as herein described, or an immunologically active fragment or variant thereof. Anti-VLY antibodies will bind to free VLY in the body. Other embodiments are directed to monoclonal anti-VLY antibodies made using well known hybridoma technology. In certain embodiments the anti-VLY antibodies can be humanized (as antibody or antibody fragments) and then administered therapeutically to a patient to confer passive immunity to G. vaginalis or BV or to neutralize VLY either systemically or locally in the vagina to prevent it from binding to CD 59. The antibodies can also be used in ELISA or RIA assays to detect the presence of VLY in a biological sample from a patient as is described below.

New ELISA that Detects VLY Production by G. vaginalis

Figure 6A:
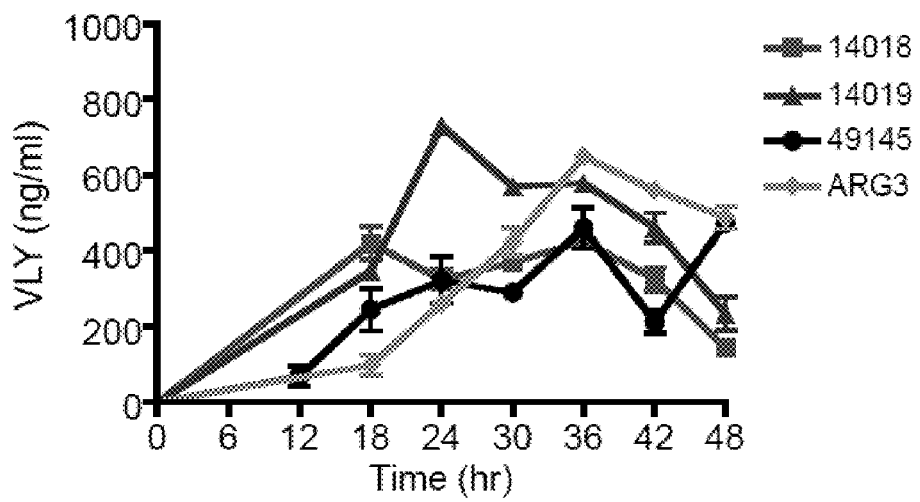
FIG. 6 Quantification of VLY production in vivo. (A) Detection of VLY in *G. vaginalis* supernatants by ELISA at various time points following inoculation of broth culture. (B) Bacterial growth (OD600) over the course of the experiment.
Figure 6B:
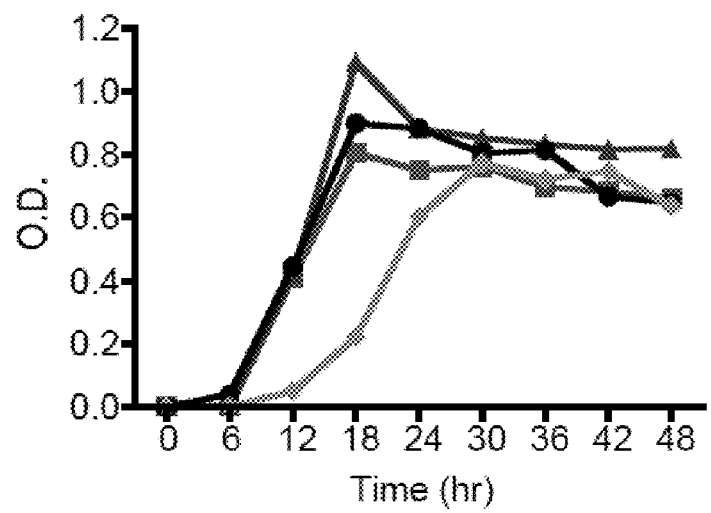

We developed a sandwich ELISA assay capable of quantifying VLY at ng/ml concentrations in the supernatant of growing G. vaginalis using rabbit polyAnti-VLY (diluted 1:1000 in blocking solution) as the detection antibody and known concentrations of recombinant VLY toxin diluted in G. vaginalis culture medium as a standard. As a secondary antibody we used goat anti-rabbit HRP antibody 1:100 dilution). We found that VLY toxin production peaked at between 24 and 36 hours of G. vaginalis in culture (FIG. 6A) and directly correlated with bacterial concentration as determined by optical density (FIG. 6 B). The ELISA technique is robust, even in the setting of potential inhibitors (such as serum) and will be useful for quantifying VLY production both in vitro and in vivo. The ELISA based assay in particular, is sensitive, robust and directly correlates with the concentration of G. vaginalis, reported to be an independent predictor of BV and subsequent preterm delivery. (61-65)

As an alternative means to assess VLY regulation, we also developed a sensitive real-time PCR assay targeting the VLY gene. This assay, which can be used either to detect DNA from organisms with the toxin gene or to monitor VLY RNA levels during different G. vaginalis growth conditions, represents an important strategy for our continued investigations.

Certain embodiments of the invention are directed to a kit for detecting VLY toxin or fragment that includes an anti-VLY antibody (including rabbit polyAnti-VLY) as the detection antibody, or anti-pneumolysin antibody, anti-PLY antibody, anti-ILY antibody or any other antibody that cross reacts with VLY. Such a kit can be used as a diagnostic tool for G. vaginalis infections and bacterial vaginosis by testing the presence of VLY in a biological sample from a patient. The biological sample is preferably a vaginal swab that has been diluted in sterile saline or PBS before the assay is run. It is expected that the swab will have not only vaginal cells, but also free VLY toxin. Another sample can be obtained by instilling 1-5 ml sterile saline into the vaginal of patient, and then collecting a biological sample from the vagina for the assay.

An embodiment of a kit for a sandwich ELISA optionally includes a secondary antibody (specific for the detection antibody) conjugated to an enzyme or other compound known in the art (including fluorescent labels/biotin avidin, radiolabels) that permits detection of the binding of the secondary antibody to the detection antibody.

In one embodiment the rabbit polyAnti-VLY is conjugated to an enzyme for an indirect assay. A major disadvantage of the indirect ELISA is that the method of antigen immobilization is non-specific; any proteins in the sample will stick to the microtiter plate well, so small concentrations of analyte in serum must compete with other serum proteins when binding to the well surface. The sandwich ELISA provides a solution to this problem: (1) Plate is coated with a capture antibody; (2) sample is added, and any antigen present binds to capture antibody; (3) detecting antibody is added, and binds to antigen; (4) enzyme-linked secondary antibody is added, and binds to detecting antibody; (5) substrate is added, and is converted by enzyme to detectable form.

In yet another embodiment the kit includes a capture antibody that binds VLY toxin to the substrate, thereby preventing nonspecific binding of peptides or proteins in the sample. The capture antibody can be anti-penumolysin antibody that we used (such as clone 1F11 or other clones that cross-reacts with VLY), or soluble CD59, anti-VLY antibodies including polyAnti-VLY, anti-PLY antibody, anti-pneumolysin, or monoclonal anti-VLY.

An ELISA may be run in a qualitative or quantitative format. Qualitative results provide a simple positive or negative result for a sample. The cutoff between positive and negative is determined by the analyst and may be statistical. Two or three times the standard deviation is often used to distinguish positive and negative samples. In quantitative ELISA, the optical density or fluorescent units of the sample is interpolated into a standard curve, which is typically a serial dilution of the target.

Antiserum Against VLY Inhibits Toxin-Mediated Cytolysis

Figure 7A:
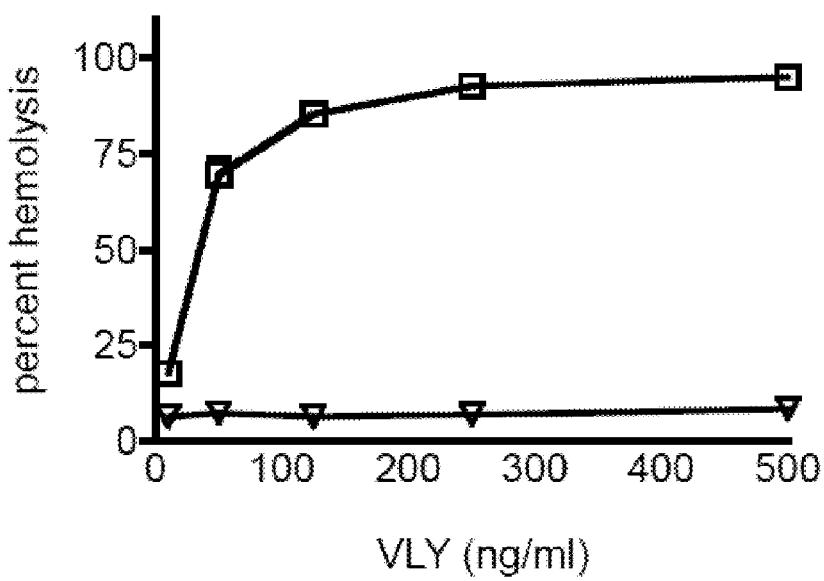
FIG. 7 Polyclonal immune serum inhibits VLY-mediated hemolysis. (A) Human erythrocytes were exposed to varying concentrations of purified recombinant VLY for 30 min. Cells were pelleted, and hemoglobin release was determined by OD415 of the supernatant. Values were normalized to 100% lysis. When indicated, VLY was preincubated with pre-bleed (VLY+PB) or immune serum (VLY+IS) diluted 1:50 for 30 min prior to use in the assay. (B) Erythrocytes were exposed to VLY (500 ng/ml), VLY+PB, or serial dilutions of VLY+IS. (P<0.001)
Figure 7B:
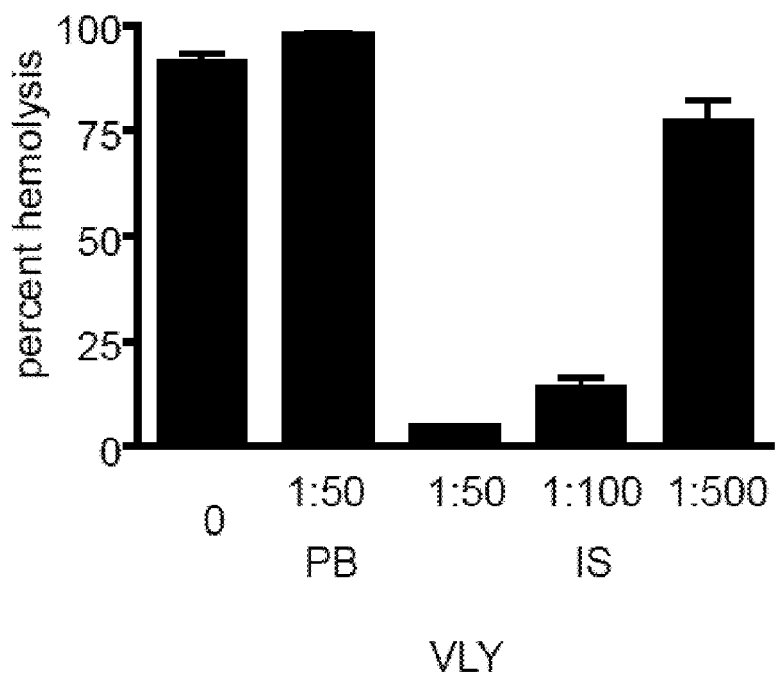

To test the biological activity of our antiserum to VLY, we studied toxin-mediated cytolysis of human erythrocytes, which are susceptible to hemolysis at various concentrations of purified recombinant VLY for 30 minutes (FIG. 7A). Preincubation of VLY with polyAnti-VLY (immune serum 1:50 dilution) prior to exposure to human erythrocytes resulted in significantly less hemolysis compared to untreated cells or cells exposed to pre-immune serum-treated VLY (FIG. 7A) Inhibition of VLY-mediated lysis by immune serum was dose-dependent (FIG. 7B).

Similarly, VLY-mediated cell lysis of human epithelial cell lines HeLa (FIG. 8A) and VK2 (FIG. 8B) was markedly reduced in the setting of immune serum. In order to generate a probe for toxin-hCD59 interactions, we created a GFP:VLYD4 fusion protein (not shown). This protein binds to hCD59-expressing human epithelial cells but does not form pores. It also can be used therapeutically to treat BV or *G. vaginalis* infections.

Treatment of *G. vaginalis* Infections and BV

The results above show that anti-VLY antibodies in general and polyAnti-VLY in particular can be used therapeutically to treat *G. vaginalis* infections by neutralizing free VLY. Such antibodies can be administered locally in the vagina as a topical formulation, or systemically. When the anti-VLY antibodies are administered locally/topically to the vagina, It is expected that the disadvantages of using rabbit antibodies instead of human antibodies is minimized.

New compositions that come within the scope of the invention for treating BV or *G. vaginalis* infections, or for preventing transmission of HIV from a BV/HIV-infected woman include:
  polyclonal and monoclonal anti-VLY antibodies (hereafter "anti-VLY antibodies") including the new anti-VLY antibody we described and named "rabbit polyAnti-VLY"
  Compositions comprising two or more of the following:
  anti-VLY antibodies, or fragments or variants thereof
  soluble CD59 or a fragment or variant thereof that binds to VLY
  anti-CD59 monoclonal or polyclonal antibodies that prevent VLY from binding to CD59 on the surface of epithelial cells or that prevent activation of surface CD59 by VLY, or fragments or variants thereof
  antibiotics known to be used in the treatment of BV or *G. vaginalis* infections, described herein
  anti-pneumolysin antibody, or fragments or variants thereof
  anti-VLY antibody, or fragments or variants thereof
  VLY toxoids which will compete with VLY toxin for binding to surface CD59 and that can be used for vaccines.

Reducing the Transmission of HIV by an Infected Woman

BV has been repeatedly associated with both a significant risk of HIV acquisition and increased viral shedding among those already infected 43-45. In vitro, treatment of HIV-infected cells with *Gardnerella* leads to increased production of viral transcripts. *J Infect Dis* 179: 924, *Lancet* 353: 525, and *J Bacteriol* 1190: 3896, incorporated herein by reference. Treatment of HIV-infected U-1 cells with purified VLY toxin in vitro caused a significant increase in HIV transcripts and p24 release. (Unpublished observations). Therefore, treatment or prevention of BV in women will also greatly reduce their susceptibility to becoming infected with HIV. An embodiment of the invention is directed to methods for reducing or preventing the transmission of HIV by a woman infected with both HIV and BV to another through intercourse by administering to the woman before she engages in a sexual activity, a therapeutically effective amount of a composition comprising a protective agent as described herein. In one embodiment the agent is applied topically to the vagina of the infected woman before engaging in the sexual activity. Vagina and birth canal are used synonymously herein.

The woman can be treated either topically or systemically or both. The protective agent(s) bind to VLY, or bind to CD59 receptor on target cells blocking the binding of VLY. In one embodiment, VLY toxoids as described herein bind to CD59 thereby preventing the toxin VLY from binding and lysing cells. Without being bound by theory we speculate that the protective agent neutralizes VLY produced from *G. vaginalis* infected cells thereby preventing it from binding to CD59 receptor on HIV-infected cells; this prevents VLY from increasing viral shedding by HIV-infected cells, which in turn reduces the risk of HIV infection to the uninfected sexual partner. A therapeutically effective amount of the protective agent is an amount that reduces or prevents transmission of HIV, preferably by reducing shedding by HIV-infected cells thereby reducing the viral load of HIV in a biological sample taken from the birth canal of the woman. A therapeutically effective amount that reduces viral load in a biological sample can be determined using routine experimentation.

Approximately 7,000 human immunodeficiency virus (HIV)-infected women give birth in the United States each year. This number is many times higher in Africa. Without treatment, about one-fourth of them transmit the virus to their children. The anti-HIV drug zidovudine (AZT), given to HIV-infected pregnant women before and during childbirth and to their infants after childbirth, reduces HIV transmission by as much as two-thirds. Treatment with AZT is now the standard of care in the U.S. for preventing HIV infection in infants. However, additional means are needed for the prevention of maternal to fetal transmission of HIV and other enveloped viruses both in the U.S. and worldwide. We have discovered compositions and methods that reduce the risk of a woman who is both HIV and BV positive transmitting HIV to an unborn fetus during the birth process.

One embodiment of the invention is directed to a method of reducing maternal to fetal transmission of HIV where the pregnant woman is infected with both HIV and BV, by administering a therapeutically effective amount of a protective agent either topically or systemically, or both, especially before and during a vaginal birth. Treatment of the pregnant HIV- and BV-infected individual should begin as soon as she is identified to reduce the viral load in the peripheral blood of the woman to both treat the BV and reduce the risk of the fetus becoming infected with HIV either before or during the birth.

When birth is approaching, treatment should be undertaken during labor until birth, with repeated topical application. Routine experimentation will determine the optimum schedule of administration. A therapeutically effective amount includes an amount that reduces or eliminates free HIV virus in a biological sample from the pregnant woman, such as a blood sample or a sample of vaginal secretion.

In another embodiment for preventing transmission of BV, *G. vaginalis* or HIV to a newborn, the preventative agent is administered topically to the newborn immediately after birth, for example, to an exposed tissue of the newborn such as the umbilical cord. The application of the preventive agent directly to the newborn can contribute to the reduction or elimination of a HIV viral particles that may be shed by any HIV-infected cells that remain from maternal-derived biological material on the newborn.

The methods described herein to reduce or prevent maternal to fetal transmission of an enveloped virus can be used in combination with one or more known treatments of HIV or BV, including using antiviral agents or antibacterial agents Antibodies for Use in the Present Invention "Antibody" or "antibodies" as described herein include intact molecules as well as fragments thereof that are capable of binding to an epitope of a VLY polypeptide or VLY toxoid, as described herein, to a fragment or variant thereof. The term "epitope" refers to an antigenic determinant on an antigen to which an antibody binds. Epitopes usually consist of chemically active surface groupings of molecules such as amino acids or sugar side chains, and typically have specific three-dimensional structural characteristics, as well as specific charge characteristics. Epitopes generally have at least five contiguous amino acids. The terms "antibody" and "antibodies" include polyclonal antibodies, monoclonal antibodies, humanized or chimeric antibodies, single chain Fv antibody fragments, Fab fragments, and F(ab)$_2$ fragments. Polyclonal antibodies are heterogeneous populations of antibody molecules that are specific for a particular antigen, while monoclonal antibodies are homogeneous populations of antibodies to a particular epitope contained within an antigen. Monoclonal antibodies are particularly useful.

The term "specifically binds" as used herein refers to the situation in which one member of a specific binding pair does not significantly bind to molecules other than its specific binding partner(s) as measured by a technique available in the art, e.g., competition ELISA. The term is also applicable where e.g. an antigen-binding domain of an antibody of the invention is specific for a particular epitope that is carried by a number of antigens (for example by VLY or fragment thereof such as domain 4 and the undecapeptide, or a VLY toxoid), in which case the antibody carrying the antigen-binding domain will be able to specifically bind to the various antigens carrying the epitope. The term "epitope" refers to that portion of a molecule capable of being recognized by and bound by an antibody at one or more of the antibody's antigen-binding regions.

"Specific binding" of an antibody also means that the antibody exhibits appreciable affinity for antigen or a preferred epitope and, preferably, does not exhibit significant crossreactivity. "Appreciable" or preferred binding include binding with an affinity of at least $10^6$, $10^7$, $10^8$, $10^9$ $M^{-1}$, or $10^{10}$ $M^{-1}$. Affinities greater than $10^7$ $M^{-1}$, preferably greater than $10^8$ $M^{-1}$ are more preferred. Values intermediate of those set forth herein are also intended to be within the scope of the present invention and a preferred binding affinity can be indicated as a range of affinities.

Antibody fragments that have specific binding affinity (as defined below) for VLY polypeptides can be generated by known techniques. Such antibody fragments include, but are not limited to, $F(ab')_2$ fragments that can be produced by pepsin digestion of an antibody molecule, and Fab fragments that can be generated by deducing the disulfide bridges of $F(ab')_2$ fragments. Alternatively, Fab expression libraries can be constructed. See, for example, Huse et al. (1989) Science 246:1275-1281. Single chain Fv antibody fragments are formed by linking the heavy and light chain fragments of the Fv region via an amino acid bridge (e.g., 15 to 18 amino acids), resulting in a single chain polypeptide. Single chain Fv antibody fragments can be produced through standard techniques, such as those disclosed in U.S. Pat. No. 4,946,778.

Once produced, antibodies or fragments thereof can be tested for recognition of a VLY polypeptide or toxoid by standard immunoassay methods including, for example, enzyme-linked immunosorbent assay (ELISA) or radioimmunoassay assay (RIA). See, Short Protocols in Molecular Biology eds. Ausubel et al., Green Publishing Associates and John Wiley & Sons (1992). Suitable antibodies typically have equal binding affinities for recombinant and native proteins.

An "antibody" refers to an intact immunoglobulin or to an antigen-binding portion thereof that competes with the intact antibody for specific binding. Antigen-binding portions may be produced by recombinant DNA techniques or by enzymatic or chemical cleavage of intact antibodies. Antigen-binding portions include, inter alia, Fab, Fab', F(ab').sub.2, Fv, dAb, and complementarity determining region (CDR) fragments, single-chain antibodies (scFv), chimeric antibodies, diabodies and polypeptides that contain at least a portion of an immunoglobulin that is sufficient to confer specific antigen binding to the polypeptide. An "immunoglobulin" is a tetrameric molecule. In a naturally-occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy terminal portion of each chain defines a constant region primarily responsible for effector function.

The monoclonal antibodies for use in the invention may be obtained by any technique which provides for the production of antibody molecules by continuous cell lines in culture. These include, but are not limited to, the hybridoma technique of Kohler and Milstein, (1975, Nature 256:495-497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026-2030), and the EBV-hybridoma technique (Cole et al., 1985, Monoclonal Antibodies And Cancer Therapy, Alan R. Liss, Inc., pp. 77-96). Such antibodies may be of any immunoglobulin class including IgG, IgM, IgE, IgA, IgD and any subclasses thereof. The hybridoma producing the mAb may be cultivated in vitro or in vivo.

Human light chains are classified as kappa and lambda light chains. Heavy chains are classified as mu, DELTA, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites. Immunoglobulin chains exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N terminus to C terminus, both light and heavy chains comprise the domains FR1, CDR1, FR2, CDR2, FR3, CDR3 and FR4. The assignment of amino acids to each domain is in accordance 44 with the definitions of Kabat Sequences of Proteins of Immunological Interest (National Institutes of Health, Bethesda, Md. (1987 and 1991)), or Chothia & Lesk J. Mol. Biol. 196:901 917 (1987); Chothia et al. Nature 342:878 883 (1989).

An Fab fragment is a monovalent fragment consisting of the VL, VH, CL and CH I domains; a F(ab').sub.2 fragment is a bivalent fragment comprising two Fab fragments linked by a disulfide bridge at the hinge region; a Fd fragment consists of the VH and CH1 domains; an Fv fragment consists of the VL and VH domains of a single arm of an antibody; and a dAb fragment (Ward et al., Nature 341:544 546, 1989) consists of a VH domain. A single-chain antibody (scFv) is an antibody in which a VL and VH regions are paired to form a monovalent molecules via a synthetic linker that enables them to be made as a single protein chain (Bird et al., Science 242:423 426, 1988 and Huston et al., Proc. Natl. Acad. Sci. USA 85:58795883, 1988). Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al., Proc. Natl. Acad. Sci. USA 90:6444 6448, 1993, and Poljak, R. J., et al., Structure 2: 1121 1123, 1994). One or more CDRs may be incorporated into a molecule either covalently or noncovalently to make it an immunoadhesin. An immunoadhesin may incorporate the CDR(s) as part of a larger polypeptide chain, may covalently link the CDR(s) to another polypeptide chain, or may incorporate the CDR(s) noncovalently. The CDRs permit the immunoadhesin to specifically bind to a particular antigen of interest.

An antibody may have one or more binding sites. If there is more than one binding site, the binding sites may be identical to one another or may be different. For instance, a naturally occurring immunoglobulin has two identical binding sites, a single-chain antibody or Fab fragment has one binding site, while a "bispecific" or "bifunctional" antibody has two different binding sites. An "isolated antibody" is an antibody that (1) is not associated with naturally associated components, including other naturally-associated antibodies, that accompany it in its native state, (2) is free of other proteins from the same species, (3) is expressed by a cell from a different species, or (4) does not occur in nature.

The term "human antibody" includes all antibodies that have one or more variable and constant regions derived from human immunoglobulin sequences. In a preferred embodiment, all of the variable and constant domains are derived from human immunoglobulin sequences (a fully human antibody). These antibodies may be prepared in a variety of ways, as described below.

A humanized antibody is an antibody that is derived from a non-human species, in which certain amino acids in the framework and constant domains of the heavy and light chains have been mutated so as to avoid or abrogate an immune response in humans. Alternatively, a humanized antibody may be produced by fusing the constant domains from a human antibody to the variable domains of a non-human species. Examples of how to make humanized antibodies may be found in U.S. Pat. Nos. 6,054,297, 5,886,152 and 5,877,293, incorporated herein by reference.

The term "chimeric antibody" refers to an antibody that contains one or more regions from one antibody and one or more regions from one or more other antibodies. Fragments or analogs of antibodies can be readily prepared by those of ordinary skill in the art following the teachings of this specification. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. Science 253: 164 (1991).

Pharmaceutical Compositions

The present invention also includes pharmaceutical compositions and formulations of the protective agents described herein. Pharmaceutical compositions of the present invention contain the therapeutic agent in an amount sufficient to prevent or treat the diseases described herein in a subject. These pharmaceutical compositions are suitable for administration to a subject in need of prophylaxis or therapy for any of the described diseases or conditions. The subject is preferably a human but can be non-human as well. A suitable subject can be an individual who is suspected of having, has been diagnosed as having, or is at risk of developing one of the described diseases.

In some embodiments the protective agent is formulated in a lubricant as described in Porat, U.S. Pat. No. 624,198, incorporated herein by reference, for intra-vaginal application or application to a newborn baby. In a preferred embodiment the lubricant-protective agent composition has a natural pH corresponding to that of the vagina. The lubricant may be any effective lubricant or combination of lubricants acceptable for cosmetic applications. Medical and pharmaceutical studies have shown that HIV develops mainly in the blood cells and is carried by various body fluids to other cells. The lubricant reduces the friction between the penis and the vaginal wall, thus reducing the rupture of blood cells which might otherwise occur and therefore reducing the amount of blood that is commingled. The protective agents of the present invention can also be formulated into gels and foams for application before or during sexual intercourse that are known in the art. In some embodiments the protective anti-shedding agents of the invention are included in disinfectant foam that coats the walls of the vagina and temporarily forms a closed layer of foam that traps and kills any HIV virus that may be present in addition to reducing or preventing further shedding. Schmittmann, et al., U.S. Pat. No. 6,022,545, incorporated herein by reference.

The preventive agent can be formulated into any topical composition known in the art that is suitable for its intended use as described herein, including creams, lotions, ointments, gels, lubricants, liquids, sprays, powders, or absorbent materials. The preventative agents can also be formulated for systemic administration for treating or preventing G. vaginalis or BV, or for use as a vaccine, or for reducing shedding in HIV-BV infected women as described herein. A composition of the preventive agents for either topical or systemic administration can also include a pharmaceutically acceptable carrier. As used herein the language "pharmaceutically acceptable carrier" includes solvents, dispersion media, coatings, antiviral agents, antibacterial agents, antifungal agents, isotonic and absorption delaying agents, and the like, compatible with pharmaceutical administration. Supplementary active compounds can also be incorporated into the compositions. Other topical formulations for preventing or reducing HIV transmission during birth are described in Sheele et al., U.S. Pat. No. 7,151,091, which is incorporated herein by reference.

Therapeutic compositions may contain, for example, such normally employed additives as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions typically contain 1%-95% of active ingredient, preferably 2%-70% active ingredient.

The protective agents can also be mixed with diluents or excipients which are compatible and physiologically tolerable. Suitable diluents and excipients are, for example, water, saline, dextrose, glycerol, or the like, and combinations thereof. In addition, if desired, the compositions may contain minor amounts of auxiliary substances such as wetting or emulsifying agents, stabilizing or pH buffering agents.

In some embodiments, the therapeutic compositions of the present invention are prepared either as liquid solutions or suspensions, as sprays, or in solid forms. Oral formulations usually include such normally employed additives such as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained release formulations, or powders, and typically contain 1%-95% of active ingredient, preferably 2%-70%. One example of an oral composition useful for delivering the therapeutic compositions of the present invention is described in U.S. Pat. No. 5,643,602 (incorporated herein by reference).

Additional formulations which are suitable for other modes of administration, such as topical administration, include salves, tinctures, creams, lotions, pessary, transdermal patches, ointments, gels, lubricants, liquid, sprays, powders, absorbent materials, and suppositories. For salves and creams, traditional binders, carriers and excipients may include, for example, polyalkylene glycols or triglycerides. One example of a topical delivery method is described in U.S. Pat. No. 5,834,016 (incorporated herein by reference). Other liposomal delivery methods may also be employed (See, e.g., U.S. Pat. Nos. 5,851,548 and 5,711,964, both of which are herein incorporated by reference). The composition can include an inert carrier. The composition can be impregnated in a towlette, sponge or capsule.

The formulations may also contain more than one active compound as necessary for the particular indication being treated, preferably those with complementary activities that do not adversely affect each other. Such molecules are suitably present in combination in amounts that are effective for the purpose intended.

Sustained-release preparations may also be prepared. Suitable examples of sustained release preparations include semipermeable matrices of solid hydrophobic polymers containing the protective agents, which matrices are in the form of shaped articles, e.g., films, or microcapsule. Examples of sustained release matrices include, but are not limited to, polyesters, hydro gels (for example, poly(2-hydroxyethylmethacrylate), or poly(vinylalcohol)), polylactides, copolymers of L-glutamic acid and y ethyl-L-glutamate, non-degradable ethylene-vinyl acetate, degradable lactic acid-glycolic acid copolymers such as the LUPRON DEPOT (injectable micro spheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

The protective agents of the present invention may be administered by any suitable means, preferably topically in the birth canal but also including systemic routes, such as parenteral, and subcutaneous. Parenteral infusions include intramuscular, intravenous, intra-arterial, intra-peritoneal, or subcutaneous administration.

For the prevention or treatment of disease, the appropriate dosage of antibody or other protective agent will depend on the type of disease to be treated, the severity and course of the disease, whether the drug is administered for protective or therapeutic purposes, previous therapy, the patient's clinical history and response to the drugs and the discretion of the attending physician.

The protective agents and vaccines are suitably administered to the patient at one time or over a series of treatments.

The amount of antibody to be administered therapeutically ranges typically from about 1 ug to 100 ug/ml. This amount typically varies and depends on the route of administration. The therapeutic agents of the invention can be administered by one or more separate administrations, topical or systemic administration, or by continuous infusion. For repeated administrations over several days or longer, depending on the condition, the treatment is sustained until the symptoms of G. vaginalis or BV are sufficiently reduced or eliminated, or until the HIV viral load is reduced in women with HIV and BV. The progress of this therapy is easily monitored by conventional techniques and assays, and may be used to adjust dosage to achieve a therapeutic effect.

Protein Modifications

VLY protein and toxoids, and their biologically active analogs, derivatives, fragments and variants for use in the present invention can be modified according to known methods in medicinal chemistry to increase its stability, half-life, uptake or efficacy. Certain known modifications are described below.

As is also well known, polypeptides are not always entirely linear. For instance, polypeptides may be branched as a result of ubiquitination, and they may be circular, with or without branching, generally as a result of post-translation events, including natural processing events and events brought about by human manipulation which do not occur naturally. Circular, branched and branched circular polypeptides may be synthesized by non-translational natural processes and by synthetic methods.

Modifications can occur anywhere in a polypeptide, including the peptide backbone, the amino acid side-chains and the amino or carboxyl termini. Blockage of the amino or carboxyl group in a polypeptide, or both, by a covalent modification, is common in naturally-occurring and synthetic polypeptides. For instance, the amino terminal residue of polypeptides made in E. coli, prior to proteolytic processing, almost invariably will be N-formylmethionine.

The modifications can be a function of how the protein is made. For recombinant polypeptides, for example, the modifications will be determined by the host cell posttranslational modification capacity and the modification signals in the polypeptide amino acid sequence. Accordingly, when glycosylation is desired, a polypeptide should be expressed in a glycosylating host, generally a eukaryotic cell. Insect cells often carry out the same posttranslational glycosylations as mammalian cells, and, for this reason, insect cell expression systems have been developed to efficiently express mammalian proteins having native patterns of glycosylation. Similar considerations apply to other modifications. The same type of modification may be present in the same or varying degree at several sites in a given polypeptide. Also, a given polypeptide may contain more than one type of modification.

VLY protein and toxoids can be isolated and purified from cells that naturally express it, purified from cells that naturally express it but have been modified to overproduce it, e.g., purified from cells that have been altered to express it (recombinantly), synthesized using known protein synthesis methods, or by modifying cells that naturally encode VLY or VLY toxoid to express it.

| Protein Modification | Description |
| --- | --- |
| Acetylation | Acetylation of N-terminus or e-lysines. Introducing an acetyl group into a protein, specifically, the substitution of an acetyl group for an active hydrogen atom.<br>A reaction involving the replacement of the hydrogen atom of a hydroxyl group with an acetyl group ($CH_3CO$) yields a specific ester, the acetate. Acetic anhydride is commonly used as an acetylating agent, which reacts with free hydroxyl groups. Acylation may facilitate addition of other functional groups. A common reaction is acylation of e.g., conserved lysine residues with a biotin appendage. |
| ADP-ribosylation | Covalently linking proteins or other compounds via an arginine-specific reaction. |
| Alkylation | Alkylation is the transfer of an alkyl group from one molecule to another. The alkyl group may be transferred as an alkyl carbocation, a free radical or a carbanion (or their equivalents). Alkylation is accomplished by using certain functional groups such as alkyl electrophiles, alkyl nucleophiles or sometimes alkyl radicals or carbene acceptors. A common example is methylation (usually at a lysine or arginine residue). |
| Amidation | Reductive animation of the N-terminus. Methods for amidation of insulin are described in U.S. Pat. No. 4,489,159. |
| Carbamylation | Nigen et al. describes a method of carbamylating hemoglobin. |
| Carboxylation | Carboxylation typically occurs at the glutamate residues of a protein, which may be catalyzed by a carboxylase enzyme (in the presence of Vitamin K - a cofactor). |
| Citrullination | Citrullination involves the addition of citrulline amino acids to the arginine residues of a protein, which is catalyzed by peptidylarginine deaminase enzymes (PADs). This generally converts a positively charged arginine into a neutral citrulline residue, which may affect the hydrophobicity of the protein (and can lead to unfolding). |
| Condensation of amines with aspartate or glutamate | Such reactions, may be used, e.g., to attach a peptide to other proteins labels. |
| Covalent attachment of flavin | Flavin mononucleotide (FAD) may be covalently attached to serine and/or threonine residues. May be used, e.g., as a light-activated tag. |
| Covalent attachment of heme moiety | A heme moiety is generally a prosthetic group that consists of an iron atom contained in the center of a large heterocyclic organic ring, which is referred to as a porphyrin. The heme moiety may be used, e.g., as a tag for the peptide. |
| Attachment of a nucleotide or nucleotide derivative | May be used as a tag or as a basis for further derivatising a peptide. |
| Cross-linking | Cross-linking is a method of covalently joining two proteins. Cross-linkers contain reactive ends to specific functional groups (primary amines, sulfhydryls, etc.) on proteins or other molecules. Several chemical groups may be targets for reactions in proteins and peptides. For example, Ethylene glycol bis[succinimidylsuccinate, Bis[2-(succinimidooxycarbonyloxy)ethyl]sulfone, and Bis[sulfosuccinimidyl] suberate link amines to amines. |
| Cyclization | For example, cyclization of amino acids to create optimized delivery forms that are resistant to, e.g., aminopeptidases (e.g., formation of pyroglutamate, a cyclized form of glutamic acid). |
| Disulfide bond formation | Disulfide bonds in proteins are formed by thiol-disulfide exchange reactions, particularly between cysteine residues (e.g., formation of cystine). |
| Demethylation | See, e.g., U.S. Pat. No. 4,250,088 (Process for demethylating lignin). |
| Formylation | The addition of a formyl group to, e.g., the N-terminus of a protein. See, e.g., U.S. Pat. Nos. 4,059,589, 4,801,742, and 6,350,902. |
| Glycylation | The covalent linkage of one to more than 40 glycine residues to the tubulin C-terminal tail. |
| Glycosylation | Glycosylation may be used to add saccharides (or polysaccharides) to the hydroxy oxygen atoms of serine and threonine side chains (which is also known as O-linked Glycosylation). Glycosylation may also be used to add saccharides (or polysaccharides) to the amide nitrogen of asparagine side chains (which is also known as N-linked Glycosylation), e.g., via oligosaccharyl transferase. |
| GPI anchor formation | The addition of glycosylphosphatidylinositol to the C-terminus of a protein. GPI anchor formation involves the addition of a hydrophobic phosphatidylinositol group - linked through a carbohydrate containing linker (e.g., glucosamine and mannose linked to phosphoryl ethanolamine residue) - to the C-terminal amino acid of a protein. |
| Hydroxylation | Chemical process that introduces one or more hydroxyl groups (—OH) into a protein (or radical). Hydroxylation reactions are typically catalyzed by hydroxylases. Proline is the principal residue to be hydroxylated in proteins, which occurs at the $C^\gamma$ |

| Protein Modification | Description |
| --- | --- |
| | atom, forming hydroxyproline (Hyp). In some cases, proline may be hydroxylated at its $C^\beta$ atom. Lysine may also be hydroxylated on its $C^\delta$ atom, forming hydroxylysine (Hyl). These three reactions are catalyzed by large, multi-subunit enzymes known as prolyl 4-hydroxylase, prolyl 3-hydroxylase and lysyl 5-hydroxylase, respectively. These reactions require iron (as well as molecular oxygen and α-ketoglutarate) to carry out the oxidation, and use ascorbic acid to return the iron to its reduced state. |
| Iodination | See, e.g., U.S. Pat. No. 6,303,326 for a disclosure of an enzyme that is capable of iodinating proteins. U.S. Pat. No. 4,448,764 discloses, e.g., a reagent that may be used to iodinate proteins. |
| ISGylation | Covalently linking a peptide to the ISG15 (Interferon-Stimulated Gene 15) protein, for, e.g., modulating immune response. |
| Methylation | Reductive methylation of protein amino acids with formaldehyde and sodium cyanoborohydride has been shown to provide up to 25% yield of N-cyanomethyl ($-CH_2CN$) product. The addition of metal ions, such as $Ni^{2+}$, which complex with free cyanide ions, improves reductive methylation yields by suppressing by-product formation. The N-cyanomethyl group itself, produced in good yield when cyanide ion replaces cyanoborohydride, may have some value as a reversible modifier of amino groups in proteins. (Gidley et al.) Methylation may occur at the arginine and lysine residues of a protein, as well as the N- and C-terminus thereof. |
| Myristoylation | Myristoylation involves the covalent attachment of a myristoyl group (a derivative of myristic acid), via an amide bond, to the alpha-amino group of an N-terminal glycine residue. This addition is catalyzed by the N-myristoyltransferase enzyme. |
| Oxidation | Oxidation of cysteines. Oxidation of N-terminal Serine or Threonine residues (followed by hydrazine or aminooxy condensations). Oxidation of glycosylations (followed by hydrazine or aminooxy condensations). |
| Palmitoylation | Palmitoylation is the attachment of fatty acids, such as palmitic acid, to cysteine residues of proteins. Palmitoylation increases the hydrophobicity of a protein. |
| (Poly)glutamylation | Polyglutamylation occurs at the glutamate residues of a protein. Specifically, the gamma-carboxy group of a glutamate will form a peptide-like bond with the amino group of a free glutamate whose alpha-carboxy group may be extended into a polyglutamate chain. The glutamylation reaction is catalyzed by a glutamylase enzyme (or removed by a deglutamylase enzyme). Polyglutamylation has been carried out at the C-terminus of proteins to add up to about six glutamate residues. Using such a reaction, Tubulin and other proteins can be covalently linked to glutamic acid residues. |
| Phosphopantetheinylation | The addition of a 4'-phosphopantetheinyl group. |
| Phosphorylation | A process for phosphorylation of a protein or peptide by contacting a protein or peptide with phosphoric acid in the presence of a non-aqueous apolar organic solvent and contacting the resultant solution with a dehydrating agent is disclosed e.g., in U.S. Pat. No. 4,534,894. Insulin products are described to be amenable to this process. See, e.g., U.S. Pat. No. 4,534,894. Typically, phosphorylation occurs at the serine, threonine, and tyrosine residues of a protein. |
| Prenylation | Prenylation (or isoprenylation or lipidation) is the addition of hydrophobic molecules to a protein. Protein prenylation involves the transfer of either a farnesyl (linear grouping of three isoprene units) or a geranyl-geranyl moiety to C-terminal cysteine(s) of the target protein. |
| Proteolytic Processing | Processing, e.g., cleavage of a protein at a peptide bond. |
| Selenoylation | The exchange of, e.g., a sulfur atom in the peptide for selenium, using a selenium donor, such as selenophosphate. |
| Sulfation | Processes for sulfating hydroxyl moieties, particularly tertiary amines, are described in, e.g., U.S. Pat. No. 6,452,035. A process for sulphation of a protein or peptide by contacting the protein or peptide with sulphuric acid in the presence of a non-aqueous apolar organic solvent and contacting the resultant solution with a dehydrating agent is disclosed. Insulin products are described to be amenable to this process. See, e.g., U.S. Pat. No. 4,534,894. |
| SUMOylation | Covalently linking a peptide a SUMO (small ubiquitin-related Modifier) protein, for, e.g., stabilizing the peptide. |
| Transglutamination | Covalently linking other protein(s) or chemical groups (e.g., PEG) via a bridge at glutamine residues |

| Protein Modification | Description |
|---|---|
| tRNA-mediated addition of amino acids (e.g., arginylation) | For example, the site-specific modification (insertion) of an amino acid analog into a peptide. |

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense.

The invention is illustrated herein by the experiments described above and by the following examples, which should not be construed as limiting. The contents of all references, pending patent applications and published patents, cited throughout this application are hereby expressly incorporated by reference. Those skilled in the art will understand that this invention may be embodied in many different forms and should not be construed as limited to the embodiments set forth herein. Rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

SEQUENCES

VLY protein from [organism = Strain 14018 and 14019 Gardnerella vaginalis] DNA
Sequence ID NO: 1
ATGAAGAGTACAAAGTTCTACCGTAATGCAGCAATGTTGCTCCTCGCGGG

CGCAACTATTGTTCCACAATGCTTAG

CAGCACCAGCAATGGCCGCTCCTTCCGCTAAGGATTCTGAACCAGCTACA

TCTTGCGCAGCTAAGAAAGACTCGTT

GAATAATTATTTGTGGGATTTGCAATACGATAAAACAAACATTCTCGCCC

GTCATGGCGAAACCATTGAGAACAAA

TTCTCCAGCGACAGCTTCAACAAGAACGGTGAATTCGTTGTTGTTGAGCA

TCAGAAGAAGAACATCACCAATACAA

CTTCAAATTTGTCGGTTACTTCCGCCAACGATGATCGCGTATACCCAGGT

GCTCTTTTCCGTGCTGATAAGAATTT

GATGGACAATATGCCAAGCCTGATTTCTGCAAACCGCGCTCCAATAACGT

TGAGCGTTGATTTGCCGGGATTCCAC

GGCGGCGAAAGTGCTGTAACTGTTCAGCGCCCAACCAAGAGCTCTGTAAC

TTCCGCAGTGAACGGCTTAGTTTCTA

AGTGGAATGCACAATATGGAGCAAGTCATCATGTTGCAGCTCGCATGCAG

TACGATTCTGCAAGCGCACAAAGCAT

GAACCAGCTCAAGGCTAAGTTTGGTGCTGATTTTGCCAAGATTGGTGTTC

CGCTGAAGATTGATTTCGATGCAGTA

CACAAGGGTGAGAAGCAGACTCAAATTGTGAACTTCAAGCAAACTTACTA

CACCGTAAGCGTTGATGCACCAGATA

GCCCAGCAGATTTCTTTGCTCCTTGCACTACGCCAGACAGCTTGAAGAAC

CGTGGCGTTGACAACAAGCGCCCACC

AGTTTACGTGTCAAACGTAGCTTATGGTCGCTCAATGTACGTAAAGTTCG

ATACCACCAGCAAGAGCACTGATTTC

CAGGCTGCGGTAGAAGCAGCAATTAAGGGCGTAGAAATCAAGCCAAACAC

CGAATTCCATCGCATTCTCCAGAATA

CTTCTGTTACTGCAGTGATTCTTGGTGGCAGCGCTAATGGTGCAGCTAAA

GTTATTACAGGCAATATCGATACGCT

TAAGGCTTTGATTCAGGAAGGTGCAAATTTGAGCACCTCTAGCCCAGCGG

TTCCAATTGCATACACCACTTCCTTC

GTCAAGGATAACGAAGTAGCAACTTTGCAATCCAACAGCGATTATATTGA

AACGAAGGTTTCTTCTTATCGCAATG

GCTACTTGACTTTGGACCACCGTGGAGCTTATGTAGCTCGCTACTACATC

TACTGGGATGAGTACGGCACCGAAAT

TGACGGCACTCCTTACGTGCGTTCTCGCGCTTGGGAAGGCAATGGTAAGT

ATCGTACAGCTCACTTCAACACCACT

ATTCAGTTCAAAGGAAATGTACGCAATCTACGAATCAAGTTGGTTGAAAA

GACTGGTTTGGTTTGGGAACCATGGC

GCACAGTATATGACCGTTCTGATTTGCCACTAGTTCGTCAGCGTACTATT

AGCAACTGGGGCACAACCTTGTGGCCTCGCGTTGCTGAAACTGTAAAGAA

CGACTGA

VLY protein from [organism = Strain 14018 and 14019 Gardnerella vaginalis] Amino Acid
Sequence ID NO: 2
MKSTKFYRNAAMLLLAGATIVPQCLAAPAMAAPSAKDSEPATSCAAKKDS

LNNYLWDLQYDKTNILARHGETIENKFSSDSFNKNGEFVVVEHQKKNITN

TTSNLSVTSANDDRVYPGALFRADKNLMDNMPSLISANRAPITLSVDLPG

FHGGESA VTVQRPTKSSVTSA VNGL VSKWNAQYGASHHV AARMQYD

SASAQSMNQLKAKFGADF AKIGVPLKIDFDAVHKGEKQTQIVNFKQTYY

TVSVDAPDSPADFFAPCTTPDSLKNRGVDNKRPPVYVSNV A YGRSMYV

KFDTTSKSTDFQAA VEAAIKGVEIKPNTEFHRILQNTSVTAVILGGSAN

GAAKVITGNIDTLKALIQEGANLSTSSPA VPIA YTTSFVKDNEV ATL

QSNSDYIETKVSSYRNGYLTLDHRGA YV ARYYIYWDEYGTEIDGTPYV

-continued
RSRA WEGNGKYRTAHFNTTIQFKGNVRNLRIKL VEKTGL VWEPWRTV

YDRSDLPLVRQRTISNWGTTL WPRV AETVKND

VLY protein from [organism = Gardnerella
Vaginalis 49145] DNA
SEQ ID NO: 3
ATGAAGAGTACAAAGTTCTACCGTAATGCAGCAATGTTGCTCCTCGCGGG

CGCAACTATTGTTCCACAATGCTTAG

CAGCACCAGCAATGGCCGCTCCTTCCGCTAAGGATTCTGAACCAGCTACA

TCTTGCGCAGCTAAGAAAGACTCGTT

GAATAATTATTTGTGGGATTTGCAATACGATAAAACAAACATTCTCGCCC

GTCATGGCGAAACCATTGAGAACAAA

TTCTCCAGCGACAGCTTCAACAAGAACGGTGAATTCGTTGTTGTTGAGCA

TCAGAAGAAGAACATCACCAATACAA

CTTCAAATTTGTCGGTTACTTCCGCCAACGATGATCGCGTATACCCAGGT

GCTCTTTTCCGTGCTGATAAGAATTT

GATGGACAATATGCCAAGCCTGATTTCTGCAAACCGCGCTCCAATAACGT

TGAGCGTTGATTTGCCGGGATTCCAC

GGCGGCGAAAGTGCTGTAACTGTTCAGCGCCCAACCAAGAGCTCTGTAAC

TTCCGCAGTGAACGGCTTAGTTTCTA

AGTGGAATGCACAATATGGAGCAAGTCATCATGTTGCAGCTCGCATGCAG

TACGATTCTGCAAGCGCACAAAGCAT

GAACCAGCTCAAGGCTAAGTTTGGTGCTGATTTTGCCAAGATTGGTGTTC

CGCTGAAGATTGATTTCGATGCAGTA

CACAAGGGTGAGAAGCAGACTCAAATTGTGAACTTCAAGCAAACTTACTA

CACCGTAAGCGTTGATGCACCAGATA

GCCCAGCAGATTTCTTTGCTCCTTGCACTACGCCAGACAGCTTGAAGAAC

CGTGGCGTTGACAACAAGCGCCCACC

AGTTTACGTGTCAAACGTAGCTTATGGTCGCTCAATGTACGTAAAGTTCG

ATACCACCAGCAAGAGCACTGATTTC

CAGGCTGCAGTAGAAGCAGCAATTAAGGGCGTAGAAATCAAGCCAAACAC

CGAATTCCATCGCATTCTCCAAAATA

CTTCTGTTACTGCAGTGATTCTTGGTGGCAGCGCTAATGGTGCAGCTAAA

GTTATTACAGGCAACATCGATACGTT

GAAGGCTTTGATTCAGGAAGGTGCAAATTTGAGCACCTCTAGCCCAGCAG

TTCCAATTGCATACACCACTTCCTTC

GTCAAGGATAACGAAGTAGCAACTTTGCAATCCAACAGCGATTATATTGA

AACGAAGGTTTCCTCTTACCGCAATG

GCTACTTGACTTTGGACCACCGTGGAGCTTACGTAGCTCGCTACTACATC

TACTGGGATGAGTACGGCACCGAAAT

TGACGGCACTCCTTACGTGCGTTCTCGCGCTTGGGAAGGCAATGGTAAGT

ATCGTACAGCTCACTTCAATACCACT

ATTCAGTTCAAAGGAAATGTACGCAATCTACGAATCAAGTTGGTTGAAAA

GACTGGTTTAGTTTGGGAACCATGG

GCACAGTATATGACCGTTCTGATTTGCCACTAGTTCATCAGCGTACTATT

AGCAACTGGGGCACAACCTTGTGGCCTCGCGTTGCTGAAACTGTAAAGAA

CGACTGA

VLY DOMAIN 4 DNA FROM Gardnerella vaginalis
14018 and 14019 nucleic acid 1126 to the
end 1551 V
SEQ ID NO: 4
TACACCACTTCCTTC

GTCAAGGATAACGAAGTAGCAACTTTGCAATCCAACAGCGATTATATTGA

AACGAAGGTTTCTTCTTATCGCAATG

GCTACTTGACTTTGGACCACCGTGGAGCTTATGTAGCTCGCTACTACATC

TACTGGGATGAGTACGGCACCGAAAT

TGACGGCACTCCTTACGTGCGTTCTCGCGCTTGGGAAGGCAATGGTAAGT

ATCGTACAGCTCACTTCAACACCACT

ATTCAGTTCAAAGGAAATGTACGCAATCTACGAATCAAGTTGGTTGAAAA

GACTGGTTTGGTTTGGGAACCATGG

GCACAGTATATGACCGTTCTGATTTGCCACTAGTTCGTCAGCGTACTATT

AGCAACTGGGGCACAACCTTGTGGCCTCGCGTTGCTGAAACTGTAAAGAA

CGACTGA

VLY DOMAIN 4 DNA
FROM Gardnerella vaginalis 49145 nucleic acid
1126 to the end 1551 V
SEQ ID NO: 12
TACACCACTTCCTTCGTCAAGGATAACGAAGTAGCAACTTTGCAATCCAA

CAGCGATTATATTGAAACGAAGGTTTCCTCTTACCGCAATGGCTACTTGA

CTTTGGACCACCGTGGAGCTTACGTAGCTCGCTACTACATCTACTGGGAT

GAGTACGGCACCGAAATTGACGGCACTCCTTACGTGCGTTCTCGCGCTTG

GGAAGGCAATGGTAAGTATCGTACAGCTCACTTCAATACCACTATTCAGT

TCAAAGGAAATGTACGCAATCTACGAATCAAGTTGGTTGAAAAGACTGGT

TTAGTTTGGGAACCATGGCGCACAGTATATGACCGTTCTGATTTGCCACT

AGTTCATCAGCGTACTATTAGCAACTGGGGCACAACCTTGTGGCCTCGCG

TTGCTGAAACTGTAAAGAACGACTGA

VLY DOMAIN 4
Amino Acid
FROM Gardnerella vaginalis 14018 and 14019
SEQ ID NO: 5
YTTSFVKDNEV ATLQSNSDYIETKVSSYRNGYLTLDHRGA YV ARYYI

YWDEYGTEIDGTPYVRSRA WEGNGKYRTAHFNTTIQFKGNVRNLRIKL

VEKTGL VWEPWRTVYDRSDLPL VRQRTISNWGTTLWPRV AETVKND

VLY DOMAIN 4
Amino Acid
FROM Gardnerella vaginalis 49145:
SEQ ID NO: 13
YTTSFVKDNEV ATLQSNSDYIETKVSSYRNGYLTLDHRGA YV ARYYI

YWDEYGTEIDGTPYVRSRA WEGNGKYRTAHFNTTIQFKGNVRNLRIKL

VEKTGL VWEPWRTVYDRSDLPL VHQRTISNWGTTL WPRV AETVKND

VLY Undecapeptide
FROM *Gardnerella vaginalis* 14018 and 14019 DNA
nucleic acid residues 1414-1446
SEQ ID NO: 6
GAAAAGACTGGTTTGGTTTGGGAACCATGGCGC VLY Undecapeptide
FROM *Gardnerella vaginalis* 49145 DNA
nucleic acid residues 1414-1446
SEQ ID NO: 14
GAAAAGACTGGTTTAGTTTGGGAACCATGGCGC VLY UNDECAPEPTIDE
FROM *Gardnerella vaginalis* (CONSERVED)
Amino acids 472 to 482 AMINO ACID SEQUENCE
SEQ ID NO: 7
EKTGLVWEPWR VLY UNDECAPEPTIDE P480W TOXOID FROM *Gardnerella vaginalis* (CONSERVED)
Undecapeptide amino acids 472 to 482 Amino Acid
SEQ ID NO: 8
EKTGLVWEWWR Codon optimized VLY gene sequence (same protein sequence as VLY from strain 14018) DNA
SEQ ID NO: 9
ATGAAAAGCACCAAATTTTATCGTAACGCGGCGATGCTGCTGCTGGCAGG

TGCA

ACCATTGTGCCGCAGTGCCTGGCAGCACCGGCAATGGCAGCACCGAGCGC

AAAAGATAGC

GAACCGGCGACCAGCTGCGCGGCGAAAAAAGATAGCCTGAACAACTATCT

GTGGGATCTG

CAGTATGATAAAACCAACATTCTGGCGCGTCATGGCGAAACCATTGAAAA

CAAATTTAGC

AGCGATAGCTTTAACAAAAACGGCGAATTTGTGGTGGTGGAACATCAGAA

GAAAAACATT

ACCAACACCACCAGCAACCTGAGCGTGACCAGCGCGAACGATGATCGTGT

GTATCCGGGC

GCGCTGTTTCGTGCGGATAAAAACCTGATGGATAACATGCCGAGCCTGAT

TAGCGCGAAC

CGTGCGCCGATTACCCTGAGCGTGGATCTGCCGGGCTTTCATGGCGGCGA

AAGCGCGGTG

ACCGTGCAGCGTCCGACCAAAAGCAGCGTGACCAGCGCGGTGAACGGCCT

GGTTAGCAAA

TGGAACGCGCAGTATGGCGCGAGCCATCATGTGGCGGCGCGTATGCAGTA

TGATAGCGCG

AGCGCGCAGAGCATGAACCAGCTGAAAGCGAAATTTGGCGCGGATTTTGC

GAAAATTGGC

GTGCCGCTGAAAATTGATTTTGATGCGGTGCATAAAGGCGAAAACAGAC

CCAGATTGTG

AACTTTAAACAGACCTATTATACCGTGAGCGTGGATGCGCCGGATAGCCC

GGCGGATTTC

TTTGCGCCGTGCACCACCCCGGATAGCCTGAAAAACCGTGGCGTGGATAA

CAAACGTCCG

CCGGTGTATGTGAGCAACGTGGCGTATGGCCGTAGCATGTATGTGAAATT

TGATACCACC

AGCAAAAGCACCGATTTTCAGGCGGCGGTGGAAGCGGCGATTAAAGGCGT

GGAAATTAAA

CCGAACACCGAATTTCATCGTATTCTGCAGAACACCAGCGTGACCGCGGT

GATTCTGGGC

GGCAGCGCGAACGGCGCGGCGAAAGTGATTACCGGCAACATTGATACCCT

GAAAGCGCTG

ATTCAGGAAGGCGCGAACCTGAGCACCAGCAGCCCGGCGGTGCCGATTGC

GTATACCACC

AGCTTTGTGAAAGATAACGAAGTGGCGACCCTGCAGAGCAACAGCGATTA

TATTGAAACC

AAAGTGAGCAGCTATCGTAACGGCTATCTGACCCTGGATCATCGTGGCGC

GTATGTGGCG

CGTTATTATATTTATTGGGATGAATATGGCACCGAAATTGATGGCACCCC

GTATGTGCGT

AGCCGTGCGTGGGAAGGCAACGGCAAATATCGTACCGCGCATTTTAACAC

CACCATTCAG

TTTAAAGGCAACGTGCGTAACCTGCGTATTAAACTGGTGGAAAAAACCGG

CCTGGTGTGG

GAACCGTGGCGTACCGTGTATGATCGTAGCGATCTGCCGCTGGTGCGTCA

GCGTACCATT

AGCAACTGGGGCACCACCCTGTGGCCGCGTGTGGCGGAAACCGTGAAAAA

CGATTAA

*Gardnerella vaginalis* strain ARG3 VLY DNA
SEQ ID NO: 10
ATGAAGAGTACAAAGTTCTACCGTAATGCAGCAATGTTGCTCCTCGCGGG

CGCAACTATTGTTCCACAATGCTTAGCAGCACCAGCAATGGCCGCTCCTT

CCGCTAAGGATTCTGAACCAGCTACATCTTGCGCAGCTAAGAAAGACTCG

TTGAATAATTATTTGTGGGATTTGCAATACGATAAAACAAACATTCTCGC

CCGTCATGGCGAAACCATTGAGAACAAATTCTCCAGCGACAGCTTCAACA

AGAACGGTGAATTCGTTGTTGTTGAGCATCAGAAGAAGAACATCACCAAT

ACAACTTCAAATTTGTCGGTTACTTCCGCCAACGATGATCGCGTATACCC

AGGTGCTCTTTTCCGTGCTGATAAGAATTTGATGGACAATATGCCAAGCC

TGATTTCTGCAAACCGCGCTCCAATAACGTTGAGCGTTGATTTGCCGGGA

TTCCACGGCGGCGAAAGTGCTGTAACTGTTCAGCGCCCAACCAAGAGCTC

TGTAACTTCCGCAGTGAACGGCTTAGTTTCTAAGTGGAATGCACAATATG

GAGCAAGTCATCATGTTGCAGCTCGCATGCAGTACGATTCTGCAAGCGCA

CAAAGCATGAACCAGCTCAAGGCTAAGTTTGGTGCTGATTTTGCCAAGAT

TGGTGTTCCGCTGAAGATTGATTTCGATGCAGTACAAGGGTGAGAAGC

AGACTCAAATTGTGAACTTCAAGCAAACTTACTACACCGTAAGCGTTGAT

-continued

```
GCACCAGATAGCCCAGCAGATTTCTTTGCTCCTTGCACTACGCCAGACAG

CTTGAAGAACCGTGGCGTTGACAACAAGCGCCCACCAGTTTACGTGTCAA

ACGTAGCTTATGGTCGCTCAATGTACGTAAAGTTCGATACCACCAGCAAG

AGCACTGATTTCCAGGCTGCGGTAGAAGCAGCAATTAAGGGCGTAGAAAT

CAAGCCAAACACCGAATTCCATCGCATTCTCCAGAATACTTCTGTTACTG

CAGTGATTCTTGGTGGCAGCGCTAATGGTGCAGCTAAAGTTATTACAGGC

AATATCGATACGCTTAAGGCTTTGATTCAGGAAGGTGCAAATTTGAGCAC

CTCTAGCCCAGCGGTTCCAATTGCATACACCACTTCCTTCGTCAAGGATA

ACGAAGTAGCAACTTTGCAATCCAACAGCGATTATATTGAAACGAAGGTT

TCTTCTTATCGCAATGGCTACTTGACTTTGGACCACCGTGGAGCTTATGT

AGCTCGCTACTACATCTACTGGGATGAGTACGGCACCGAAATTGACGGCA

CTCCTTACGTGCGTTCTCGCGCTTGGGAAGGCAATGGTAAGTATCGTACA

GCTCACTTCAACACCACTATTCAGTTCAAAGGAAATGTACGCAATCTACG

AATCAAGTTGGTTGAAAAGACTGGTTTGGTTTGGGAACCATGGCGCACAG

TATATGACCGTTCTGATTTGCCACTAGTTCGTCAGCGTACTATTAGCAAT

TGGGGCACAACCTTGTGGCCTCGCGTTGCTGAAACTGTAAAGAACGACTG

A
```

ARG3 VLY protein sequence
                                         SEQ ID NO. 11

```
MKSTKFYRNAAMLLLAGATIVPQCLAAPAMAAPSAKDSEPATSCAAKKDS

LNNYLWDLQYDKTNILARHGETIENKFSSDSFNKNGEFVVVEHQKKNITN

TTSNLSVTSANDDRVYPGALFRADKNLMDNMPSLISANRAPITLSVDLPG

FHGGESAVTVQRPTKSSVTSAVNGLVSKWNAQYGASHHVAARMQYDSASA

QSMNQLKAKFGADFAKIGVPLKIDFDAVHKGEKQTQIVNFKQTYYTVSVD

APDSPADFFAPCTTPDSLKNRGVDNKRPPVYVSNVAYGRSMYVKFDTTSK

STDFQAAVEAAIKGVEIKPNTEFHRILQNTSVTAVILGGSANGAAKVITG

NIDTLKALIQEGANLSTSSPAVPIAYTTSFVKDNEVATLQSNSDYIETKV

SSYRNGYLTLDHRGAYVARYYIYWDEYGTEIDGTPYVRSRAWEGNGKYRT

AHFNTTIQFKGNVRNLRIKLVEKTGLVWEPWRTVYDRSDLPLVRQRTISN

WGTTLWPRVAETVKND*
```

EXAMPLES

Example 1

Materials and Methods

Bacterial Strains and Cell Lines

Gardnerella vaginalis strains 14018, 14019, and 49145 were obtained from ATCC. ARG3 is a clinical isolate of G. vaginalis kindly provided by Susan Whittier. Cells were grown in brain-heart infusion supplemented with 5% fetal bovine serum, 0.3% Tween 80, and 0.1% soluble starch or in 10% fetal bovine serum (HyClone), 5% Fildes enrichment (Remel) and 4 ng/ml of amphotericin. There are many efficient ways to culture Gardnerella vaginalis known in the art. Cultures were typically incubated at 37° C. and 5% $CO_2$. E. coli strains TOP10 and BL21AI (Invitrogen) were grown in LB, with kanamycin (30 µg/ml) selection as appropriate. HeLa cells were grown at 37° C./5% $CO_2$ in MEM supplemented with 10% fetal bovine serum and 10 µg/ml ciprofloxacin. CHO-K1 cells (CCL-61) were grown at 37° C./5% $CO_2$ in F12 Kaighn's Modification (Invitrogen) with 10% FBS and 10 µg/ml ciprofloxacin.

Human cervical endothelial cells (HeLa, ATCC CCL-2) were grown at 37° C. and 5% $CO_2$ in minimal essential medium (Invitrogen) supplemented with 10% fetal bovine serum and 10 µg/ml ciprofloxacin. Human vaginal endothelial cells (VK2, ATCC CRL-2616) were grown in serum free keratinocyte growth media (Invitrogen) with 0.1 ng/ml EGF, 0.05 mg/ml bovine pituitary extract and 0.4 mM calcium chloride (Biol Reprod 1997, October 57(4):847-55, Generation of papillomavirus-immortalized cell lines from normal human ectocervical, endocervical, and vaginal epithelium that maintain expression of tissue-specific differentiation proteins; Fichorova R N, Rheinwald J G, Anderson D J).

Cloning, Sequencing, and Analysis of the VLY Gene

The G. vaginalis genomic region containing VLY was amplified from G. vaginalis 14018 by PCR using Pfx proofreading polymerase (Invitrogen) and primers V1 (ATG-CAGCGAAGCATGCCATGC) (SEQ ID NO: 19) and V2 (TCAGTCGTTCTTTACAGTTTC) (SEQ ID NO: 20). This PCR product was cloned into vector pCR2.1/TOPO (Invitrogen) and transformed into E. coli TOP10 according to the manufacturer's instructions. (50) The insert was bidirectionally sequenced using vector-specific primers. The predicted VLY open reading frame was amplified by PCR using the cloned genomic region as template, Pfx polymerase, and primers V3 (GCCGCCGCC<u>CATATG</u>AAGAGTACAAAG) (SEQ ID NO: 21) and V6 (GCC<u>GGATCC</u>TCAGTCGTTCTTTACAGT) (SEQ ID NO: 22), adding unique restriction sites indicated by underlining. The resulting product was cut with restriction enzymes NdeI and BamHI, cloned into the vector pET28a (Novagen) to generate a construct with an N-terminal hexahistidine transcriptional fusion, and confirmed by sequencing. Site-directed mutagenesis to construct (pET28a/VLY(P480W)) was performed with the QuikChange II XL kit (Stratagene) according to the manufacturer's instructions. Mutagenic primers used were P480W sense (TGGTTGAAAAGACTGGTTTGGTTTGG-GAATGGTGGCGCACAGTATAT) (SEQ ID NO: and P480W anti (ATATACTGTGCGCCACCATTCCCAAAC-CAAACCAGTCTTTTCAACCA) (SEQ ID NO: 24.

Improved purity and greater yield were achieved by generating a truncated construct (excluding the first 50 amino acids from the N-terminal region) using the primer VLY50 up (5'-GCCGCCCATATGTCGTTGAATAATTATTTGTGG-3') (SEQ ID NO: 25) along with the previously described V6 primer. The PCR product was cloned into the pET28a vector (Novagen), confirmed by sequencing, and transformed into E. coli BL21-AI competent cells (Invitrogen) for expression and purification as previously described. [11]The lytic activity of this truncated recombinant toxoid was unaltered (data not shown). The DNA sequence encoding VLY protein is set forth in SEQ ID NO: 1 for strains 14018 an 14019; the amino acid sequence encoding VLY protein is set forth in SEQ ID NO:2.

Protein sequence prediction, alignment, and phylogenetic analyses were performed using MacVector software (Version 9.5, MacVector Inc.). Protein sequences for other CDC family members (Appendix) were obtained from the Comprehensive Microbial Resource (J. Craig Venter Institute, http://cmr.tigr.org) or from the GenBank/Entrez Protein database (National Center for Biotechnology Information).

Expression and Purification of Recombinant Toxins

E. coli BL21AI carrying the pET28a/VLY or pET28a/VLY (P480W) plasmid were grown in one liter cultures at 37° C. on a rotary shaker for 3 hr, and protein expression was induced with 1 mM IPTG and 0.02% L-arabinose (Sigma). After 6 hr, bacteria were pelleted, lysed with BugBuster solution (Novagen) in the presence of protease inhibitor cocktail, lysozyme (100 µg/ml), and benzonase nuclease, all from Sigma. Lysates were cleared by centrifugation and tagged recombinant toxin purified using Ni-NTA agarose (Qiagen) according to the manufacturer's instructions. Purified toxin was extensively dialysed against LPS-free PBS (Gibco) to remove imidazole and concentrated (Amicon Ultra, 10 kD MW cutoff). Protein concentrations were determined using a modified Bradford assay (Bio-Rad).

The coding sequence of the pneumolysin gene was amplified by PCR using primers NdeI-Ply-up (GGAATTC CATATGGCAAATAAAGCAG) (SEQ ID NO: 26) and Ply-down-XhoI (CCGCTCGAGGTCATTTTCTACCTTATC) (SEQ ID NO: 27) using genomic DNA of S. pneumoniae strain TIGR4 as a template. These primers added unique restriction sites as indicated by underlining and led to amplification of the entire pneumolysin sequence, omitting the stop codon to allow addition of a C-terminal hexahistidine taG. The product was confirmed by sequencing, digested with NdeI and XhoI (New England Biolabs), and cloned into pET29a (Novagen) cut with NdeI and XhoI. The plasmid was transformed into E. coli BL21-AI, and induction and purification were performed as for VLY. Site-directed mutagenesis used primers W435P sense (ACCGGGCTTGCCTGG-GAACCGTGGCGTACG) (SEQ ID NO: 28) and W435 P anti (CGTACGCCACGGTTCCCAGGCAAGCCCGGT) (SEQ ID NO: 29).

Anti-Pneumolysin Western Blot

G. vaginalis 14018 was grown on chocolate agar and fresh colonies scraped from the plate and resuspended in lysis buffer (BugBuster, EMD Chemicals, Gibbstown, N.J.) with benzonase nuclease. The lysate was boiled for 5 minutes, and 30 µl of lysate separated on a 4-12% polyacrylamide gel (Invitrogen). Purified VLY (500 ng total) was run as a positive control. The proteins were transferred to PVDF membranes, blocked with 5% milk, and probed with murine monoclonal anti-pneumolysin (clone 9.1/2/3/6; Novocastra, Newcastle Upon Tyne, UK; 1:100 dilution). Detection was with HRP-conjugated anti-mouse IgG (Santa Cruz Biotechnology, Santa Cruz, Calif.) and ECL.

Anti-VLY Western Blot

G. vaginalis 14018 was grown on an HBT plate and fresh colonies were resuspended in lysis buffer (BugBuster, EMD Chemicals, Gibbstown N.J.) with benzonase nuclease. The lysate was boiled and separated on a 10% polyacrylamide gel. Proteins were transferred to polyvinylidene difluoride membranes, blocked with 5% milk and probed using rabbit polyclonal anti-VLY antiserum (1:500,000 dilution). Detection was with HRP-conjugated anti-rabbit IgG (Santa Cruz Biotechnology) and ECL. Membranes probed with pre-immune serum served as a negative control.

Erythrocyte Lysis Assay

The use of human erythrocytes was approved by the Columbia University Institutional Review Board. Human blood was obtained by venipuncture and erythrocytes immediately isolated by centrifugation and repeated washing in sterile PBS. For human samples, a 1% solution of packed erythrocytes in sterile PBS was prepared and added to a 96-well polystyrene V-bottomed plate (100 µl/well). Blood from other species tested was obtained commercially (Fisher Scientific) and erythrocytes washed in sterile PBS prior to use. A 1% solution of packed erythrocytes in sterile PBS was combined with an equal volume of toxin diluted in PBS. The total volume for the assay was 200 µl per well of a 96-well polystyrene V-bottom plate. The negative control for lysis consisted of PBS without toxin added to erythrocytes, and the positive control for 100% lysis was 0.05% Triton X-100. Incubation was for 30 min at 37° C./5% $CO_2$. At the conclusion of the assay, the plates were spun at 2000 rpm to pellet erythrocytes and supernatants removed for measurement of optical density at 415 nm. Where noted, toxins were preincubated with cholesterol (stock solution 100 mg/ml in chloroform; working concentration 1-10 µg/ml) or control (chloroform alone at the corresponding dilution) for 10 min at room temperature prior to use in the assay. Antibody inhibition experiments were performed using anti-CD55 (clone IA10, BD Pharmingen), anti-CD59 (clone YTH53.1, GeneTex), or irrelevant antibody control. Preincubation of erythrocytes with antibody (9 ng/ml final concentration) was for 1 hr at 4° C. with constant rotation, followed by two PBS washes to remove unbound antibody prior to use in the assay.

CHO Cell Transfection and LDH Release Assay

The coding sequence for human CD59 was amplified from cDNA from A549 (CCL-185) respiratory epithelial cells using primers CD59-1 (GCCGCC CTCGAGCCACCAATGGGAATCCAAGGAG) (SEQ ID NO: 30) and CD59-2 (GCCGCC GAATTCTTAGGGATGAAGGCTCCAGGC) (SEQ ID NO: 31) and cloned into the XhoI and EcoRI sites of pIRES2-EGFP (Clontech). Sequence was confirmed using vector specific primers. CHO-K1 cells were transfected with purified plasmid DNA (either pIRES2-EGFP/CD59 or the corresponding empty vector control) using a Nucleofector (Amaxa) according to the manufacturer's instructions. Transfected cells were plated into 6-well dishes and used 48 hr after transfection. Greater than 90% transfection efficiency was assessed by fluorescence microscopy (data not shown). Cells were weaned from serum overnight and stimulated with VLY or pneumolysin diluted in serum-free F12 media for 30 min at 37° C./5% $CO_2$. Cell viability was confirmed at the end of the experiment by visual inspection of the monolayer and trypan blue exclusion and exceeded 90%. The positive control for complete lysis was 1% Triton X-100 in serum-free F12. The concentration of lactate dehydrogenase in supernatants was assessed with a commercial kit (Roche) according to the manufacturer's instructions.

Epithelial p38 MAPK Phosphorylation

Western blot analysis of epithelial p38 MAPK phosphorylation was performed as previously described (32).

Real-Time PCR

HeLa cells were weaned from serum overnight and treated for 2 hr with medium alone, VLY (10 µg/ml), or VLY (P480W) (10 µg/ml). Cells were lysed in RLT+ buffer (Qiagen) and RNA purified using a commercially available kit (RNeasy Plus; Qiagen). Reverse transcription of 1.5 µg of RNA per sample to generate cDNA was with the high-capacity cDNA kit (Applied Biosystems). Real-time PCR (Applied Biosystems StepOne) with SYBR green detection (PowerSYBR, Applied Biosystems) was performed using primers for interleukin-8 (TACTCCAAACCTTTCCAACCC (SEQ ID NO: 32) and AACTTCTCCACAACCCTCTG(SEQ ID NO: 33)) and GAPDH (GGGCGCCTGGTCAC-CAGGGCTG (SEQ ID NO: 34) and GGGGCCATCCA-CAGTCTTCTG (SEQ ID NO: 35)). Relative quantitation used the $\Delta\Delta C_T$ method with normalization to GAPDH.

Generation of Antibodies

Purified VLY toxin was generated and submitted to Cocalico Biologicals, Inc. (Reamstown, Pa.). According to their protocol, adult rabbits were injected with a minimum of 100 µg antigen mixed with Complete Freund's Adjuvant subcutaneous and/or intramuscularly at multiple sites. Booster doses containing a minimum of 50 μg antigen mixed with Incomplete Freund's Adjuvant were administered on days 14, 21 and 49. A test bleed was performed on day 56. Prior to the first immunization, serum was collected from each rabbit to serve as negative control.

Immunofluorescence

G. vaginalis 14018 was grown to in culture media and bacterial cells were fixed on a glass chamber slide using 4% paraformaldehyde. Non-specific binding sites were blocked using 5% normal donkey serum and 0.2% triton X-100. Pre-immune or immune serum was added to each slide (1:500 dilution) for 1 h at room temperature. Following serial washes with PBS and 0.2% triton X-100, donkey anti-rabbit conjugated to Alexa Fluor (AF)-488 (Invitrogen; 1:1000 dilution) was added for 30 min in the dark with gentle shaking. After washing, chambers were removed from the slide and cover slips were mounted with ProLong Gold antifade with DAPI (Invitrogen). Slides to which no primary antibody was added served as negative controls.

ELISA Based Assay for VLY Production

Four strains of G. vaginalis (14018, 14019, 49145, and ARG3) were grown on HBT plates, colonies were scraped and inoculated into 30 ml of liquid media. A 500 μl aliquot of each culture was obtained every 6 hours for determination of $OD_{600}$. An additional 1 ml sample from each was pelleted by centrifugation and supernatant stored at −20° C. prior to ELISA.

Immuno-96 MicroWell plates (Nunc) were coated with anti-pneumolysin antibody (clone 1F11, previously shown to cross-react with VLY) diluted 1:500 in coating buffer (0.1 M sodium carbonate, pH: 9.5) and incubated at 4° C. overnight. Wells were washed with PBS and 0.05% Tween 20. Non-specific binding sites were blocked using PBS with 10% fetal bovine serum for 1 h. Supernatants (100 μl) were added to each well and plates were incubated at room temperature for 2 h. Known concentrations of recombinant VLY toxin diluted in G. vaginalis culture media were used as standards. Rabbit polyclonal anti-VLY antiserum (diluted 1:1000 in blocking solution) was added to each well for 30 min at room temperature. After washing, goat anti-rabbit HRP antibody (Santa Cruz biotechnology Inc., 1:1000 dilution) was added for 30 min. Wells were thoroughly washed and 100 μl of TMB substrate (Thermo Scientific) was added to each well and plate was incubated in the dark for 15 min. 50 μl of stop solution (2N sulfuric acid) was added to each well and $OD_{450}$ determined.

Cytotoxicity Assay 24-well plates were seeded with VK2 or HeLa human epithelial cells in appropriate media and grown to >90% confluence. 12 hours prior to use, HeLa cells were weaned from serum. Recombinant VLY toxin diluted in media (10 μg/ml) or vehicle control was added to each well. Where indicated, toxin was preincubated with pre-immune or immune sera for 30 min at 4° C. prior to use in the assay. The plates were incubated for 45 min at 37° C. and 5% $CO_2$. Supernatant was removed and the concentration of lactate dehydrogenase was determined using a commercial kit (Roche) per the manufacturer's instructions.

Statistical Analysis

Statistical comparisons were performed using two-tailed unpaired t-tests or one-way analysis of variance (ANOVA) with Tukey post-test as appropriate (Prism, GraphPad Software).

Sequence Data Availability

The sequence data for the G. vaginalis genome for strains 14018, 14019, and 49145 are available in GenBank under the accession numbers EU522486-EU522488.

Example 2

Domain 4 of VLY Plays a Role in Species Specificity

Figure 8A:
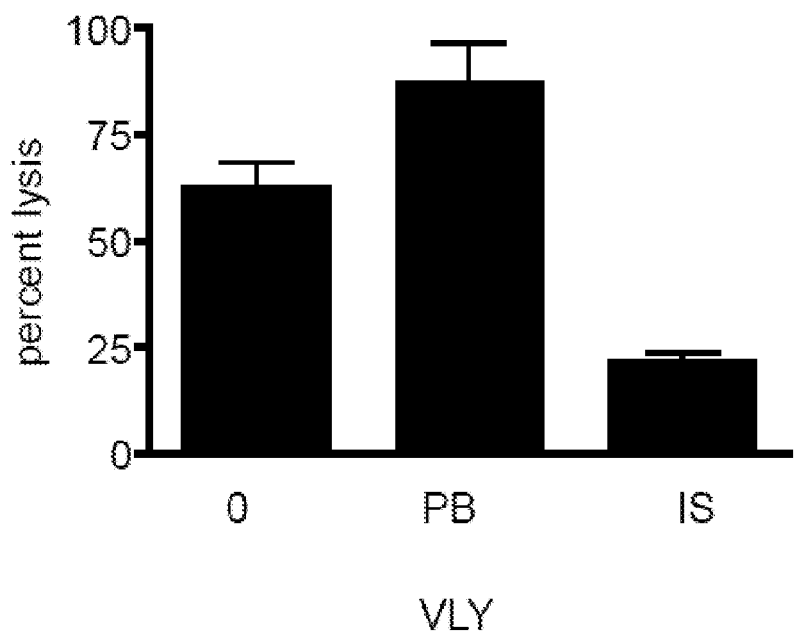
FIG. 8 Immune serum inhibits VLY-mediated lysis of human cervical and vaginal cells. Human cervical (A, HeLa) or vaginal (B, VK2) epithelial cells were exposed to VLY (10 µg/ml), VLY+PB, or VLY+IS. Lysis was measured by LDH release assay following 30 min of incubation with toxin. Values were normalized to 100% lysis for each cell line (P<0.005).
Figure 8B:
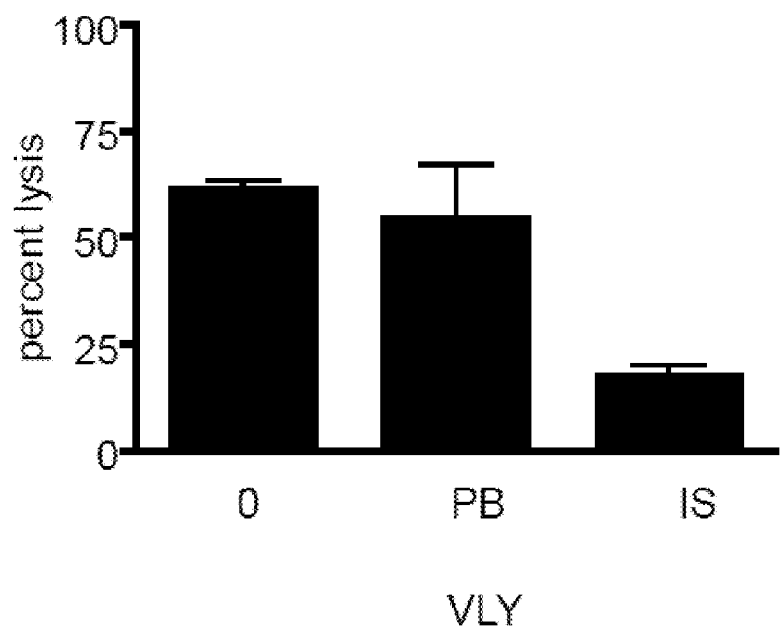

Consistent with these findings, the hCD59 binding site has been localized to this domain for ILY (22) and for VLY (FIG. 8 renumber). Using overlap-extension PCR, we generated a toxin chimera, containing domains 1-3 of VLY and domain 4 of PLY, a species non-selective CDC (FIG. 8A). Unlike the parent VLY, the chimera lysed human and non-human erythrocytes with equal efficacy (FIG. 8B), and does not require hCD59 for CHO cell lysis (FIG. 8C). This indicates that D4 plays a major role in species-selectivity among the CDCs. In order to generate a probe for toxin-hCD59 interactions, we created a GFP:VLYD4 fusion protein (FIG. 8D). This protein binds to hCD59-expressing human epithelial cells but does not form pores (FIG. 8E). Thus, this protein will be an invaluable tool for studies delineating requirements for binding between D4 and hCD59.

REFERENCES

1. Aroutcheva, A. A., J. A. Simoes, K. Behbakht, and S. Faro. 2001. *Gardnerella vaginalis* isolated from patients with bacterial vaginosis and from patients with healthy vaginal ecosystems. Clin Infect Dis 33:1022-7.
2. Billington, S. J., B. H. Jost, W. A. Cuevas, K. R. Bright, and J. G. Songer. 1997. The Arcanobacterium (Actinomyces) pyogenes hemolysin, pyolysin, is a novel member of the thiol-activated cytolysin family. J Bacteriol 179:6100-6.
3. Billington, S. J., J. G. Songer, and B. H. Jost. 2002. The variant undecapeptide sequence of the *Arcanobacterium pyogenes* haemolysin, pyolysin, is required for full cytolytic activity. Microbiology 148:3947-54.
4. Bradshaw, C. S., A. N. Morton, J. Hocking, S. M. Garland, M. B. Morris, L. M. Moss, L. B. Horvath, I. Kuzevska, and C. K. Fairley. 2006. High recurrence rates of bacterial vaginosis the course of 12 months after oral metronidazole therapy and factors associated with recurrence. J Infect Dis 193:1478-86.
5. Catlin, B. W. 1992. *Gardnerella vaginalis*: characteristics, clinical considerations, and controversies. Clin Microbiol Rev 5:213-37.
6. Cauci, S., J. F. Culhane, M. Di Santolo, and K. McCollum. 2007. Among pregnant women with bacterial vaginosis, the hydrolytic enzymes sialidase and prolidase are positively associated with interleukin-1beta. Am J Obstet Gynecol.
7. Cauci, S., S. Guaschino, D. De Aloysio, S. Driussi, D. De Santo, P. Penacchioni, and F. Quadrifoglio. 2003. Interrelationships of interleukin-8 with interleukin-1beta and neutrophils in vaginal fluid of healthy and bacterial vaginosis positive women. Mol Hum Reprod 9:53-8.
8. Cauci, S., R. Monte, M. Ropele, C. Missero, T. Not, F. Quadrifoglio, and G. Menestrina. 1993. Pore-forming and haemolytic properties of the *Gardnerella vaginalis* cytolysin. Mol Microbiol 9:1143-55.
9. Criswell, B. S., C. L. Ladwig, H. L. Gardner, and C. D. Dukes. 1969. *Haemophilus vaginalis*: vaginitis by inoculation from culture. Obstet Gynecol 33:195-9.
10. Eschenbach, D. A. 1993. History and review of bacterial vaginosis. Am J Obstet Gynecol 169:441-5.
11. Florez, C., B. Muchada, M. C. Nogales, A. Aller, and E. Martin. 1994. Bacteremia due to *Gardnerella vaginalis*: report of two cases. Clin Infect Dis 18:125.

12. Fredricks, D. N., T. L. Fiedler, and J. M. Marrazzo. 2005. Molecular identification of bacteria associated with bacterial vaginosis. N Engl J Med 353:1899-911.
13. Gardner, H. L., and C. D. Dukes. 1955. *Haemophilus vaginalis* vaginitis: a newly defined specific infection previously classified non-specific vaginitis. Am J Obstet Gynecol 69:962-76.
14. Gardner, H. L., and C. D. Dukes. 1954. New etiologic agent in nonspecific bacterial vaginitis. Science 120:853.
15. Giddings, K. S., J. Zhao, P. J. Sims, and R. K. Tweten. 2004. Human CD59 is a receptor for the cholesterol-dependent cytolysin intermedilysin. Nat Struct Mol Biol 11:1173-8.
16. Greenwood, J. R., and M. J. Pickett. 1979. Salient features of *Haemophilus vaginalis*. Clin Microbiol 9:200-4.
17. Hadders, M. A., D. X. Beringer, and P. Gros. 2007. Structure of C8alpha-MACPF reveals mechanism of membrane attack in complement immune defense. Science 317:1552-4.
18. Hillier, S. L. 2005. The complexity of microbial diversity in bacterial vaginosis. N Engl J Med 353:1886-7.
19. Huffman, D. L., L. Abrami, R. Sasik, J. Corbeil, F. G. Van der Goot, and R. V. Aroian. 2004. Mitogen-activated protein kinase pathways defend against bacterial pore-forming toxins. Proc Natl Acad Sci USA 101:10995-1000.
20. Hyman, R. W., M. Fukushima, L. Diamond, J. Kumm, L. C. Giudice, and R. W. Davis. 2005. Microbes on the human vaginal epithelium. Proc Natl Acad Sci USA 102:7952-7.
21. Ito, Y., I. Kawamura, C. Kohda, H. Baba, T. Kimoto, I. Watanabe, T. Nomura, and M. Mitsuyama. 2001. Difference in cholesterol-binding and cytolytic activities between listeriolysin O and seeligeriolysin O: a possible role of alanine residue in tryptophan-rich undecapeptide. FEMS Microbiol Lett 203:185-9.
22. Johnson, A. P., C. A. Ison, C. M. Hetherington, M. F. Osborn, G. Southerton, W. T. London, C. S. Easmon, and D. Taylor-Robinson. 1984. A study of the susceptibility of three species of primate to vaginal colonization with *Gardnerella vaginalis*. Br J Exp Pathol 65:389-96.
23. Johnson, A. P., C. A. Ison, C. M. Hetherington, M. F. Osborn, G. Southerton, W. T. London, C. S. Easmon, and D. Taylor-Robinson. 1984. Vaginal colonization of pig-tailed macaques by *Gardnerella vaginalis*. Scand J Urol Nephrol Suppl 86:207-10.
24. Korchev, Y. E., C. L. Bashford, C. Pederzolli, C. A. Pasternak, P. J. Morgan, P. W Andrew, and T. J. Mitchell. 1998. A conserved tryptophan in pneumolysin is a determinant of the characteristics of channels formed by pneumolysin in cells and planar lipid bilayers. Biochem J 329 (Pt 3):571-7.
25. Leopold, S. 1953. Heretofore undescribed organism isolated from the genitourinary system. US Armed Forces Med J 4:263-6.
26. Mardh, P. A., E. Hoist, and B. R. Moller. 1984. The grivet monkey as a model for study of vaginitis. Challenge with anaerobic curved rods and *Gardnerella vaginalis*. Scand J Urol Nephrol Suppl 86:201-5.
27. McDonald, H. M., P. Brocklehurst, and A. Gordon. 2007. Antibiotics for treating bacterial vaginosis in pregnancy. Cochrane Database Syst Rev:CD000262.
28. Nagamune, H., K. Ohkura, A. Sukeno, G. Cowan, T. J. Mitchell, W. Ito, O. Ohnishi, K. Hattori, M. Yamato, K. Hirota, Y. Miyake, T. Maeda, and H. Kourai. 2004. The human-specific action of intermedilysin, a homolog of streptolysin O, is dictated by domain 4 of the protein. Microbiol. Immunol 48:677-92.
29. Nagamune, H., C. Ohnishi, A. Katsuura, K. Fushitani, R. A. Whiley, A. Tsuji, and Y. Matsuda. 1996. Intermedilysin, a novel cytotoxin specific for human cells secreted by *Streptococcus intermedius* UNS46 isolated from a human liver abscess. Infect Immun 64:3093-100.
30. Piot, P., E. van Dyck, M. Goodfellow, and S. Falkow. 1980. A taxonomic study of *Gardnerella vaginalis* (*Haemophilus vaginalis*) Gardner and Dukes 1955. J Gen Microbiol 119:373-96.
31. Polekhina, G., K. S. Giddings, R. K. Tweten, and M. W. Parker. 2005. Insights into the action of the superfamily of cholesterol-dependent cytolysins from studies of intermedilysin. Proc Natl Acad Sci USA 102:600-5.
32. Ratner, A. J., K. R. Hippe, J. L. Aguilar, M. H. Bender, A. L. Nelson, and J. N. Weiser. 2006. Epithelial cells are sensitive detectors of bacterial pore-forming toxins. J Biol Chem 281:12994-8.
33. Reimer, L. G., and L. B. Reller. 1984. *Gardnerella vaginalis* bacteremia: a review of thirty cases. Obstet Gynecol 64:170-2.
34. Rosado, C. J., A. M. Buckle, R. H. Law, R. E. Butcher, W. T. Kan, C. H. Bird, K. Ung, K. A. Browne, K. Baran, T. A. Bashtannyk-Puhalovich, N. G. Faux, W. Wong, C. J. Porter, R. N. Pike, A. M. Ellisdon, M. C. Pearce, S. P. Bottomley, J. Emsley, A. I. Smith, J. Rossjohn, E. L. Hartland, I. Voskoboinik, J. A. Trapani, P. I. Bird, M. A. Dunstone, and J. C. Whisstock. 2007. A common fold mediates vertebrate defense and bacterial attack. Science 317:1548-51.
35. Rottini, G., A. Dobrina, O. Forgiarini, E. Nardon, G. A. Amirante, and P. Patriarca. 1990. Identification and partial characterization of a cytolytic toxin produced by *Gardnerella vaginalis*. Infect Immun 58:3751-8.
36. Sadhu, K., P. A. Domingue, A. W. Chow, J. Nelligan, N. Cheng, and J. W. Costerton. 1989. *Gardnerella vaginalis* has a gram-positive cell-wall ultrastructure and lacks classical cell-wall lipopolysaccharidE. J Med Microbiol 29:229-35.
37. Saunders, F. K., T. J. Mitchell, J. A. Walker, P. W. Andrew, and G. J. Boulnois. 1989. Pneumolysin, the thiol-activated toxin of *Streptococcus pneumoniae*, does not require a thiol group for in vitro activity. Infect Immun 57:2547-52.
38. Tweten, R. K. 2005. Cholesterol-dependent cytolysins, a family of versatile pore-forming toxins. Infect Immun 73:6199-209.
39. Witkin, S. S., I. M. Linhares, P. Giraldo, and W. J. Ledger. 2007. An altered immunity hypothesis for the development of symptomatic bacterial vaginosis. Clin Infect Dis 44:554-7.
40. Eschenbach D A, Gravett M G, Chen K C, Hoyme U B, Holmes K K. Bacterial vaginosis during pregnancy. An association with prematurity and postpartum complications. Scand J Urol Nephrol Suppl. 1984; 86:213-222.
41. Hillier S L, Nugent R P, Eschenbach D A, et al. Association between bacterial vaginosis and preterm delivery of a low-birth-weight infant. The Vaginal Infections and Prematurity Study Group. N Engl J. Med. Dec. 28, 1995; 333(26):1737-1742.
42. Watts D H, Eschenbach D A, Kenny G E. Early postpartum endometritis: the role of bacteria, genital mycoplasmas, and *Chlamydia trachomatis*. Obstet. Gynecol. January 1989; 73(1):52-60.
43. Cohen C R, Duerr A, Pruithithada N, et al. Bacterial vaginosis and HIV seroprevalence among female commercial sex workers in Chiang Mai, Thailand. Aids. September 1995; 9(9):1093-1097.
44. Taha T E, Hoover D R, Dallabetta G A, et al. Bacterial vaginosis and disturbances of vaginal flora: association with increased acquisition of HIV. Aids. Sep. 10, 1998; 12(13):1699-1706.

45. Martin H L, Richardson B A, Nyange P M, et al. Vaginal lactobacilli, microbial flora, and risk of human immunodeficiency virus type 1 and sexually transmitted disease acquisition. J Infect Dis. December 1999; 180(6):1863-1868.
46. Koumans E H, Kendrick J S. Preventing adverse sequelae of bacterial vaginosis: a public health program and research agenda. Sex Transm Dis. May 2001; 28(5):292-297.
47. Gardner H L, Dukes C D. *Haemophilus vaginalis* vaginitis: a newly defined specific infection previously classified non-specific vaginitis. Am J Obstet. Gynecol. May 1955; 69(5):962-976.
48. Josey W E, Schwebke J R. The polymicrobial hypothesis of bacterial vaginosis causation: a reassessment. Int J STD AIDS. March 2008; 19(3):152-154.
49. Schwebke J R, Rivers C, Lee J. Prevalence of *Gardnerella vaginalis* in Male Sexual Partners of Women With and Without Bacterial Vaginosis. Sex Transm Dis. Sep. 10, 2008.
50. Gelber S E, Aguilar J L, Lewis K L, Ratner A J. Functional and phylogenetic characterization of Vaginolysin, the human-specific cytolysin from *Gardnerella vaginalis*. J. Bacteriol. June 2008; 190(11):3896-3903.
51. Hogan V K, Culhane J F, Hitti J, Rauh V A, McCollum K F, Agnew K J. Relative performance of three methods for diagnosing bacterial vaginosis during pregnancy. Matern Child Health J. November 2007; 11(6):532-539.
52. Amsel R, Totten P A, Spiegel C A, Chen K C, Eschenbach D, Holmes K K. Nonspecific vaginitis. Diagnostic criteria and microbial and epidemiologic associations. Am J. Med. January 1983; 74(1):14-22.
53. Keane F E, Maw R, Pritchard C, Ison C A. Methods employed by genitourinary medicine clinics in the United Kingdom to diagnose bacterial vaginosis. Sex Transm Infect. April 2005; 81(2):155-157.
54. Nugent R P, Krohn M A, Hillier S L. Reliability of diagnosing bacterial vaginosis is improved by a standardized method of gram stain interpretation. J Clin Microbiol. February 1991; 29(2):297-301.
55. Tam M T, Yungbluth M, Myles T. Gram stain method shows better sensitivity than clinical criteria for detection of bacterial vaginosis in surveillance of pregnant, low-income women in a clinical settinG. Infect Dis Obstet Gynecol. 1998; 6(5):204-208.
56. Hedges S R, Barrientes F, Desmond R A, Schwebke J R. Local and systemic cytokine levels in relation to changes in vaginal flora. J Infect Dis. Feb. 15, 2006; 193(4):556-562.
57. Donder G G, Vereecken A, Bosmans E, Dekeersmaecker A, Salembier G, Spitz B. Definition of a type of abnormal vaginal flora that is distinct from bacterial vaginosis: aerobic vaginitis. BjoG. January 2002; 109(1):34-43.
58. Myziuk L, Romanowski B, Johnson S C. BVBlue test for diagnosis of bacterial vaginosis. J Clin Microbiol. May 2003; 41(5): 1925-1928.
59. Calderon E, Rivera R, Gordillo S, Conde-Glez C. Evaluation of a fast test to identify the presence of proline aminopeptidase in women with bacterial vaginosis. Infect Dis Obstet Gynecol. 1997; 5(3):226-231.
60. West B, Morison L, Schim van der Loeff M, et al. Evaluation of a new rapid diagnostic kit (FemExam) for bacterial vaginosis in patients with vaginal discharge syndrome in The Gambia. Sex Transm Dis. June 2003; 30(6):483-489.
61. Fredricks D N, Fiedler T L, Thomas K K, Mitchell C M, Marrazzo J M. Changes in Vaginal Bacterial Concentrations with Intravaginal Metronidazole Therapy for Bacterial Vaginosis as Assessed by Quantitative PCR. J Clin Microbiol. Jan. 14, 2009.
62. Menard J P, Fenollar F, Henry M, Bretelle F, Raoult D. Molecular quantification of *Gardnerella vaginalis* and *Atopobium vaginae* loads to predict bacterial vaginosis. Clin Infect Dis. Jul. 1, 2008; 47(1):33-43.
63. Briselden A M, Hillier S L. Evaluation of affirm VP Microbial Identification Test for *Gardnerella vaginalis* and Trichomonas vaginalis. J Clin Microbiol. January 1994; 32(1):148-152.
64. Nelson D B, Hanlon A, Hassan S, et al. Preterm labor and bacterial vaginosis-associated bacteria among urban women. J Perinat Med. Nov. 10, 2008.
65. Klein L L, Gibbs R S. Use of microbial cultures and antibiotics in the prevention of infection-associated preterm birth. Am J Obstet Gynecol. June 2004; 190(6):1493-1502.
66. McDonald H M, Brocklehurst P, Gordon A. Antibiotics for treating bacterial vaginosis in pregnancy. Cochrane Database Syst Rev. 2007 (1):CD000262.
67. Eschenbach D A, Gravett M G, Chen K C, Hoyme U B, Holmes K K. Bacterial vaginosis during pregnancy. An association with prematurity and postpartum complications. Scand J Urol Nephrol Suppl. 1984; 86:213-222.
68. Hillier S L, Nugent R P, Eschenbach D A, et al. Association between bacterial vaginosis and preterm delivery of a low-birth-weight infant. The Vaginal Infections and Prematurity Study Group. N Engl J Med Dec. 28, 1995; 333 (26):1737-1742.
69. Watts D H, Eschenbach D A, Kenny G E. Early postpartum endometritis: the role of bacteria, genital mycoplasmas, and *Chlamydia trachomatis*. Obstet Gynecol. January 1989; 73(1):52-60.
70. Cohen C R, Duerr A, Pruithithada N, et al. Bacterial vaginosis and HIV seroprevalence among female commercial sex workers in Chiang Mai, Thailand. Aids. September 1995; 9(9):1093-1097.
71. Taha T E, Hoover D R, Dallabetta G A, et al. Bacterial vaginosis and disturbances of vaginal flora: association with increased acquisition of HIV. Aids. Sep. 10, 1998; 12(13):1699-1706.
72. Martin H L, Richardson B A, Nyange P M, et al. Vaginal lactobacilli, microbial flora, and risk of human immunodeficiency virus type 1 and sexually transmitted disease acquisition. J Infect Dis. December 1999; 180(6):1863-1868.

APPENDIX

DNA SEQUENCE ALIGNMENT OF VLY DNA SEQUENCE FOR 14018, 14019 AND 49145.

```
ClustalW (v1.83) multiple sequence alignment
3 Sequences Aligned       Alignment Score = 0
Gaps Inserted = 0         Conserved Identities = 0
Pairwise Alignment Mode: Slow
Pairwise Alignment Parameters:
Open Gap Penalty = 10.0 Extend Gap Penalty = 0.1
Multiple Alignment Parameters:
```

APPENDIX-continued

```
Open Gap Penalty = 10.0 Extend Gap Penalty = 0.2
Delay Divergent = 40%   Transitions: Weighted
Processing time: 1.5 seconds
VLY14018.fa
    1  ATGAAGAGTACAAAGTTCTACCGTAATGCAGCAATGTTGCTCCTCGCGGG         50

VLY14019.fa
    1  ATGAAGAGTACAAAGTTCTACCGTAATGCAGCAATGTTGCTCCTCGCGGG         50

VLY49145.fa
    1  ATGAAGAGTACAAAGTTCTACCGTAATGCAGCAATGTTGCTCCTCGCGGG         50
       **************************************************

VLY14018.fa
   51  CGCAACTATTGTTCCACAATGCTTAGCAGCACCAGCAATGGCCGCTCCTT        100

VLY14019.fa
   51  CGCAACTATTGTTCCACAATGCTTAGCAGCACCAGCAATGGCCGCTCCTT        100

VLY49145.fa
   51  CGCAACTATTGTTCCACAATGCTTAGCAGCACCAGCAATGGCCGCTCCTT        100
       **************************************************

VLY14018.fa
  101  CCGCTAAGGATTCTGAACCAGCTACATCTTGCGCAGCTAAGAAAGACTCG        150

VLY14019.fa
  101  CCGCTAAGGATTCTGAACCAGCTACATCTTGCGCAGCTAAGAAAGACTCG        150

VLY49145.fa
  101  CCGCTAAGGATTCTGAACCAGCTACATCTTGCGCAGCTAAGAAAGACTCG        150
       **************************************************

VLY14018.fa
  151  TTGAATAATTATTTGTGGGATTTGCAATACGATAAAACAAACATTCTCGC        200

VLY14019.fa
  151  TTGAATAATTATTTGTGGGATTTGCAATACGATAAAACAAACATTCTCGC        200
VLY49145.fa
  151  TTGAATAATTATTTGTGGGATTTGCAATACGATAAAACAAACATTCTCGC        200
       **************************************************

VLY14018.fa
  201  CCGTCATGGCGAAACCATTGAGAACAAATTCTCCAGCGACAGCTTCAACA        250

VLY14019.fa
  201  CCGTCATGGCGAAACCATTGAGAACAAATTCTCCAGCGACAGCTTCAACA        250

VLY49145.fa
  201  CCGTCATGGCGAAACCATTGAGAACAAATTCTCCAGCGACAGCTTCAACA        250
       **************************************************

VLY14018.fa
  251  AGAACGGTGAATTCGTTGTTGTTGAGCATCAGAAGAAGAACATCACCAAT        300

VLY14019.fa
  251  AGAACGGTGAATTCGTTGTTGTTGAGCATCAGAAGAAGAACATCACCAAT        300

VLY49145.fa
  251  AGAACGGTGAATTCGTTGTTGTTGAGCATCAGAAGAAGAACATCACCAAT        300
       **************************************************

VLY14018.fa
  251  ACAACTTCAAATTTGTCGGTTACTTCCGCCAACGATGATCGCGTATACCC        350

VLY14019.fa
  251  ACAACTTCAAATTTGTCGGTTACTTCCGCCAACGATGATCGCGTATACCC        350

VLY49145.fa
  251  ACAACTTCAAATTTGTCGGTTACTTCCGCCAACGATGATCGCGTATACCC        350
       **************************************************

VLY14018.fa
  351  AGGTGCTCTTTTCCGTGCTGATAAGAATTTGATGGACAATATGCCAAGCC        400

VLY14019.fa
  351  AGGTGCTCTTTTCCGTGCTGATAAGAATTTGATGGACAATATGCCAAGCC        400
```

APPENDIX-continued

```
VLY49145.fa
  351  AGGTGCTCTTTTCCGTGCTGATAAGAATTTGATGGACAATATGCCAAGCC        400
       **************************************************

VLY14018.fa
  401  TGATTTCTGCAAACCGCGCTCCAATAACGTTGAGCGTTGATTTGCCGGGA        450

VLY14019.fa
  401  TGATTTCTGCAAACCGCGCTCCAATAACGTTGAGCGTTGATTTGCCGGGA        450

VLY49145.fa
  401  TGATTTCTGCAAACCGCGCTCCAATAACGTTGAGCGTTGATTTGCCGGGA        450
       **************************************************

VLY14018.fa
  451  TTCCACGGCGGCGAAAGTGCTGTAACTGTTCAGCGCCCAACCAAGAGCTC        500

VLY14019.fa
  451  TTCCACGGCGGCGAAAGTGCTGTAACTGTTCAGCGCCCAACCAAGAGCTC        500

VLY49145.fa
  451  TTCCACGGCGGCGAAAGTGCTGTAACTGTTCAGCGCCCAACCAAGAGCTC        500
       **************************************************

VLY14018.fa
  501  TGTAACTTCCGCAGTGAACGGCTTAGTTTCTAAGTGGAATGCACAATATG        550

VLY14019.fa
  501  TGTAACTTCCGCAGTGAACGGCTTAGTTTCTAAGTGGAATGCACAATATG        550

VLY49145.fa
  501  TGTAACTTCCGCAGTGAACGGCTTAGTTTCTAAGTGGAATGCACAATATG        550
       **************************************************

VLY14018.fa
  551  GAGCAAGTCATCATGTTGCAGCTCGCATGCAGTACGATTCTGCAAGCGCA        600

VLY14019.fa
  551  GAGCAAGTCATCATGTTGCAGCTCGCATGCAGTACGATTCTGCAAGCGCA        600

VLY49145.fa
  551  GAGCAAGTCATCATGTTGCAGCTCGCATGCAGTACGATTCTGCAAGCGCA        600
       **************************************************

VLY14018.fa
  601  CAAAGCATGAACCAGCTCAAGGCTAAGTTTGGTGCTGATTTTGCCAAGAT        650

VLY14019.fa
  601  CAAAGCATGAACCAGCTCAAGGCTAAGTTTGGTGCTGATTTTGCCAAGAT        650

VLY49145.fa
  601  CAAAGCATGAACCAGCTCAAGGCTAAGTTTGGTGCTGATTTTGCCAAGAT        650
       **************************************************

VLY14018.fa
  651  TGGTGTTCCGCTGAAGATTGATTTCGATGCAGTACACAAGGGTGAGAAGC        700

VLY14019.fa
  651  TGGTGTTCCGCTGAAGATTGATTTCGATGCAGTACACAAGGGTGAGAAGC        700

VLY49145.fa
  651  TGGTGTTCCGCTGAAGATTGATTTCGATGCAGTACACAAGGGTGAGAAGC        700
       **************************************************

VLY14018.fa
  701  AGACTCAAATTGTGAACTTCAAGCAAACTTACTACACCGTAAGCGTTGAT        750

VLY14019.fa
  701  AGACTCAAATTGTGAACTTCAAGCAAACTTACTACACCGTAAGCGTTGAT        750

VLY49145.fa
  701  AGACTCAAATTGTGAACTTCAAGCAAACTTACTACACCGTAAGCGTTGAT        750
       **************************************************

VLY14018.fa
  751  GCACCAGATAGCCCAGCAGATTTCTTTGCTCCTTGCACTACGCCAGACAG        800

VLY14019.fa
  751  GCACCAGATAGCCCAGCAGATTTCTTTGCTCCTTGCACTACGCCAGACAG        800
```

APPENDIX-continued

```
VLY49145.fa
  751  GCACCAGATAGCCCAGCAGATTTCTTTGCTCCTTGCACTACGCCAGACAG        800
       **************************************************

VLY14018.fa
  801  CTTGAAGAACCGTGGCGTTGACAACAAGCGCCCACCAGTTTACGTGTCAA        850

VLY14019.fa
  801  CTTGAAGAACCGTGGCGTTGACAACAAGCGCCCACCAGTTTACGTGTCAA        850

VLY49145.fa
  801  CTTGAAGAACCGTGGCGTTGACAACAAGCGCCCACCAGTTTACGTGTCAA        850
       **************************************************

VLY14018.fa
  851  ACGTAGCTTATGGTCGCTCAATGTACGTAAAGTTCGATACCACCAGCAAG        900

VLY14019.fa
  851  ACGTAGCTTATGGTCGCTCAATGTACGTAAAGTTCGATACCACCAGCAAG        900

VLY49145.fa
  851  ACGTAGCTTATGGTCGCTCAATGTACGTAAAGTTCGATACCACCAGCAAG        900
       **************************************************

VLY14018.fa
  901  AGCACTGATTTCCAGGCTGCGGTAGAAGCAGCAATTAAGGGCGTAGAAAT        950

VLY14019.fa
  901  AGCACTGATTTCCAGGCTGCGGTAGAAGCAGCAATTAAGGGCGTAGAAAT        950

VLY49145.fa
  901  AGCACTGATTTCCAGGCTGCAGTAGAAGCAGCAATTAAGGGCGTAGAAAT        950
       ******************** *****************************

VLY14018.fa
  951  CAAGCCAAACACCGAATTCCATCGCATTCTCCAGAATACTTCTGTTACTG       1000

VLY14019.fa
  951  CAAGCCAAACACCGAATTCCATCGCATTCTCCAGAATACTTCTGTTACTG       1000

VLY49145.fa
  951  CAAGCCAAACACCGAATTCCATCGCATTCTCCAAAATACTTCTGTTACTG       1000
       ********************************* ****************

VLY14018.fa
 1001  CAGTGATTCTTGGTGGCAGCGCTAATGGTGCAGCTAAAGTTATTACAGGC       1050

VLY14019.fa
 1001  CAGTGATTCTTGGTGGCAGCGCTAATGGTGCAGCTAAAGTTATTACAGGC       1050

VLY49145.fa
 1001  CAGTGATTCTTGGTGGCAGCGCTAATGGTGCAGCTAAAGTTATTACAGGC       1050
       **************************************************

VLY14018.fa
 1051  AATATCGATACGCTTAAGGCTTTGATTCAGGAAGGTGCAAATTTGAGCAC       1100

VLY14019.fa
 1051  AATATCGATACGCTTAAGGCTTTGATTCAGGAAGGTGCAAATTTGAGCAC       1100

VLY49145.fa
 1051  AACATCGATACGTTGAAGGCTTTGATTCAGGAAGGTGCAAATTTGAGCAC       1100
       ** *********  ************************************

VLY14018.fa
 1101  CTCTAGCCCAGCGGTTCCAATTGCATACACCACTTCCTTCGTCAAGGATA       1150

VLY14019.fa
 1101  CTCTAGCCCAGCGGTTCCAATTGCATACACCACTTCCTTCGTCAAGGATA       1150

VLY49145.fa
 1101  CTCTAGCCCAGCAGTTCCAATTGCATACACCACTTCCTTCGTCAAGGATA       1150
       ************ *************************************

VLY14018.fa
 1151  ACGAAGTAGCAACTTTGCAATCCAACAGCGATTATATTGAAACGAAGGTT       1200

VLY14019.fa
 1151  ACGAAGTAGCAACTTTGCAATCCAACAGCGATTATATTGAAACGAAGGTT       1200
```

APPENDIX-continued

```
VLY49145.fa
1151   ACGAAGTAGCAACTTTGCAATCCAACAGCGATTATATTGAAACGAAGGTT        1200
       **************************************************

VLY14018.fa
1201   TCTTCTTATCGCAATGGCTACTTGACTTTGGACCACCGTGGAGCTTATGT        1250

VLY14019.fa
1201   TCTTCTTATCGCAATGGCTACTTGACTTTGGACCACCGTGGAGCTTATGT        1250

VLY49145.fa
1201   TCCTCTTACCGCAATGGCTACTTGACTTTGGACCACCGTGGAGCTTACGT        1250
       **************************************************

VLY14018.fa
1251   AGCTCGCTACTACATCTACTGGGATGAGTACGGCACCGAAATTGACGGCA        1300

VLY14019.fa
1251   AGCTCGCTACTACATCTACTGGGATGAGTACGGCACCGAAATTGACGGCA        1300

VLY49145.fa
1251   AGCTCGCTACTACATCTACTGGGATGAGTACGGCACCGAAATTGACGGCA        1300
       **************************************************

VLY14018.fa
1301   CTCCTTACGTGCGTTCTCGCGCTTGGGAAGGCAATGGTAAGTATCGTACA        1350

VLY14019.fa
1301   CTCCTTACGTGCGTTCTCGCGCTTGGGAAGGCAATGGTAAGTATCGTACA        1350

VLY49145.fa
1301   CTCCTTACGTGCGTTCTCGCGCTTGGGAAGGCAATGGTAAGTATCGTACA        1350
       **************************************************

VLY14018.fa
1351   GCTCACTTCAACACCACTATTCAGTTCAAAGGAAATGTACGCAATCTACG        1400

VLY14019.fa
1351   GCTCACTTCAACACCACTATTCAGTTCAAAGGAAATGTACGCAATCTACG        1400

VLY49145.fa
1351   GCTCACTTCAATACCACTATTCAGTTCAAAGGAAATGTACGCAATCTACG        1400
       **************************************************

VLY14018.fa
1401   AATCAAGTTGGTTGAAAAGACTGGTTTGGTTTGGGAACCATGGCGCACAG        1450

VLY14019.fa
1401   AATCAAGTTGGTTGAAAAGACTGGTTTGGTTTGGGAACCATGGCGCACAG        1450

VLY49145.fa
1401   AATCAAGTTGGTTGAAAAGACTGGTTTAGTTTGGGAACCATGGCGCACAG        1450
       **************************************************

VLY14018.fa
1451   TATATGACCGTTCTGATTTGCCACTAGTTCGTCAGCGTACTATTAGCAAC        1500

VLY14019.fa
1451   TATATGACCGTTCTGATTTGCCACTAGTTCGTCAGCGTACTATTAGCAAC        1500

VLY49145.fa
1451   TATATGACCGTTCTGATTTGCCACTAGTTCATCAGCGTACTATTAGCAAC        1500
       **************************************************

VLY14018.fa
1501   TGGGGCACAACCTTGTGGCCTCGCGTTGCTGAAACTGTAAAGAACGACTG        1550

VLY14019.fa
1501   TGGGGCACAACCTTGTGGCCTCGCGTTGCTGAAACTGTAAAGAACGACTG        1550

VLY49145.fa
1501   TGGGGCACAACCTTGTGGCCTCGCGTTGCTGAAACTGTAAAGAACGACTG        1550
       **************************************************

VLY14018.fa  1551  A  1551
VLY14019.fa  1551  A  1551
VLY49145.fa  1551  A  1551
             **************************************************
```

APPENDIX-continued

AMINO ACID SEQUENCE ALIGNMENT OF VLY DNA SEQUENCE FOR 14018, 14019 AND 49145

```
ClustalW (v1.83) multiple sequence alignment
3 Sequences Aligned    Alignment Score = 0
Gaps Inserted = 0      Conserved Identities = 0
Pairwise Alignment Mode: Slow
Pairwise Alignment Parameters:
Open Gap Penalty = 10.0 Extend Gap Penalty = 0.1
Similarity Matrix: gonnet
Multiple Alignment Parameters:
Open Gap Penalty = 10.0 Extend Gap Penalty = 0.2
Delay Divergent = 40% Gap Distance = 8
Similarity Matrix: gonnet
Processing time: 0.2 seconds
VLY14018prot
   1    MKSTKFYRNAAMLLLAGATIVPQCLAAPAMAAPSAKDSEPATSCAAKKDS              50

VLY14019prot
   1    MKSTKFYRNAAMLLLAGATIVPQCLAAPAMAAPSAKDSEPATSCAAKKDS              50

VLY49145prot
   1    MKSTKFYRNAAMLLLAGATIVPQCLAAPAMAAPSAKDSEPATSCAAKKDS              50
        **************************************************

VLY14018prot
  51    LNNYLWDLQYDKTNILARHGETIENKFSSDSFNKNGEFVVVEHQKKNITN             100

VLY14019prot
  51    LNNYLWDLQYDKTNILARHGETIENKFSSDSFNKNGEFVVVEHQKKNITN             100

VLY49145prot
  51    LNNYLWDLQYDKTNILARHGETIENKFSSDSFNKNGEFVVVEHQKKNITN             100
        **************************************************

VLY14018prot
 101    TTSNLSVTSANDDRVYPGALFRADKNLMDNMPSLISANRAPITLSVDLPG             150

VLY14019prot
 101    TTSNLSVTSANDDRVYPGALFRADKNLMDNMPSLISANRAPITLSVDLPG             150

VLY49145prot
 101    TTSNLSVTSANDDRVYPGALFRADKNLMDNMPSLISANRAPITLSVDLPG             150
        **************************************************

VLY14018prot
 151    FHGGESAVTVQRPTKSSVTSAVNGLVSKWNAQYGASHHVAARMQYDSASA             200

VLY14019prot
 151    FHGGESAVTVQRPTKSSVTSAVNGLVSKWNAQYGASHHVAARMQYDSASA             200

VLY49145prot
 151    FHGGESAVTVQRPTKSSVTSAVNGLVSKWNAQYGASHHVAARMQYDSASA             200
        **************************************************

VLY14018prot
 201    QSMNQLKAKFGADFAKIG.vagina/isPLKIDFDAVHKGEKQTQIVNFKQTYYTVSVD    250

VLY14019prot
 201    QSMNQLKAKFGADFAKIG.vagina/isPLKIDFDAVHKGEKQTQIVNFKQTYYTVSVD    250

VLY49145prot
 201    QSMNQLKAKFGADFAKIG.vagina/isPLKIDFDAVHKGEKQTQIVNFKQTYYTVSVD    250
        **************************************************

VLY14018prot
 251    APDSPADFFAPCTTPDSLKNRG.vaginalisDNKRPPVYVSNVAYGRSMYVKFDTTSK    300

VLY14019prot
 251    APDSPADFFAPCTTPDSLKNRG.vaginalisDNKRPPVYVSNVAYGRSMYVKFDTTSK    300

VLY49145prot
 251    APDSPADFFAPCTTPDSLKNRG.vaginalisDNKRPPVYVSNVAYGRSMYVKFDTTSK    300
        **************************************************

VLY14018prot
 301    STDFQAAVEAAIKG.vaginalisEIKPNTEFHRILQNTSVTAVILGGSANGAAKVITG    350

VLY14019prot
 301    STDFQAAVEAAIKG.vaginalisEIKPNTEFHRILQNTSVTAVILGGSANGAAKVITG    350
```

APPENDIX-continued

```
VLY49145prot
   301  STDFQAAVEAAIKG.vaginalisEIKPNTEFHRILQNTSVTAVILGGSANGAAKVITG   350
        ********************************************

VLY14018prot
   351  NIDTLKALIQEGANLSTSSPAVPIAYTTSFVKDNEVATLQSNSDYIETKV            400

VLY14019prot
   351  NIDTLKALIQEGANLSTSSPAVPIAYTTSFVKDNEVATLQSNSDYIETKV            400

VLY49145prot
   351  NIDTLKALIQEGANLSTSSPAVPIAYTTSFVKDNEVATLQSNSDYIETKV            400
        *************************************************

VLY14018prot
   401  SSYRNGYLTLDHRGAYVARYYIYWDEYGTEIDGTPYVRSRAWEGNGKYRT            450

VLY14019prot
   401  SSYRNGYLTLDHRGAYVARYYIYWDEYGTEIDGTPYVRSRAWEGNGKYRT            450

VLY49145prot
   401  SSYRNGYLTLDHRGAYVARYYIYWDEYGTEIDGTPYVRSRAWEGNGKYRT            450
        *************************************************

VLY14018prot
   451  AHFNTTIQFKGNVRNLRIKLVEKTGLVWEPWRTVYDRSDLPLVRQRTISN            500

VLY14019prot
   451  AHFNTTIQFKGNVRNLRIKLVEKTGLVWEPWRTVYDRSDLPLVRQRTISN            500

VLY49145prot
   451  AHFNTTIQFKGNVRNLRIKLVEKTGLVWEPWRTVYDRSDLPLVHQRTISN            500
        ******************************************:******

VLY14018prot 501 WGTTLWPRVAETVKND 516
VLY14019prot 501 WGTTLWPRVAETVKND 516
VLY49145prot 501 WGTTLWPRVAETVKND 516
                 ****************
```

What is claimed is:

1. An isolated and purified pore-forming toxoid of vaginolysin from *G. vaginalis*, which toxoid differs from vaginolysin identified by SEQ ID NO: 2 by a single amino acid substitution consisting of a tryptophan residue at position 480, or an immunologically active fragment thereof comprising the single amino acid substitution.

2. An isolated and purified pore-forming toxoid of vaginolysin from *G. vaginalis*, which toxoid differs from vaginolysin identified by SEQ ID NO: 2 by a single amino acid substitution consisting of an isoleucine residue at position 500, or an immunologically active fragment thereof comprising the single amino acid substitution.

3. An isolated and purified pore-forming toxoid of vaginolysin from *G. vaginalis*, which toxoid differs from vaginolysin identified by SEQ ID NO: 2 by a single amino acid substitution consisting of an arginine [R] at position 471, or an immunologically active fragment thereof comprising the single amino acid substitution.

4. An isolated and purified pore-forming toxoid of vaginolysin from *G. vaginalis*, which toxoid differs from vaginolysin identified by SEQ ID NO: 2 by a single amino acid substitution consisting of a cysteine [C] at position 473, or an immunologically active fragment thereof comprising the single amino acid substitution.

5. An isolated and purified pore-forming toxoid of vaginolysin from *G. vaginalis*, which toxoid differs from vaginolysin identified by SEQ ID NO: 2 by two amino acid substitutions consisting of an arginine [R] at position 471 and a cysteine [C] at position 473 or an immunologically active fragment thereof comprising the two amino acid substitutions.

6. An isolated and purified pore-forming toxoid of vaginolysin from *G. vaginalis*, which toxoid differs from vaginolysin identified by SEQ ID NO: 2 by a two amino acid substitutions consisting of a tryptophan [W] at position 480, and an isoleucine at position 500, or an immunologically active fragment thereof comprising the two amino acid substitutions.

7. The isolated and purified pore-forming toxoid of claim 6, further comprising a third amino acid substitution of a cysteine [C] at position 473 of SEQ ID NO. 2 or an immunologically active fragment thereof comprising the three amino acid substitutions.

8. A method of eliciting an immune response in an animal to *G. vaginalis* vaginolysin, comprising introducing into the animal a composition comprising the isolated and purified *G.*

*vaginalis* vaginolysin toxoid protein or an immunologically active fragment thereof as claimed in one of claims 1-7.

9. A composition for treating *G. vaginalis* and bacterial vaginosis infections, comprising the isolated and purified *G. vaginalis* vaginolysin pore-forming toxoid protein or an immunologically active fragment thereof as claimed in one of claims 1-7.

10. A method of treating a *G. vaginalis* infection or bacterial vaginosis in a patient, by administering to the patient a therapeutically effective amount of the *G. vaginalis* vaginolysin pore-forming toxoid protein or an immunologically active fragment thereof as claimed in one of claims 1-7.

11. A pharmaceutical formulation comprising the isolated and purified *G. vaginalis* vaginolysin pore-forming toxoid protein or an immunologically active fragment thereof as claimed in one of claims 1-7.

12. The pharmaceutical formulation of claim 11, formulated for systemic administration.

13. The pharmaceutical formulation of claim 11, formulated for topical administration.

\* \* \* \* \*